(12) United States Patent
Omori et al.

(10) Patent No.: US 11,357,668 B2
(45) Date of Patent: Jun. 14, 2022

(54) SANITARY ARTICLE EQUIPPED WITH MOISTURE-DETECTING RFID TAG

(71) Applicant: Murata Manufacturing Co., Ltd., Nagaokakyo (JP)

(72) Inventors: Ryohei Omori, Nagaokakyo (JP); Noboru Kato, Nagaokakyo (JP); Kunihiro Komaki, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 363 days.

(21) Appl. No.: 15/983,657

(22) Filed: May 18, 2018

(65) Prior Publication Data

US 2018/0263827 A1    Sep. 20, 2018

Related U.S. Application Data

(63) Continuation of application No. PCT/JP2016/085607, filed on Nov. 30, 2016.

(30) Foreign Application Priority Data

Dec. 2, 2015  (JP) .............. JP2015-235818
Mar. 7, 2016  (JP) .............. JP2016-043592
Jun. 2, 2016  (JP) .............. JP2016-110610

(51) Int. Cl.
*A61F 13/42*     (2006.01)
*G06K 19/07*    (2006.01)
(Continued)

(52) U.S. Cl.
CPC .............. *A61F 13/42* (2013.01); *A61F 5/451* (2013.01); *A61F 13/496* (2013.01);
(Continued)

(58) Field of Classification Search
CPC ....................................... A61F 13/42
See application file for complete search history.

(56) References Cited

U.S. PATENT DOCUMENTS 6,583,722 B2     6/2003   Jeutter et al.
2002/0070864 A1  6/2002   Jeutter et al.
(Continued)

FOREIGN PATENT DOCUMENTS

CN     103116802 A      5/2013
JP     2004515314 A     5/2004
(Continued)

OTHER PUBLICATIONS

International Search Report issued for PCT/JP2016/085607, dated Mar. 7, 2017.
(Continued)

*Primary Examiner* — Catharine L Anderson
*Assistant Examiner* — Arjuna P Chatrathi
(74) *Attorney, Agent, or Firm* — ArentFox Schiff LLP

(57) ABSTRACT

A sanitary article is equipped with a moisture-detecting RFID tag that includes a moisture-absorptive material; a moisture-detecting RFID tag adjacent to the moisture-absorptive material; and a relay antenna that is connected to the moisture-detecting RFID tag and that extends the communication range by relaying an output of the moisture-detecting RFID tag. Moreover, the moisture-detecting RFID tag includes an RFIC element, and an antenna element that is connected to the RFIC element. The moisture-detecting RFID tag outputs a variation of a communication distance or a signal intensity, originated from a variation of a moisture amount included in the moisture-absorptive material.

20 Claims, 57 Drawing Sheets

(51) Int. Cl.
*G06K 19/077* (2006.01)
*A61F 13/496* (2006.01)
*A61F 5/451* (2006.01)

(52) U.S. Cl.
CPC ..... *G06K 19/0717* (2013.01); *G06K 19/0723* (2013.01); *G06K 19/07794* (2013.01); *A61F 2013/424* (2013.01)

(56) References Cited

U.S. PATENT DOCUMENTS

| | | | |
|---|---|---|---|
| 2004/0113801 A1* | 6/2004 | Gustafson | A61F 13/2051 340/604 |
| 2005/0020224 A1 | 1/2005 | Locatelli et al. | |
| 2006/0208899 A1* | 9/2006 | Suzuki | G06K 7/10178 340/572.7 |
| 2007/0182650 A1 | 8/2007 | Locatelli et al. | |
| 2013/0026237 A1* | 1/2013 | Stobbe | G06K 19/07749 235/492 |
| 2013/0076509 A1* | 3/2013 | Ahn | A61F 13/44 340/539.12 |
| 2013/0123726 A1* | 5/2013 | Yu | H01Q 1/273 604/361 |
| 2013/0131618 A1* | 5/2013 | Abraham | A61F 13/42 604/361 |
| 2014/0358099 A1* | 12/2014 | Durgin | A61F 13/42 604/361 |

FOREIGN PATENT DOCUMENTS

| | | |
|---|---|---|
| JP | 2005509356 A | 4/2005 |
| JP | 2006029993 A | 2/2006 |
| JP | 2006246372 A | 9/2006 |
| JP | 2007085817 A | 4/2007 |
| JP | 2011141238 A | 7/2011 |
| JP | 2013171429 A | 9/2013 |
| JP | 2013534839 A | 9/2013 |

OTHER PUBLICATIONS

Written Opinion of the International Searching Authority issued for PCT/JP2016/085607, dated Mar. 7, 2017.

* cited by examiner

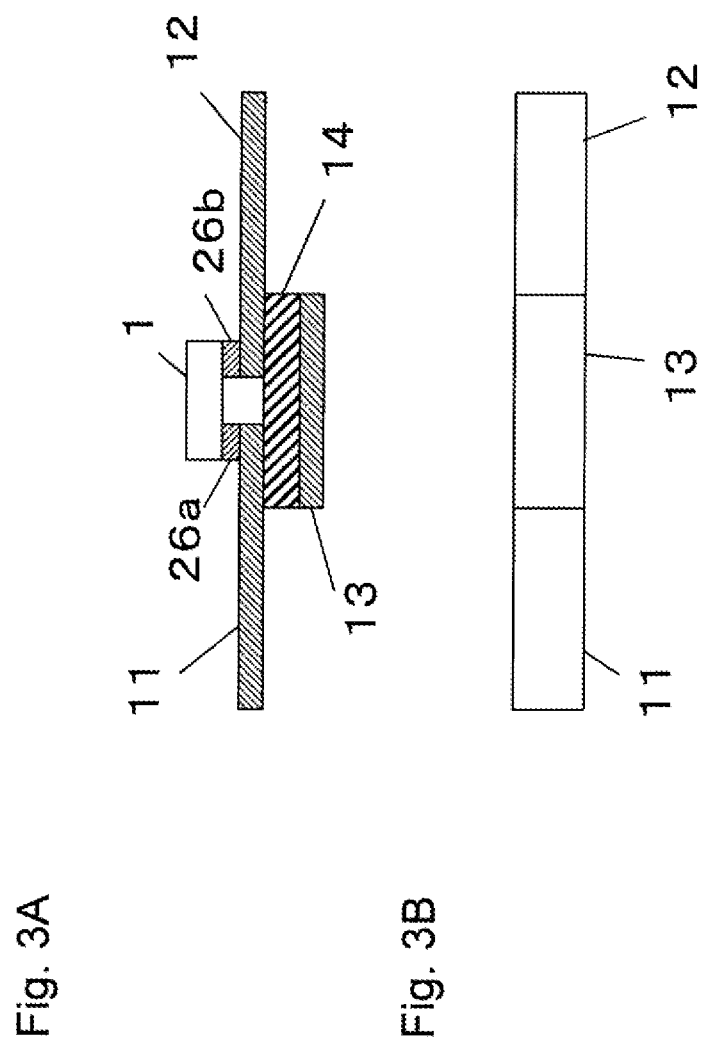

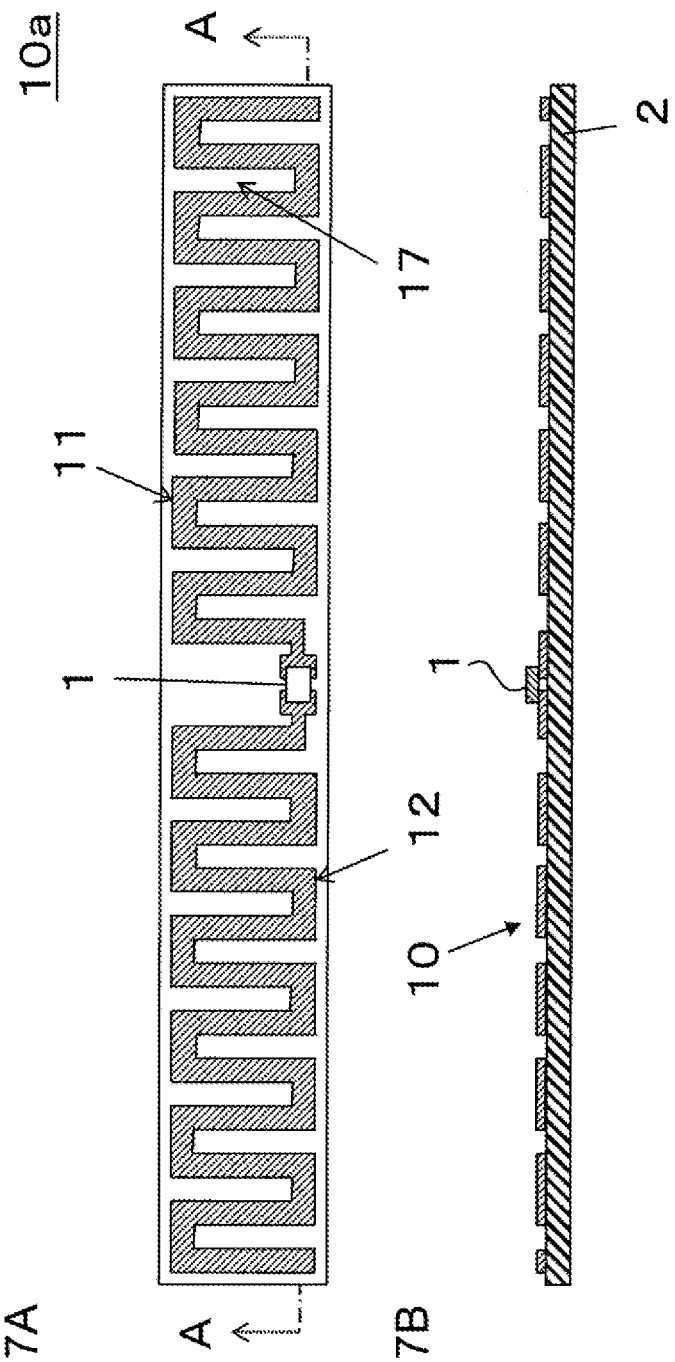
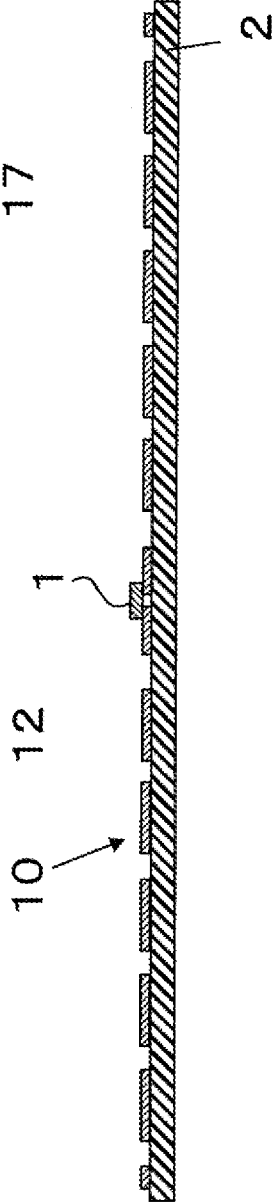
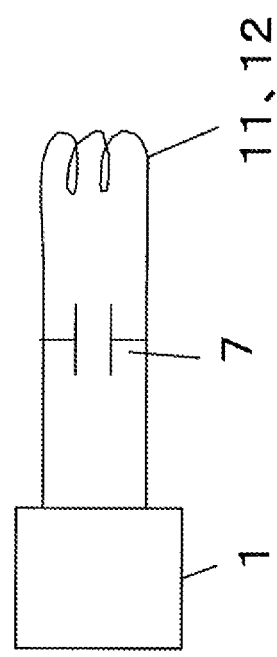
Fig 7A
Fig. 7B
Fig 7C

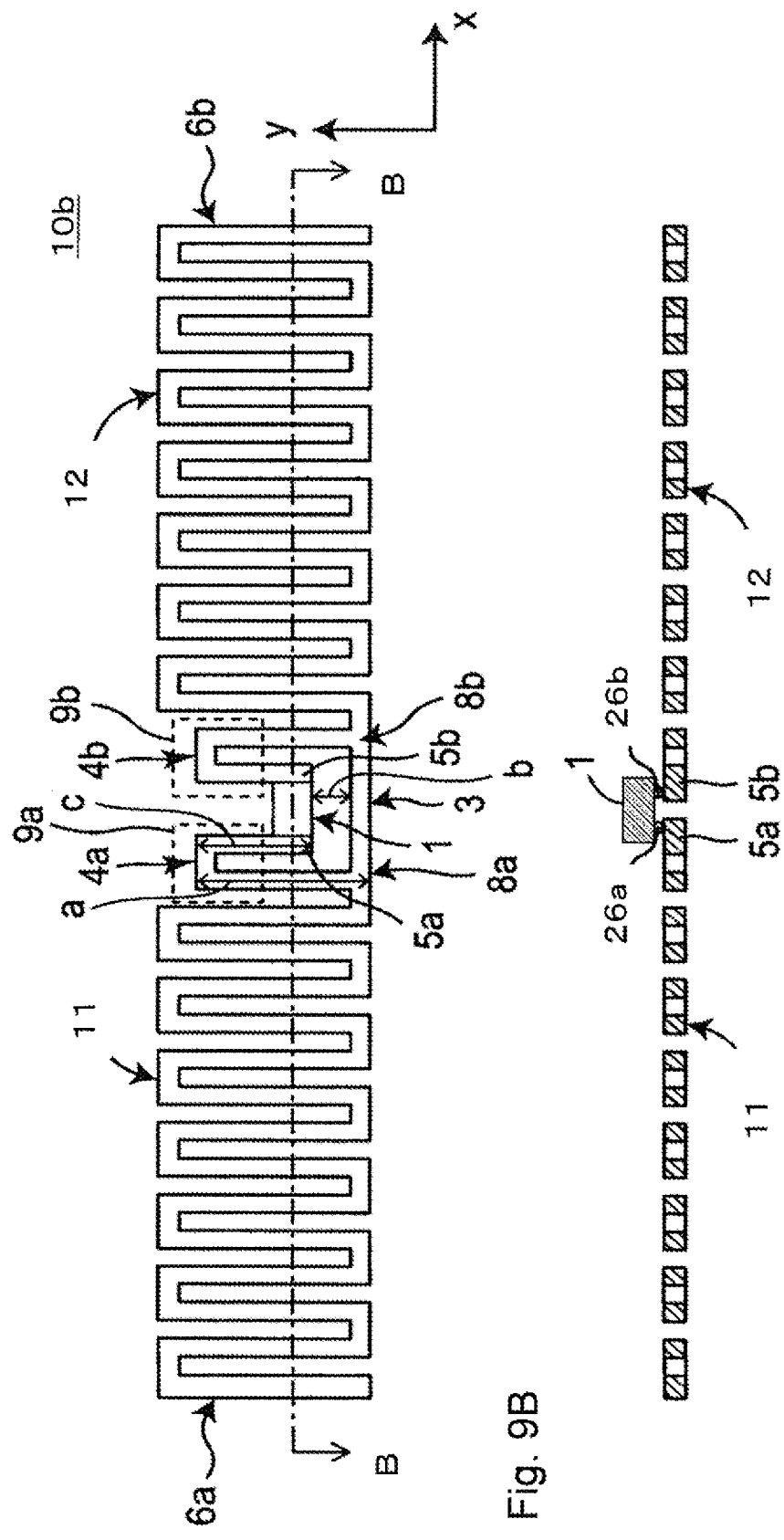

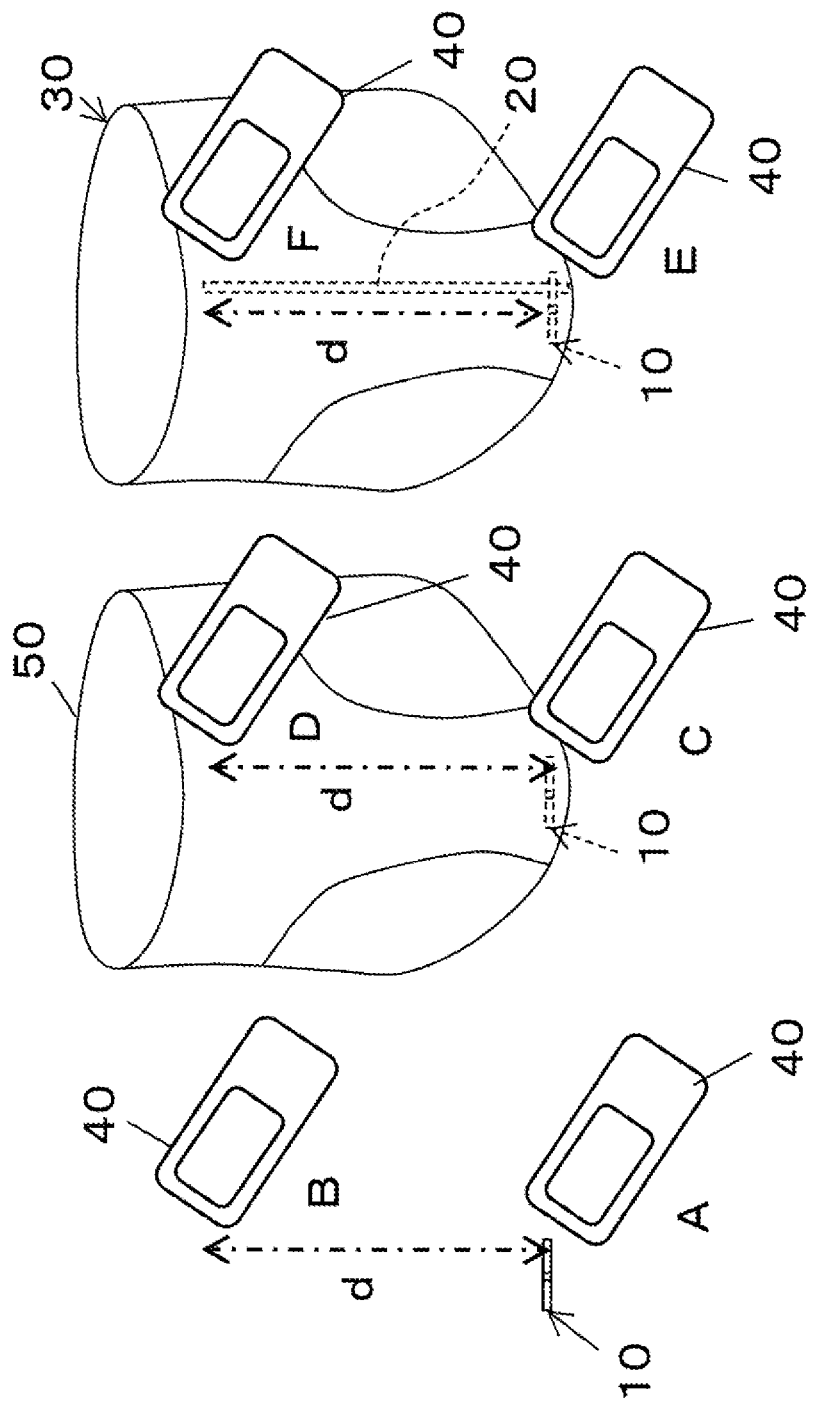

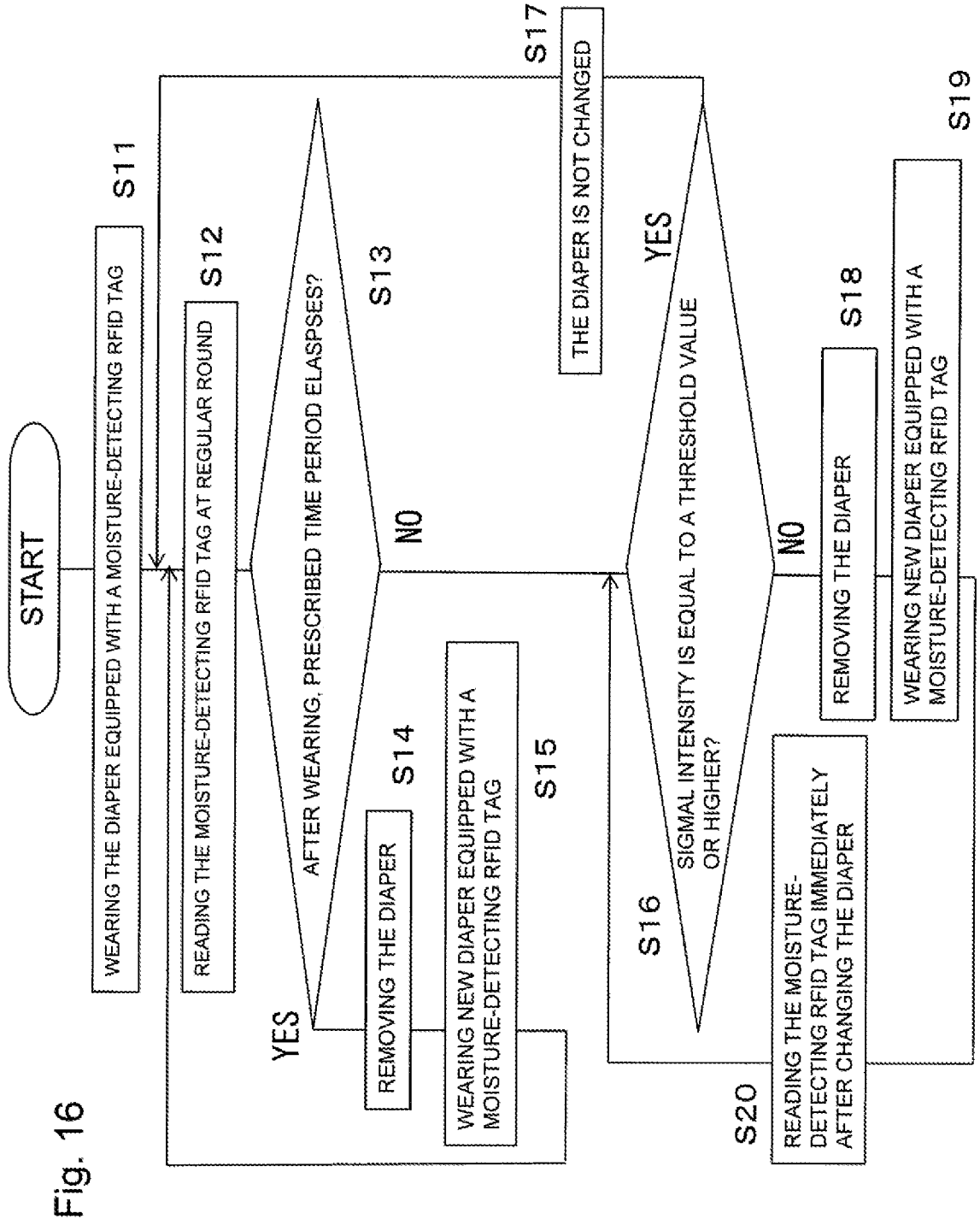

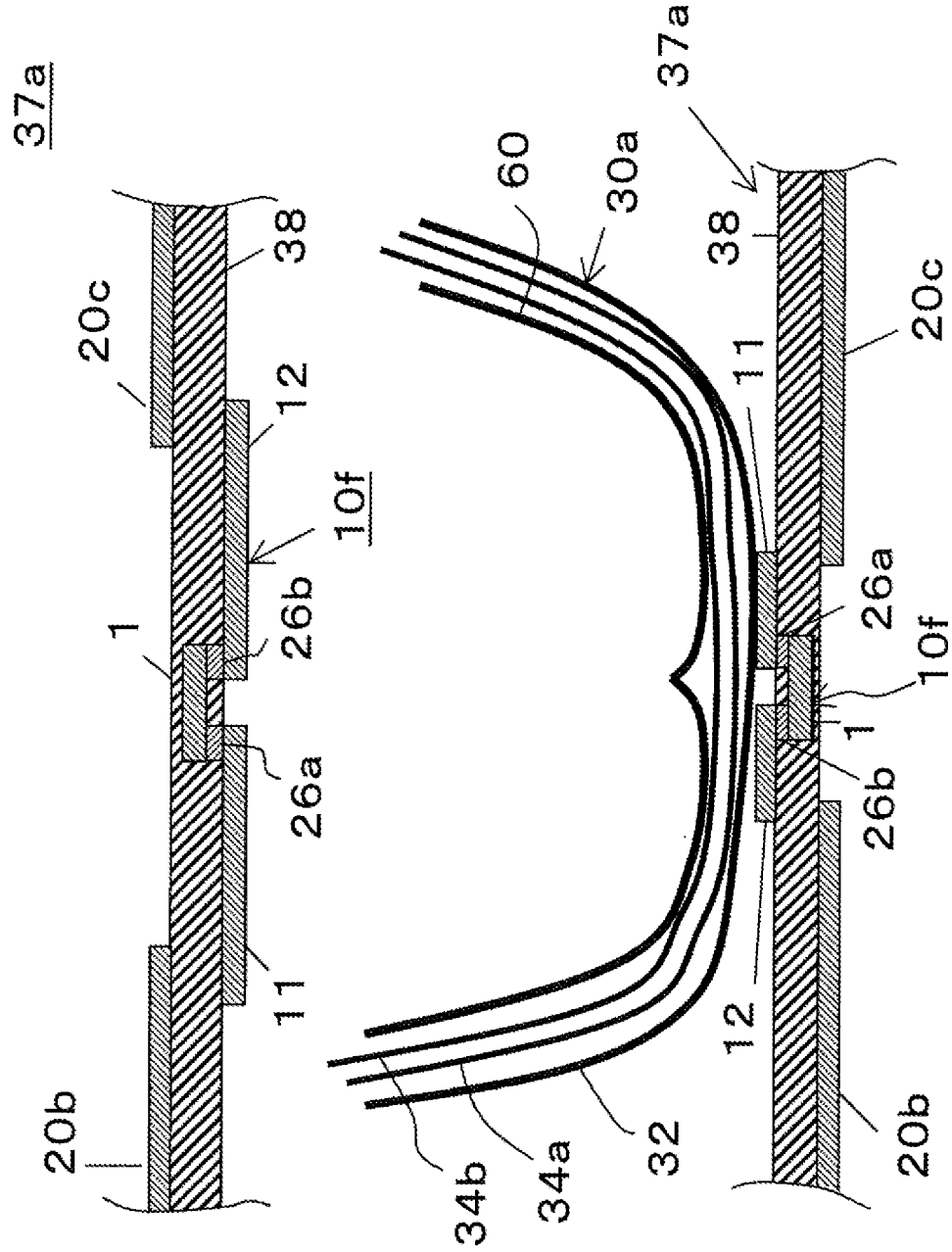

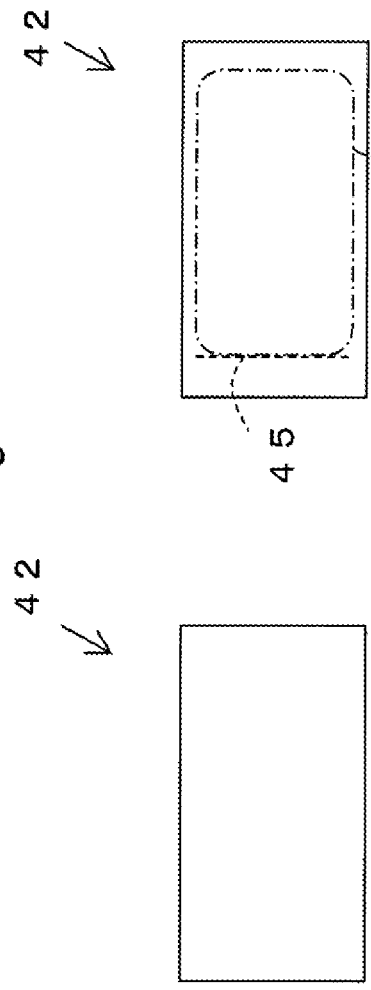
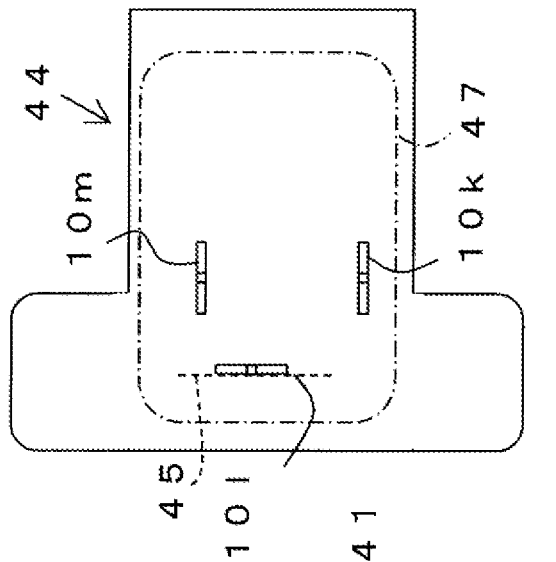
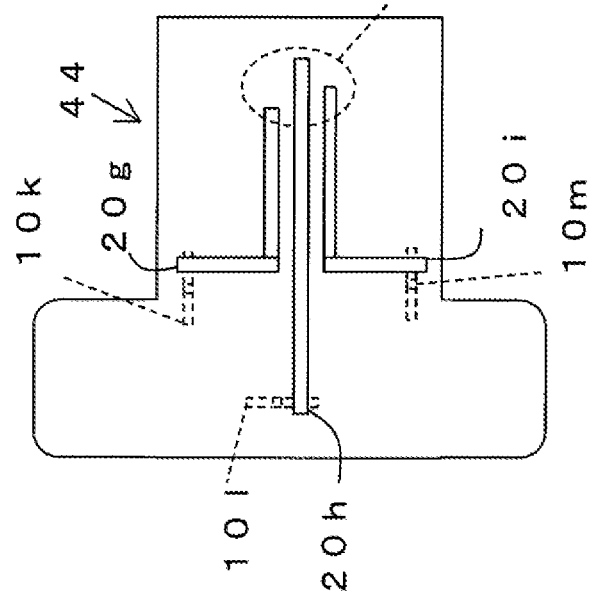
Fig. 25A  Fig. 25C  Fig. 25B  Fig. 25D

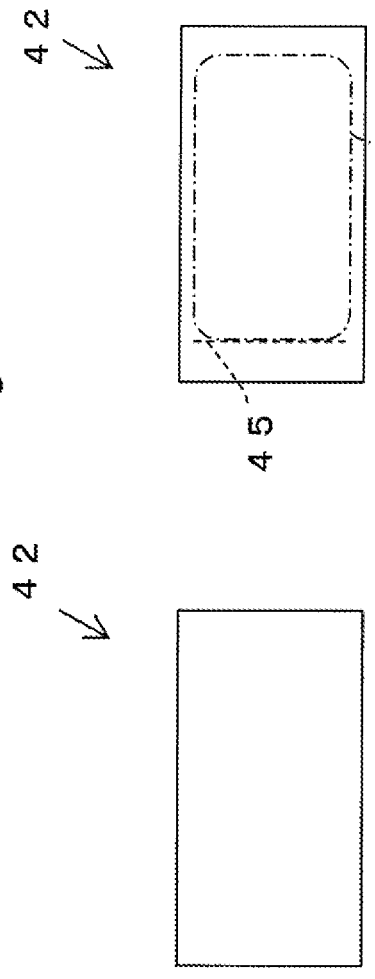
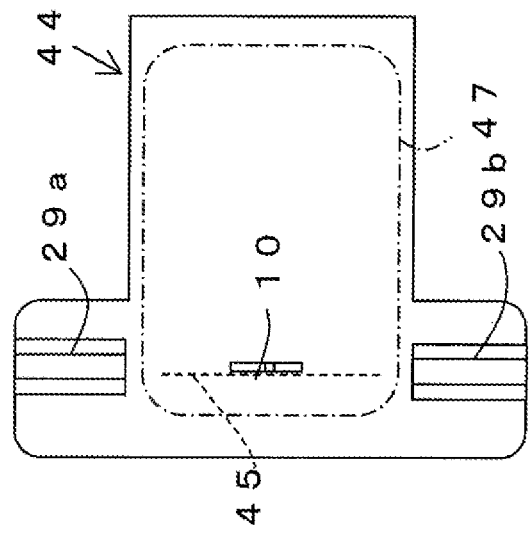
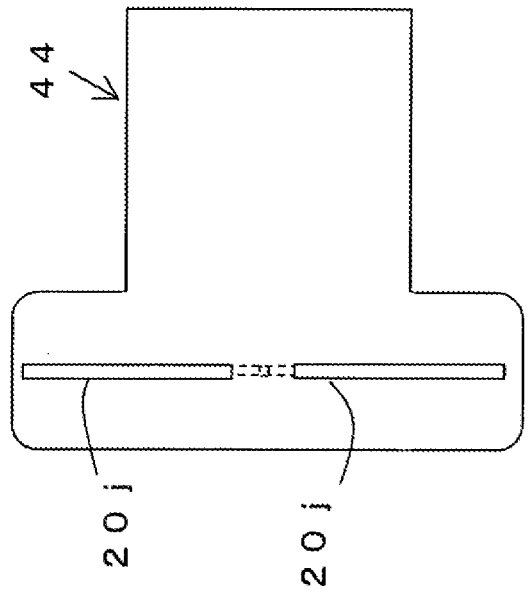

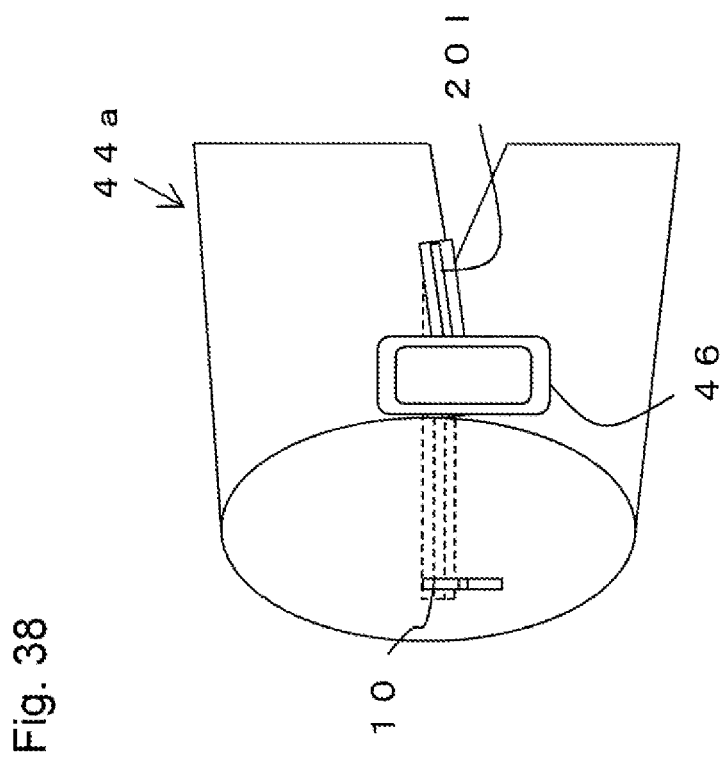

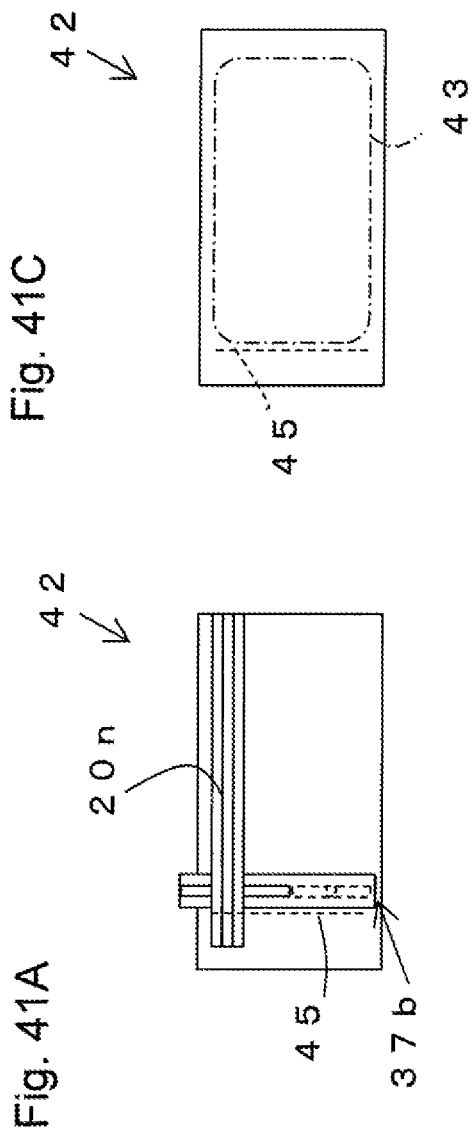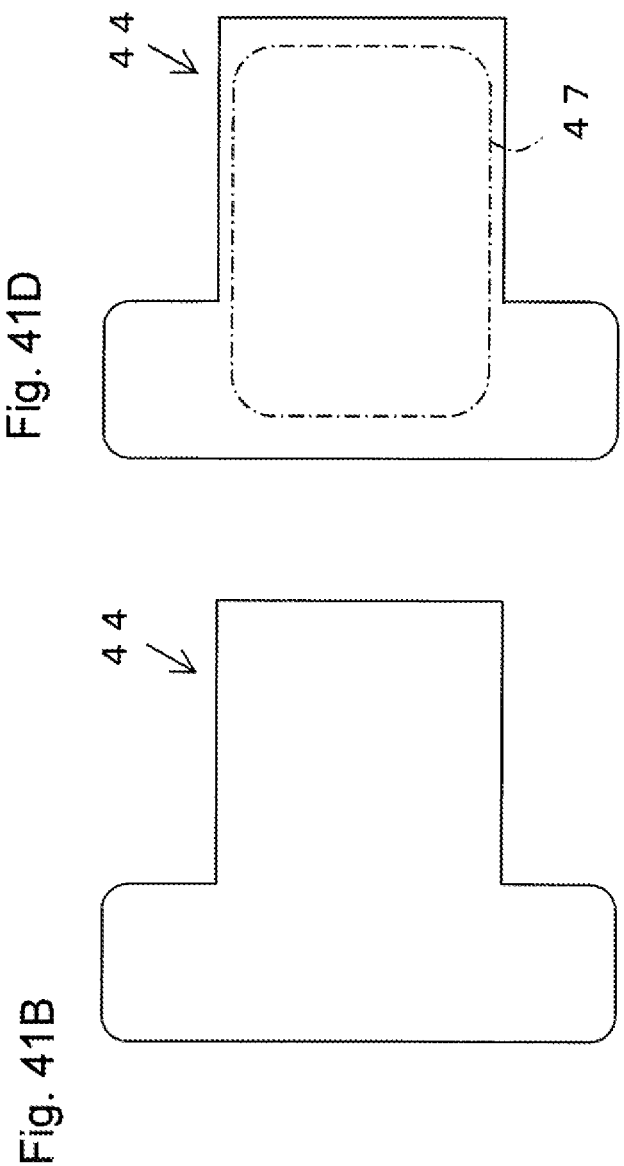

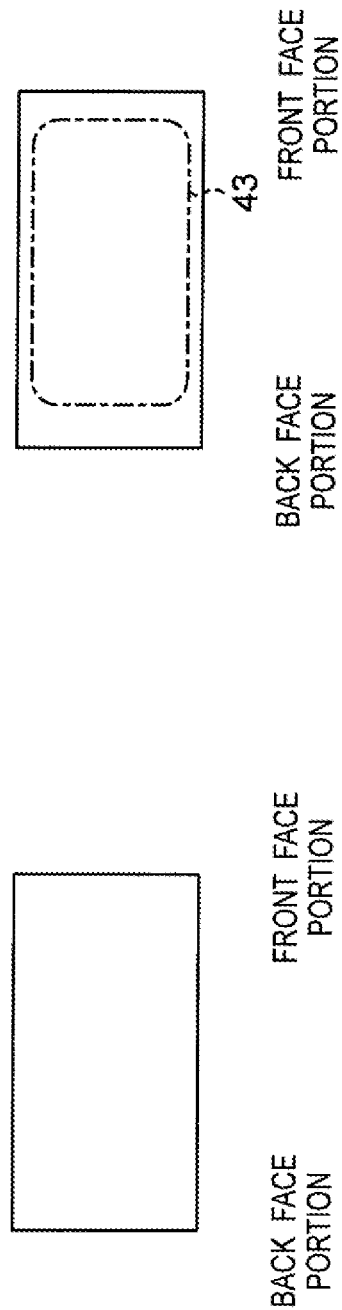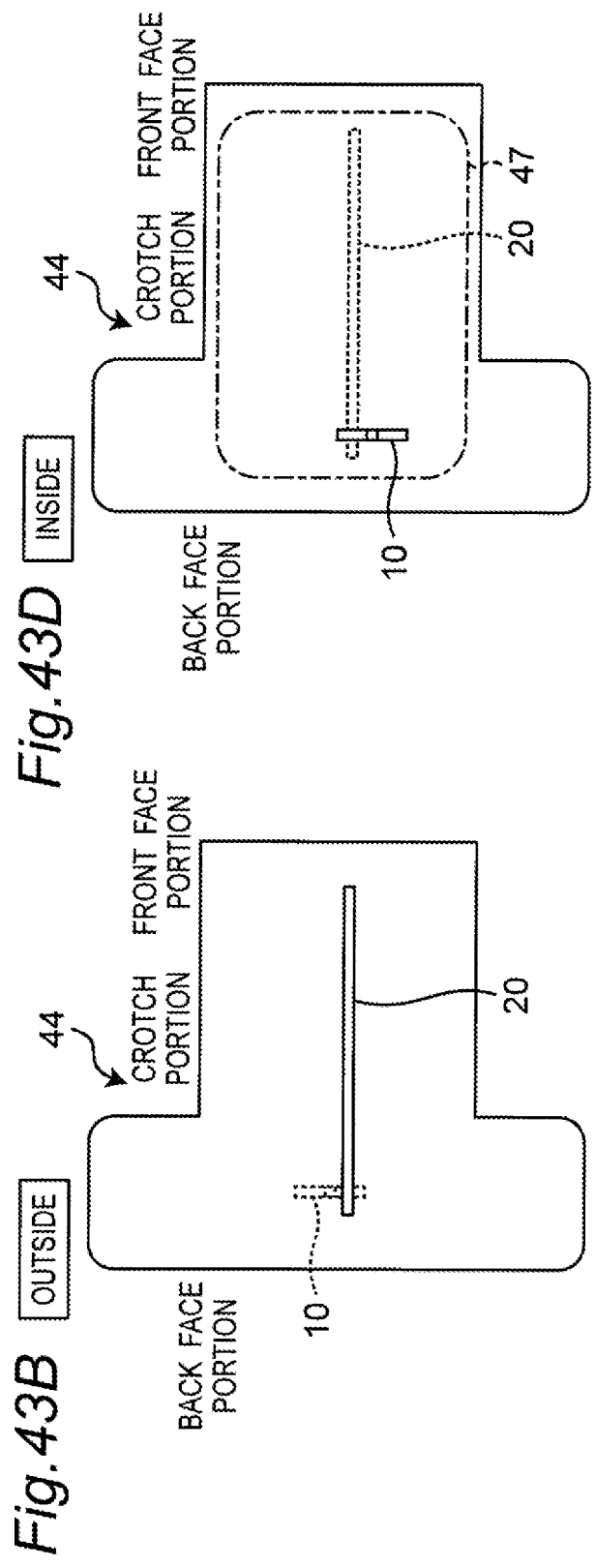

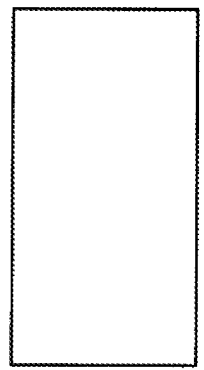
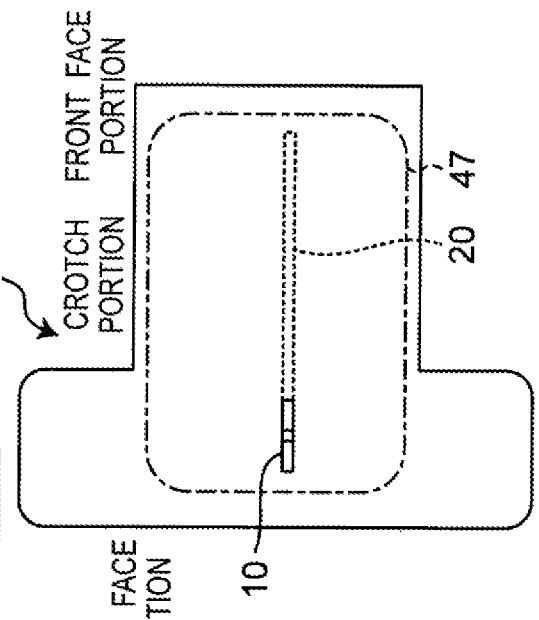
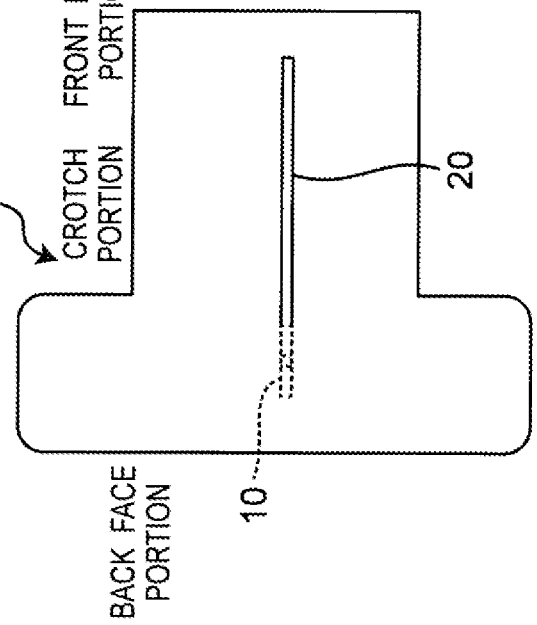

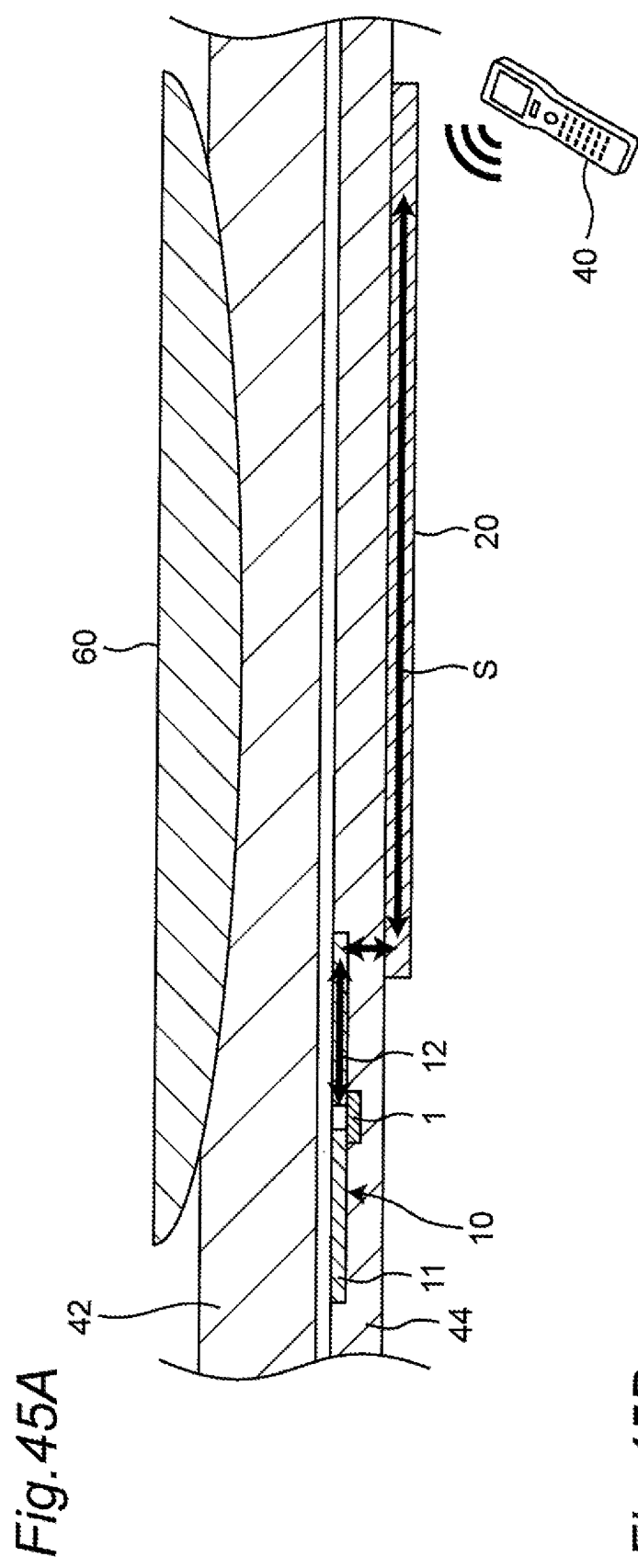
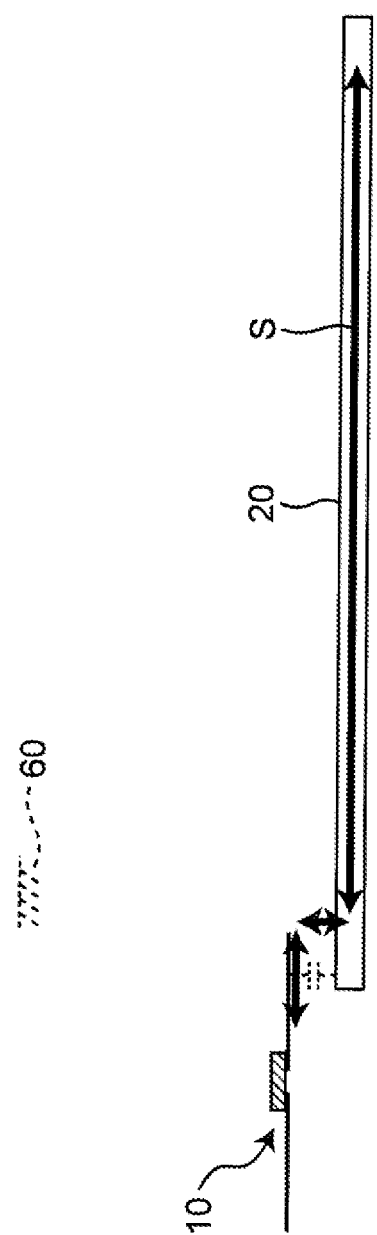
Fig.45A
Fig.45B

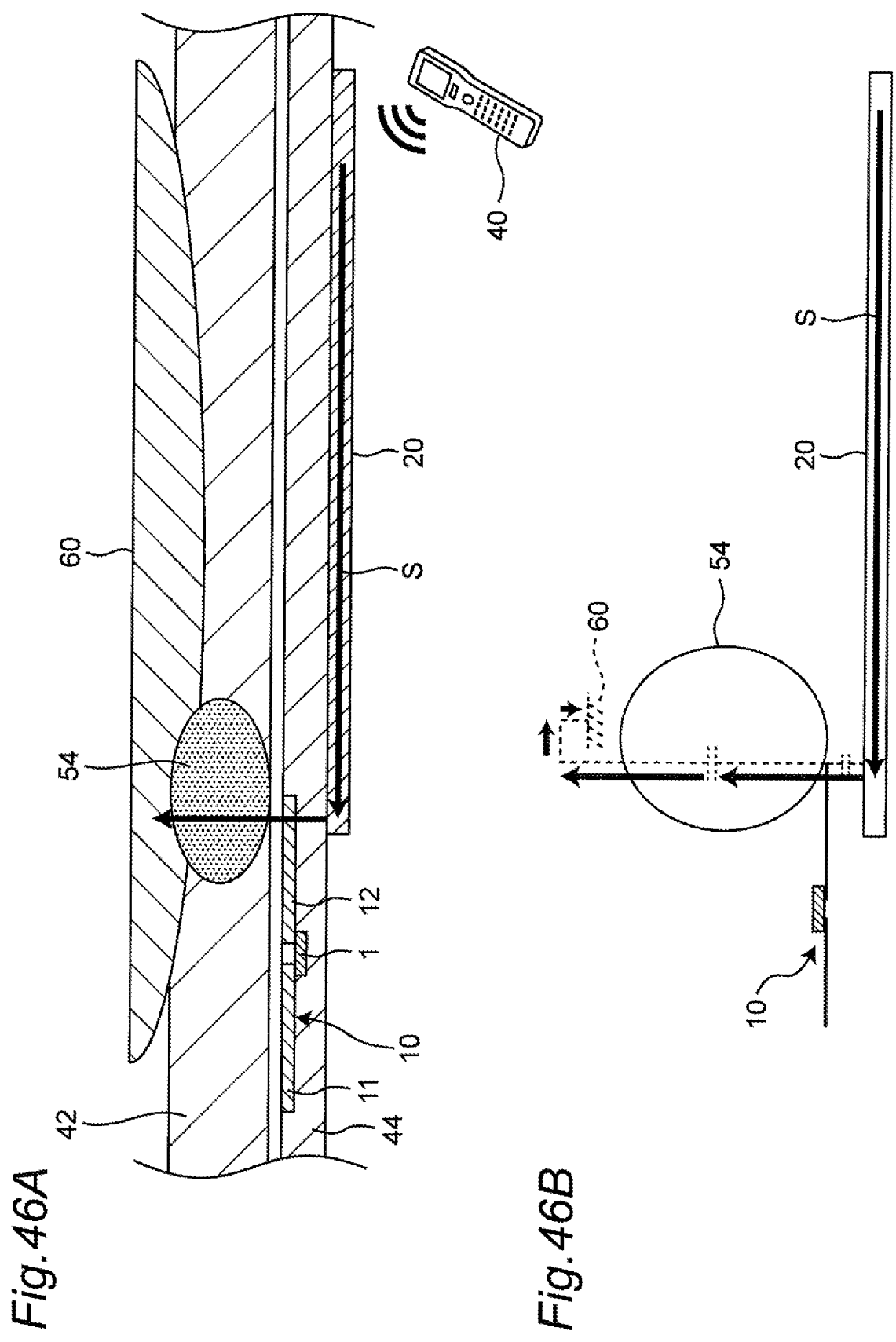

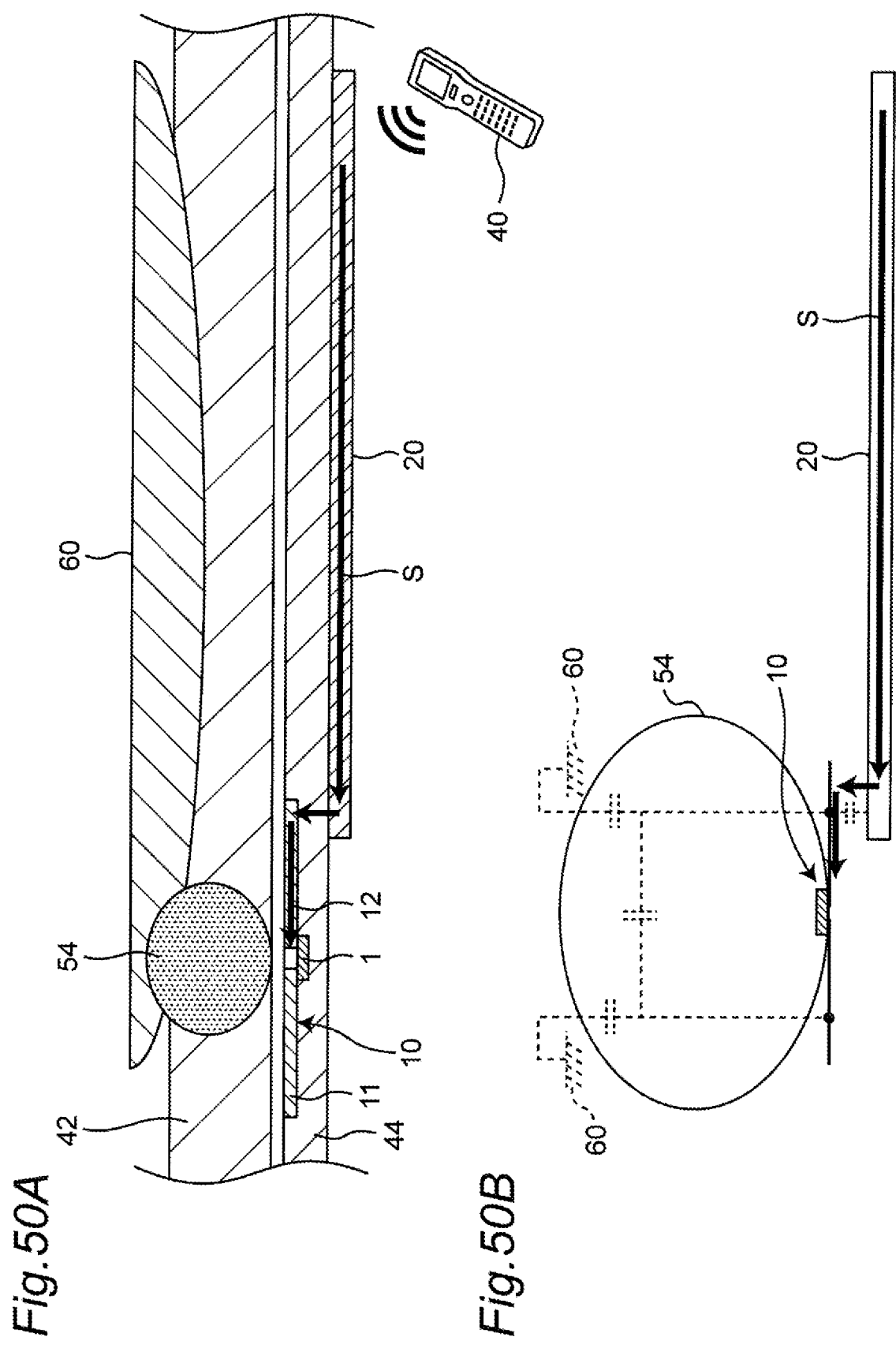

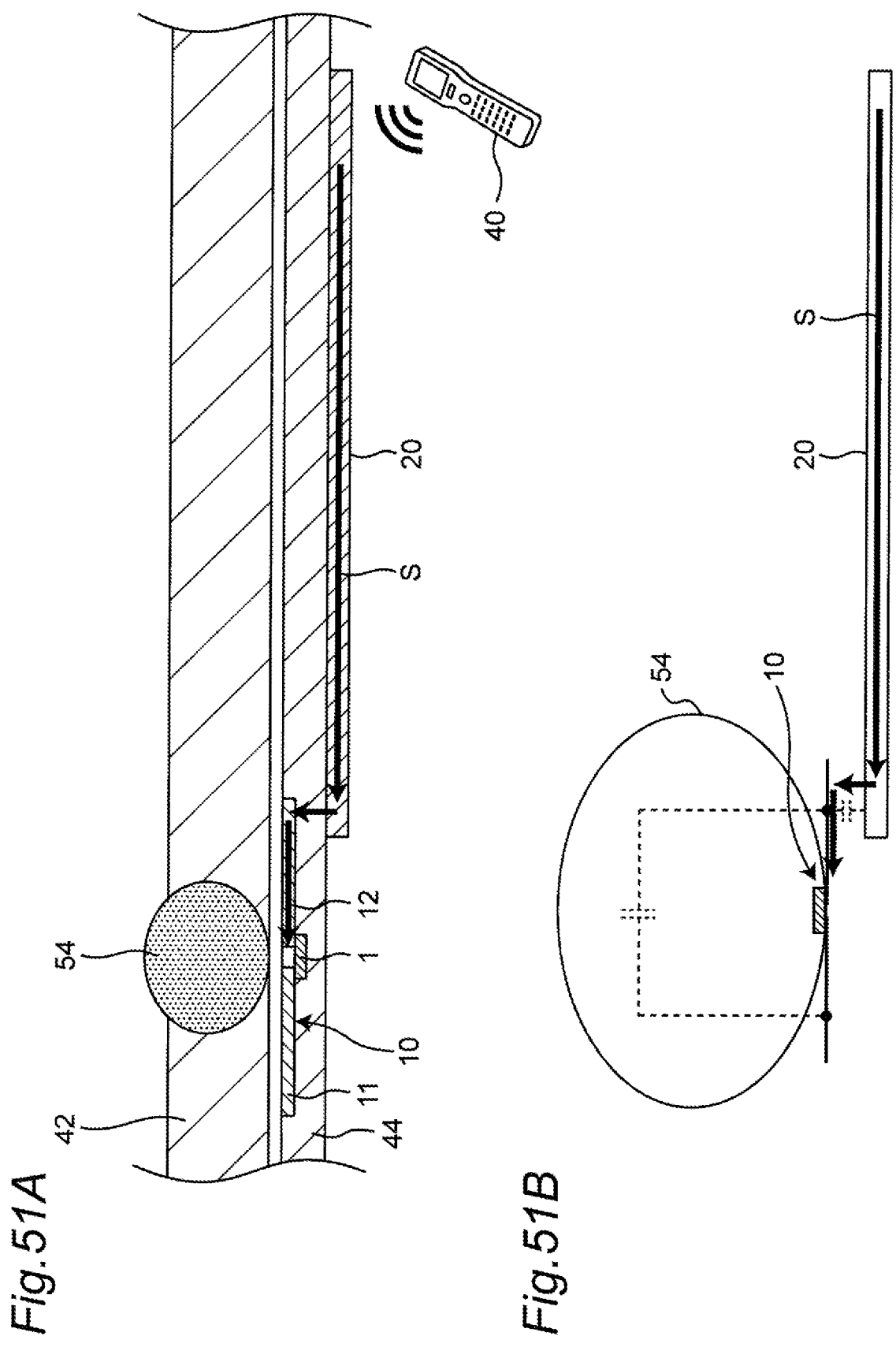

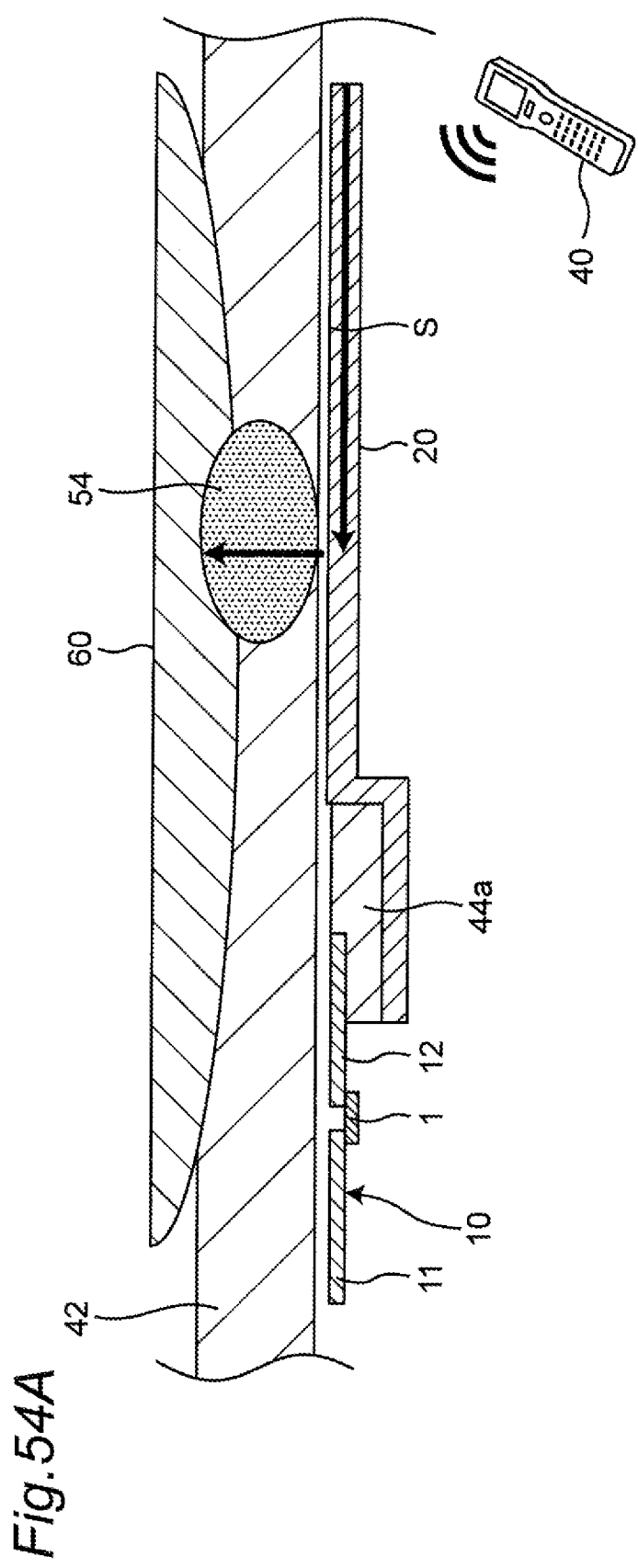
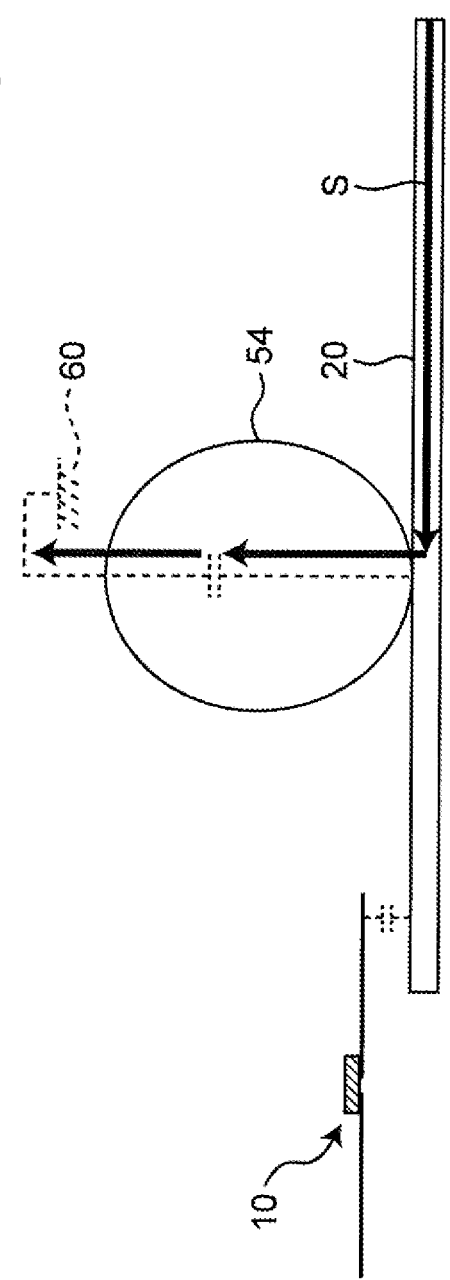
Fig.54A
Fig.54B

SANITARY ARTICLE EQUIPPED WITH MOISTURE-DETECTING RFID TAG

CROSS REFERENCE TO RELATED APPLICATIONS

The present application is a continuation of PCT/JP2016/085607 filed Nov. 30, 2016, which claims priority to Japanese Patent Application No. 2015-235818, filed Dec. 2, 2015, Japanese Patent Application No. 2016-043592, filed Mar. 7, 2016, and Japanese Patent Application No. 2016-110610, filed Jun. 2, 2016, the entire contents of each of which are incorporated herein by reference.

TECHNICAL FIELD

The present disclosure relates to a sanitary article equipped with a moisture-detecting RFID tag, capable of detecting presence of any moisture.

BACKGROUND

A sanitary article, for example, an excretion detection system has been proposed according to which an RFID tag is inserted into a diaper and a handheld reader externally reads the RFID tag to detect excrement (urine/solid waste) by mainly detecting moisture (see, e.g., Patent Document 1).

Patent Document 1: International Patent Publication No. 2013-534839

As to the system described in Patent Document 1, any detailed position for the RFID tag to be attached to the diaper and any alignment method for the RFID tag and the reader are not clearly described. No highly sensitive moisture detection can however be executed depending on the position for the RFID tag to be attached to the diaper and the positional relation between the RFID tag and the reader.

SUMMARY OF THE INVENTION

An object of the present disclosure is to provide a sanitary article equipped with a moisture-detecting RFID tag, capable of highly sensitively detecting any moisture.

The sanitary article equipped with a moisture-detecting RFID tag includes a moisture-absorptive material; a moisture-detecting RFID tag adjacent to the moisture-absorptive material; and an elongated relay antenna that is connected to the moisture-detecting RFID tag and that extends the communication range by relaying an output of the moisture-detecting RFID tag. Moreover, the moisture-detecting RFID tag includes an RFIC element; and an antenna element that is connected to the RFIC element. In this aspect, the moisture-detecting RFID tag is configured to output a variation of a communication distance or a signal intensity, originated from a variation of a moisture amount included in the moisture-absorptive material.

According to the sanitary article equipped with a moisture-detecting RFID tag of the exemplary embodiments of the present disclosure, any moisture can highly sensitively be detected in the communication range extended by the relay antenna.

BRIEF DESCRIPTION OF DRAWINGS

FIG. 3A is a sectional side diagram of a moisture-detecting RFID tag used in the diaper equipped with a moisture-detecting RFID tag, according to the first embodiment and FIG. 3B is a bottom diagram of the tag of FIG. 3A.

FIG. 7A is a top diagram of another example of the moisture-detecting RFID tag used in the diaper equipped with a moisture-detecting RFID tag, according to the first embodiment, FIG. 7B is a sectional side diagram of the cross-sectional configuration of FIG. 7A, and FIG. 7C is an equivalent circuit diagram of FIG. 7A.

FIG. 9A is a plan diagram of the configuration of yet another example of a moisture-detecting RFID tag 10b used in the diaper 30 equipped with a moisture-detecting RFID tag, according to the first embodiment and FIG. 9B is a cross-sectional diagram seen from a B-B direction in FIG. 9A.

FIG. 11A is a schematic perspective diagram of the state (A) where communication by a reader is executed in the vicinity of the moisture-detecting RFID tag alone and the state (B) where the communication by the reader is executed at a distance corresponding to the distance between a crotch portion and the front face portion of the diaper, FIG. 11B is a schematic perspective diagram of the state (C) where the communication by the reader is executed in the vicinity of the lone moisture-detecting RFID tag inserted into the crotch portion of the diaper and the state (D) where the communication by the reader is executed in the front face portion of the diaper, and FIG. 11C is a schematic perspective diagram of the state (E) where the communication by the reader is executed in the vicinity of the moisture-detecting RFID tag inserted in the crotch portion of the diaper equipped with a moisture-detecting RFID tag, according to the first embodiment and the state (F) where the communication by the reader is executed in the front face portion of the diaper.

FIG. 16 is a flowchart of a method of changing a diaper executed using the diaper equipped with a moisture-detecting RFID tag, according to the first embodiment.

FIG. 21A is a cross-sectional diagram of a cross-sectional structure of the moisture-detecting RFID tag unit of FIG. 20A and FIG. 21B is a schematic cross-sectional diagram of the state where the moisture-detecting RFID tag unit of FIG. 21A is attached on an outer face side of the diaper.

FIG. 25A is a schematic diagram of the outer side of an inner part that forms a diaper equipped with a moisture-detecting RFID tag, according to an eighth embodiment, FIG. 25B is a schematic diagram of the outer side of an outer part, FIG. 25C is a schematic diagram of the inner side of the inner part, and FIG. 25D is a schematic diagram of the inner side of the outer part.

FIG. 26A is a schematic diagram of the outer side of an inner part that forms a diaper equipped with a moisture-detecting RFID tag, according to a ninth embodiment, FIG. 26B is a schematic diagram of the outer side of an outer part, FIG. 26C is a schematic diagram of the inner side of the inner part, and FIG. 26D is a schematic diagram of the inner side of the outer part.

FIG. 38 is a schematic diagram of the case where an RFID reader and radio transfer unit 46 is used for reading of a diaper equipped with a moisture-detecting RFID tag, according to the fifteenth embodiment.

FIG. 41A is a schematic diagram of the outer side of an inner part that forms a diaper equipped with a moisture-detecting RFID tag, according to a seventeenth embodiment, FIG. 41B is a schematic diagram of the outer side of an outer part, FIG. 41C is a schematic diagram of the inner side of the inner part, and FIG. 41D is a schematic diagram of the inner side of the outer part.

FIG. 43A is a schematic diagram of the outer side of an inner part that forms a diaper equipped with an RFID tag, according to the eighteenth embodiment, FIG. 43B is a schematic diagram of the outer side of an outer part, FIG. 43C is a schematic diagram of the inner side of the inner part, and FIG. 43D is a schematic diagram of the inner side of the outer part.

FIG. 44A is a schematic diagram of the outer side of an inner part that forms a diaper equipped with an RFID tag, according to another example of the eighteenth embodiment, FIG. 44B is a schematic diagram of the outer side of an outer part, FIG. 44C is a schematic diagram of the inner side of the inner part, and FIG. 44D is a schematic diagram of the inner side of the outer part.

FIG. 45A is a schematic cross-sectional diagram of a route of a transmission signal in the communication with a reader executed when the diaper equipped with an RFID tag, according to the eighteenth embodiment is dry and FIG. 45B is a diagram of a circuit that includes the RFID tag and a relay antenna.

FIG. 46A is a schematic cross-sectional diagram of a route of the transmission signal in the communication with the reader executed when the diaper equipped with an RFID tag, according to the eighteenth embodiment has moisture absorbed therein and FIG. 46B is a diagram of a circuit that includes a human body, the moisture, the RFID tag, and the relay antenna.

FIG. 50A is a schematic cross-sectional diagram of a route of a transmission signal in the communication with a reader executed when a diaper equipped with an RFID tag, according to a nineteenth embodiment has moisture absorbed therein and FIG. 50B is a diagram of a circuit that includes a human body, the moisture, the RFID tag, and the relay antenna.

FIG. 51A is a schematic cross-sectional diagram of a route of a transmission signal in the communication with a reader executed when a diaper equipped with an RFID tag, according to a twentieth embodiment has moisture absorbed therein and FIG. 51B is a diagram of a circuit that includes the moisture, the RFID tag, and the relay antenna.

FIG. 54A is a schematic cross-sectional diagram of a route of a transmission signal in the communication with a reader executed when a diaper equipped with an RFID tag, according to Reference Example 4 has moisture absorbed therein and FIG. 54B is a diagram of a circuit that includes a human body, the moisture, the RFID tag, and the relay antenna.

DETAILED DESCRIPTION OF EXEMPLARY EMBODIMENTS

Figure 1:
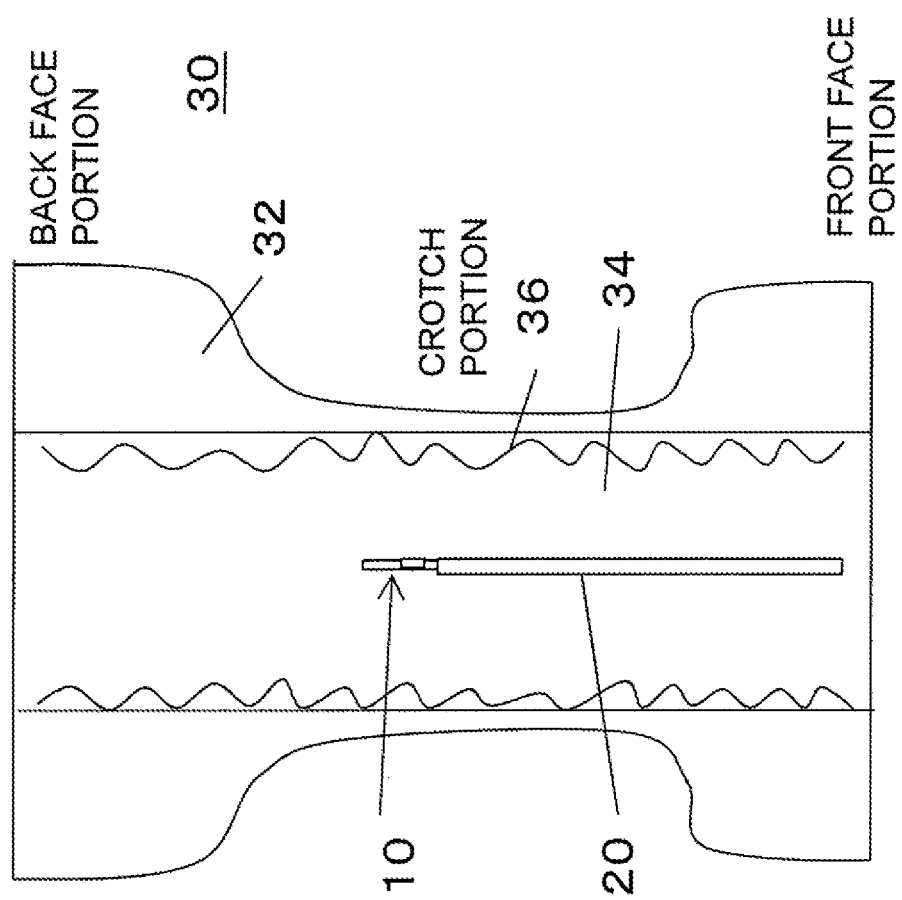
FIG. 1 is a diaper development diagram of the configuration of a diaper equipped with a moisture-detecting RFID tag, according to a first embodiment.

With the above traditional excretion detection system, taking into consideration the detection of excretion using the detection of moisture by the RFID tag, either (1) a crotch portion (an excretion portion) or (2) the back face side is desirable as the position for the RFID tag to be installed at. The crotch portion (the excretion portion) of (1) has an advantage that occurrence of any excretion can reliably and quickly be read. As to the back face side of (2), with a lying posture, urine runs reaching the back face side due to the gravity and the excretion can therefore be detected by detecting the urine accumulated on the back face side.

The above two points each desirable as the position for the RFID tag to be installed at are positions difficult to read when the handheld reader is used. With the crotch portion (the excretion portion) of (1), a problem arises that, when the reader is tried to be applied to a person needing care, the person is caused to become conscious about the reader. Thus, when the RFID tag is arranged in the crotch portion (the excretion portion), for example, even when the reader is applied to a point under the navel (the front face portion) at which the reading is easily executed, no reading electric power of the reader does not directly reach the crotch portion and no sufficient output can therefore be acquired enabling no detection. With the back face portion of (2), direct application of the reader is difficult when the posture of the person needing care is not varied. When the RFID tag is arranged in the back face portion, even when the reader is applied to the point under the navel (the front face portion), no reading electric power of the reader does not directly reach the back face portion and no sufficient output can therefore be acquired enabling no detection.

The inventors have found that a relay antenna capable of extending the communication range by relaying the output of an RFID tag was disposed for a moisture-detecting RFID tag of a diaper and highly sensitive moisture detection was enabled in the communication range extended by the relay antenna, and the inventor completed the present invention.

A sanitary article equipped with a moisture-detecting RFID tag, according to a first aspect, the sanitary article includes a moisture-absorptive material; a moisture-detecting RFID tag disposed to be adjacent to the moisture-absorptive material; and a relay antenna that is connected to the moisture-detecting RFID tag and that extends the communication range by relaying an output of the moisture-detecting RFID tag. Moreover, the moisture-detecting RFID tag includes an RFIC element; and an antenna element that is connected to the RFIC element. In this aspect, the moisture-detecting RFID tag is configured to output a variation of a communication distance or a signal intensity, originated from a variation of a moisture amount included in the moisture-absorptive material.

According to the above configuration, any moisture can highly sensitively be detected in the communication range extended by the relay antenna.

The sanitary article equipped with a moisture-detecting RFID tag, according to a second aspect, wherein the relay antenna may be capacitively coupled with the antenna element of the moisture-detecting RFID tag, in the first aspect.

The sanitary article equipped with a moisture-detecting RFID tag, according to a third aspect may include an inner part that includes the moisture-absorptive material and an outer part that covers the inner part, in the first aspect.

The sanitary article equipped with a moisture-detecting RFID tag, according to a fourth aspect, wherein the outer part may be an underpants-type outer part, in the third aspect.

The sanitary article equipped with a moisture-detecting RFID tag, according to a fifth aspect, wherein the moisture-detecting RFID tag may be arranged on the inner side of the outer part, and wherein the relay antenna may be arranged on the outer side of the outer part that faces an antenna element of the moisture-detecting RFID tag sandwiching the outer part therebetween to be capacitively coupled with the antenna element of the moisture-detecting RFID tag, in the third or the fourth aspect.

The sanitary article equipped with a moisture-detecting RFID tag, according to a sixth aspect, may include plural pairs each of the moisture-detecting RFID tag and the relay antenna connected to the moisture-detecting RFID tag, in any one of the first to the fifth aspects.

The sanitary article equipped with a moisture-detecting RFID tag, according to a seventh aspect, wherein the sanitary article may be a diaper, in any one of the first to the sixth aspects.

The sanitary article equipped with a moisture-detecting RFID tag, according to an eighth aspect, wherein the moisture-detecting RFID tag may be arranged in a crotch portion of the diaper, and wherein the relay antenna may be extended from the crotch portion of the diaper to a front face portion and/or a back face portion thereof, in the seventh aspect.

The sanitary article equipped with a moisture-detecting RFID tag, according to a ninth aspect, wherein the moisture-detecting RFID tag may be arranged in the back face portion of the diaper, and wherein the relay antenna may be extended from the back face portion of the diaper to the front face portion thereof, in the seventh or the eighth aspect.

The sanitary article equipped with a moisture-detecting RFID tag, according to a tenth aspect, wherein the relay antenna may be extended from the back face portion to the front face portion through the crotch portion of the diaper, in the ninth aspect.

A relay antenna unit for a sanitary article equipped with a moisture-detecting RFID tag, according to an eleventh aspect, includes a band-like supporter; and a relay antenna that is disposed on the supporter and that is arranged to face an antenna element of a moisture-detecting RFID tag arranged on the inner face side of the sanitary article through a portion of the sanitary article, to be capacitively coupled with the antenna element of the moisture-detecting RFID tag to thereby extend a communication range by relaying an output of the moisture-detecting RFID tag.

A moisture-detecting RFID tag unit according to a twelfth aspect includes a band-like supporter, a moisture-detecting RFID tag that is disposed on the supporter, and a relay antenna that is capacitively coupled with an antenna element of the moisture-detecting RFID tag and that thereby extends a communication range by relaying an output of the moisture-detecting RFID tag.

A sanitary article equipped with a moisture-detecting RFID tag, according to a thirteenth aspect includes a sanitary article that includes an inner part including a moisture-absorptive material and an outer part covering the inner part, and a moisture-detecting RFID tag unit that is arranged in the sanitary article and that is configured to output a variation of a communication distance or a signal intensity, originated from a variation of a moisture amount included in the moisture-absorptive material. Moreover, the moisture-detecting RFID tag unit includes a band-like supporter, a moisture-detecting RFID tag that is disposed on the supporter, and a relay antenna that is capacitively coupled with an antenna element of the moisture-detecting RFID tag to thereby extend a communication range by relaying an output of the moisture-detecting RFID tag.

The sanitary article equipped with a moisture-detecting RFID tag, according to a fourteenth aspect, wherein the outer part may be an underpants-type outer part, in the thirteenth aspect.

The sanitary article equipped with a moisture-detecting RFID tag, according to a fifteenth aspect, wherein the moisture-detecting RFID tag unit may be arranged on the outer side of the inner part, in the thirteenth or the fourteenth aspect.

The sanitary article equipped with a moisture-detecting RFID tag, according to a sixteenth aspect, wherein the moisture-detecting RFID tag unit may be arranged on the inner side of the outer part, in the thirteenth or the fourteenth aspect.

The sanitary article equipped with a moisture-detecting RFID tag, according to a seventeenth aspect, wherein the moisture-detecting RFID tag unit may be arranged on the outer side of the outer part, in the thirteenth or the fourteenth aspect.

The sanitary article equipped with a moisture-detecting RFID tag, according to an eighteenth aspect may further include another relay antenna that is connected to the relay antenna of the moisture-detecting RFID tag unit, in any one of the thirteenth to the seventeenth aspects.

The sanitary article equipped with a moisture-detecting RFID tag, according to a nineteenth aspect, wherein plural moisture-detecting RFID tag units may be arranged, in any one of the thirteenth to the eighteenth aspects.

A moisture-detecting RFID device according to a twentieth aspect includes a moisture-absorptive material, an RFID tag disposed to be adjacent to the moisture-absorptive material, and a relay antenna that is connected to the RFID tag to extend the communication range by relaying an output of the RFID tag, wherein the RFID tag includes an RFIC element, and an antenna element that is connected to the RFIC element and is coupled with the relay antenna, and wherein a capacitance portion is constituted between a portion of the antenna element and/or the antenna element, and the relay antenna through the moisture-absorptive material, of the RFID tag and is configured to output a variation of a communication distance or a signal intensity, originated from a variation of a moisture amount included in the moisture-absorptive material.

A sanitary article equipped with a moisture-detecting RFID tag, according to each of embodiments will be described below with reference to the accompanying drawings. Substantially same members are given the same reference numerals in the drawings.

First Embodiment

<Diaper Equipped with Moisture-Detecting RFID Tag>

In the exemplary aspect, the moisture-detecting RFID tag is preferably a UHF-band RFID tag that uses the UHF-band as its carrier frequency band.

Figure 2:
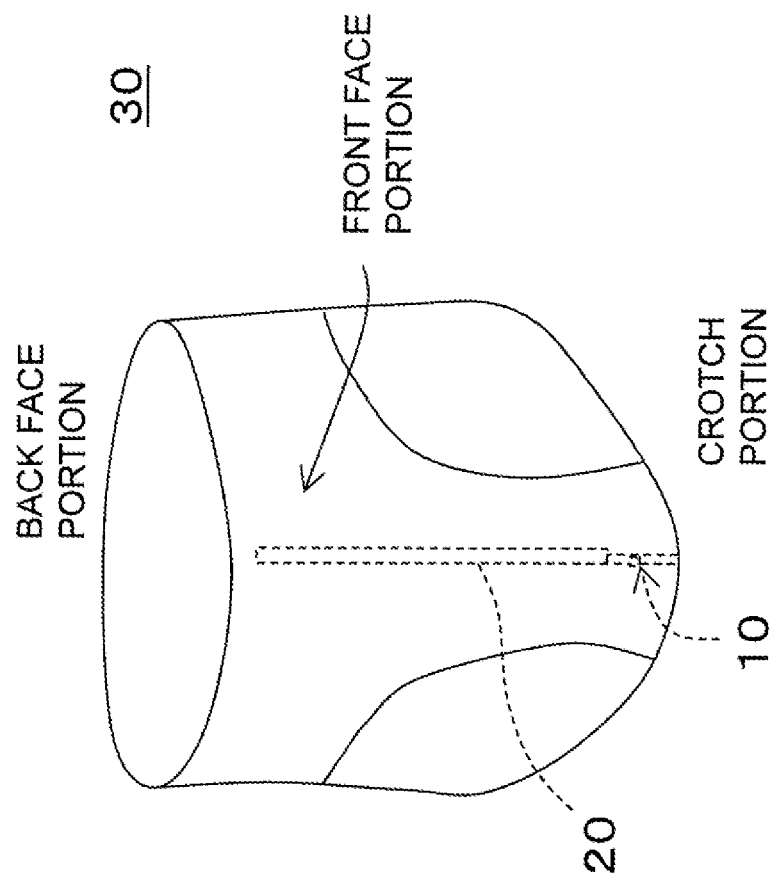
FIG. 2 is a schematic perspective diagram of the configuration of the diaper equipped with a moisture-detecting RFID tag of FIG. 1 in the case where the diaper is worn on a human body.

FIG. 1 is a diaper development diagram of the configuration of a diaper 30 equipped with a moisture-detecting RFID tag, according the first embodiment. The diaper 30 equipped with a moisture-detecting RFID tag is an example of the sanitary article equipped with a moisture-detecting RFID tag. The diaper 30 is an example of the sanitary article. FIG. 2 is a schematic perspective diagram of the configuration of the diaper 30 equipped with a moisture-detecting RFID tag of FIG. 1 in the case where the diaper 30 is worn on a human body. FIG. 3A is a sectional side diagram of the moisture-detecting RFID tag 10 used in the diaper 30 equipped with a moisture-detecting RFID tag, according to the first embodiment and FIG. 3B is a bottom diagram of FIG. 3A.

The diaper 30 equipped with a moisture-detecting RFID tag includes a moisture-absorptive material 34, a moisture-detecting RFID tag 10 disposed to be adjacent to the moisture-absorptive material 34, and a relay antenna 20 that is connected to the moisture-detecting RFID tag 10 and that relays an output of the moisture-detecting RFID tag 10. The moisture-detecting RFID tag 10 typically is an RFID tag that uses an electric-field antenna and includes, for example, a dipole antenna that includes an RFIC element 1 and antenna elements 11 and 12 each connected to the RFIC element 1. The moisture-detecting RFID tag 10 is configured to output a variation of the moisture amount included in the moisture-absorptive material 34 as a variation of the communication distance or the signal intensity originated from a variation of an electric length of each of the antenna elements, a variation of the capacitance between the antenna elements, or the like. The relay antenna 20 and the moisture-detecting RFID tag 10 may be, for example, capacitively coupled with each other. The diaper 30 includes a waterproof material 32 on the outer face side and the moisture-absorptive material 34 on the inner face side. The diaper 30 may have a gathering 36 disposed on an end portion of the moisture-absorptive material 34 to avoid any leakage of the moisture. Several sheets of the moisture-absorptive material 34 may be disposed being stacked on each other.

According to the diaper 30 equipped with a moisture-detecting RFID tag, the relay antenna 20 is included therein that is connected to the moisture-detecting RFID tag 10 and that is configured to extend the communication range such as the communication distance, the communication area, or the like by relaying the output of the moisture-detecting RFID tag 10. For example, when the moisture-detecting RFID tag 10 is arranged in the crotch portion of the diaper 30, the relay antenna 20 is extended to the front face portion. The output of the moisture-detecting RFID tag 10 can thereby be relayed by the relay antenna 20 to be able to extend the communication range up to the front face portion of the diaper 30. When the reader is applied to the front face portion of the diaper 30, the output passing through the relay antenna 20 can be detected by the reader without applying the reader to the crotch portion of the diaper 30. Thus, even when the moisture-detecting RFID tag 10 is arranged in the crotch portion of the diaper 30, the moisture can be detected without causing the person needing care to be conscious about or to be aware of the moisture detection even in the night time or the like, to be able to check any presence or absence of excretion.

The constituent elements of the sanitary article 30 equipped with a moisture-detecting RFID tag will be described below.

<Sanitary Article>

The sanitary article 30 is the diaper 30. The diaper may be either an all-in-one diaper or a diaper separable into an outer part and an inner part. The diaper may also be a diaper moisture-absorptive material, that is the inner part (or a pad) of the diaper separable into the outer part and the inner part. The diaper 30 may be any one of a baby diaper, incontinence underpants for an adult, an incontinence pad, care underpants, a care diaper, and the like. Moreover, the diaper 30 may further be a diaper for a pet. Otherwise, the diaper 30 may also be a diaper moisture-absorptive material that is the inner part of each of the above. The age and the sex of the user or the pet are not limited. The diaper only has to be formed using a material that absorbs moisture such as a cloth diaper and an unwoven-cloth diaper, and is not limited to a paper diaper.

The diaper 30 will be described herein as the sanitary article while the sanitary article is not limited to a diaper. The sanitary article may also be, for example, a menstrual sanitary article for women.

The moisture-detecting RFID tag 10 may be arranged on either the inner side or the outer side of an all-in-one diaper. For the diaper separable into the outer part and the inner part, the moisture-detecting RFID tag 10 may be arranged on any one of the inner side and the outer side of the inner part, and the inner side of the outer part. The relay antenna 20 only has to be connected to the antenna elements 11 and 12 of the moisture-detecting RFID tag 10 and may be arranged on either the inner side or the outer side of the diaper. For the diaper separable into the outer part and the inner part, the relay antenna 20 may be arranged on any one of the inner side and the outer side of the inner part, and the inner side and the outer side of the outer part.

Taking into consideration easiness of the alignment of the antenna elements 11 and 12 of the moisture-detecting RFID tag 10 and the relay antenna 20 with each other, it is preferred that the moisture-detecting RFID tag 10 and the relay antenna 20 be arranged on the outer side of the diaper and the moisture-detecting RFID tag 10 and the relay antenna 20 be capacitively coupled with each other. For the diaper separable into the outer part and the inner part, it is preferred that the moisture-detecting RFID tag 10 and the relay antenna 20 be arranged on the outer side of the inner part and these components be capacitively coupled with each other, that the moisture-detecting RFID tag 10 be arranged on the outer side of the inner part, the relay antenna be arranged on the inner side of the outer part, and these components be capacitively coupled with each other, that the moisture-detecting RFID tag 10 be arranged on the outer side of the inner part, the relay antenna be arranged on the outer side of the outer part, and these components be capacitively coupled with each other, that the moisture-detecting RFID tag 10 be arranged on the inner side of the outer part, the relay antenna 20 be arranged on the outer side of the outer part, and these components be capacitively coupled with each other, and the like.

<Moisture-Absorptive Material>

The moisture-absorptive material 14 is an element of the diaper 30 and can be a moisture-absorptive material having a high-molecular moisture-absorptive material or the like, for example. The moisture-detecting RFID tag 10 used in this case may be arranged between the plural moisture-absorptive materials 14 or between the waterproof material 32 and the moisture-absorptive material 14.

<Waterproof Material>

It should be appreciated that any material disposed to avoid any wetting of the outer face of the diaper 30 is usable as the waterproof material 32. For example, a polyolefin-based film, a polyolefin-based unwoven cloth, a polyester-based unwoven cloth, or the like can be used as the waterproof material 32.

<Moisture-Detecting RFID Tag>

The moisture-detecting RFID tag 10 is configured to output a variation of the communication distance or the signal intensity originated from a variation of a moisture amount included in the moisture-absorptive material 34. The moisture-detecting RFID tag 10 may be configured such that, for example, the communication distance or the signal intensity acquired after the moisture-absorptive material 34 absorbs moisture is smaller than the communication distance or the signal intensity acquired before the moisture-absorptive material 34 absorbs moisture. The moisture-detecting RFID tag 10 can be configured to discontinue its function due to its absorption of moisture and thus to discontinue any outputting therefrom. Otherwise, in contrast, the moisture-detecting RFID tag 10 can be configured such that the communication distance or the signal intensity acquired after the moisture-absorptive material 34 absorbs moisture is larger than the communication distance or the signal intensity acquired before the moisture-absorptive material 34 absorbs the moisture. In an exemplary aspect, the moisture-detecting RFID tag 10 only has to be, for example, an electromagnetic-field RFID tag. The moisture-detecting RFID tag 10 may be a one-terminal RFID tag or the like, in addition to the dipole RFID tag. The moisture-detecting RFID tag 10 only has to include, for example, the RFIC element 1, and the antenna elements 11 and 12 connected to the RFIC element 1.

With reference to FIGS. 3A and 3B, the moisture-detecting RFID tag 10 includes the RFIC element 1, an antenna element including a first and a second radiation electrodes 11 and 12, and a capacitor element formed between the first and the second radiation electrodes 11 and 12, and an opposite electrode 13. The RFIC element 1 includes a first input and output terminal 26a and a second input and output terminal 26b. The antenna elements 11 and 12 respectively include the first radiation electrode 11 connected to the first input and output terminal 26a and the second radiation electrode 12 connected to the second input and output terminal 26b. The radiation electrodes each form an electric field antenna that has one end as a feeding end and the other end as an open end. The capacitor element is connected in series between the feeding end of the first radiation electrode 11 and the feeding end of the second radiation electrode 12, and is connected in parallel to the RFIC element 1. The capacitor element includes the pair of capacitor electrodes (the first radiation electrode 11 and the opposite electrode 13, and the second radiation electrode 12 and the opposite electrode 13) and the moisture-absorptive material 14 inserted between the pair of capacitor electrodes. The moisture-detecting RFID tag 10 is configured to output a variation of the dielectric constant caused by absorption of moisture by the moisture-absorptive material 14 as a variation of the communication distance or the signal intensity.

According to the moisture-detecting RFID tag 10, the variation of the dielectric constant caused by the absorption of the moisture by the moisture-absorptive material 14 of the capacitor element can be output as the variation of the communication distance or the signal intensity. The state of the moisture absorption of the moisture-detecting RFID tag 10 can be learned, by detecting the variation of the communication distance or the signal intensity that corresponds to the reading distance. The tag 10 of the first embodiment separately has no expensive sensor element disposed therefrom such as a humidity sensor, and is a tag capable of detecting a variation of the moisture amount between the radiation electrodes as the variation of the communication distance or the signal intensity of the tag using the variation of the capacitance between the radiation electrodes that constitute an impedance matching circuit (described later) for the antenna elements and the RFIC element.

<RFIC Element>

Figure 4A:
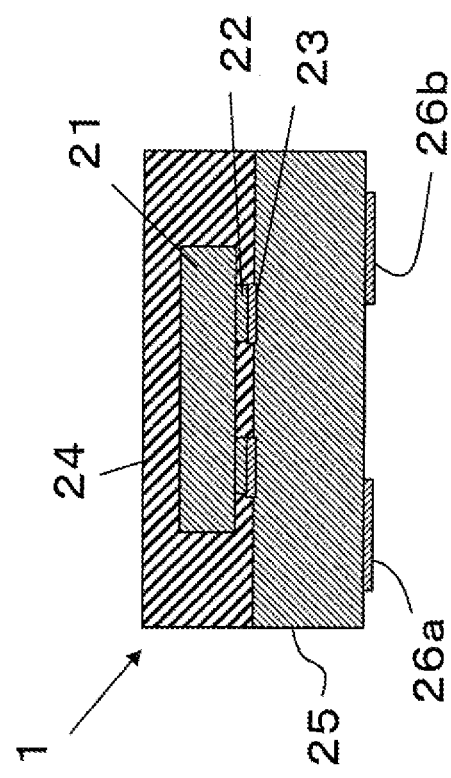
FIG. 4A is a schematic cross-sectional diagram of a cross-sectional structure of an RFIC element used in the moisture-detecting RFID tag of FIG. 3A
Figure 4B:
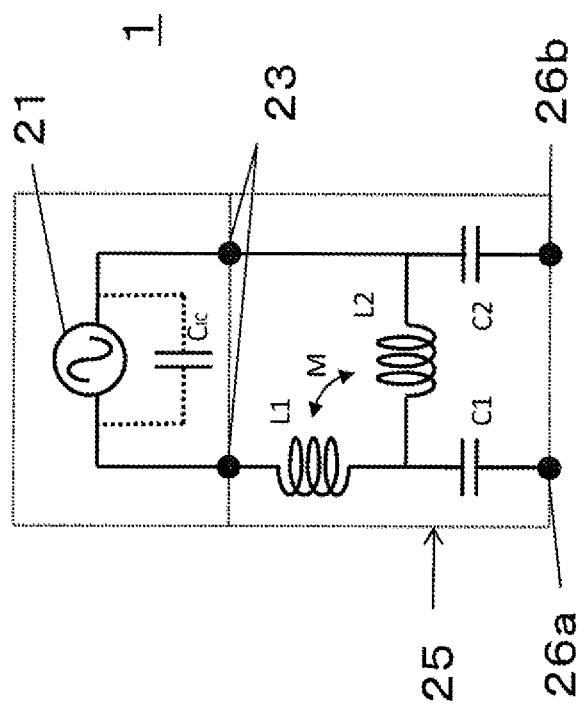
FIG. 4B is an equivalent circuit diagram of FIG. 4A.

FIG. 4A is a schematic cross-sectional diagram of a cross-sectional structure of the RFIC element 1 and FIG. 4B is an equivalent circuit diagram of FIG. 4A.

The RFIC element 1 is configured as an RFIC package including an RFIC chip 21 that processes an RFID signal and a multi-layered substrate 25 that has the RFIC chip 21 mounted thereon. The RFIC chip 21 has a memory circuit and a signal processing circuit incorporated therein (not shown) and may be sealed by a sealing resin 24 including an epoxy resin, or the like. The RFIC chip 21 is mounted on the multi-layered substrate 25 that forms a feeding circuit through a conductive joining material 22 and a terminal electrode 23. The feeding circuit may be formed in a multi-layered shape.

The multi-layered substrate 25 is a ceramic multi-layered substrate including a ceramic such as LTCC as its material, and has elements incorporated therein that form the feeding circuit such as inductor patterns constituting inductors L1 and L2, and capacitor patterns constituting capacitors C1 and C2. The inductor L1 and the inductor L2 have inductance values different from each other and are magnetically coupled with each other through a mutual inductance M. From the viewpoint of the equivalent circuit, the feeding circuit further includes a capacitor $C_{IC}$. The capacitor $C_{IC}$ is a floating capacitance of the RFIC chip 21 itself. The feeding circuit includes a resonant circuit that mainly includes the inductors L1 and L2, and the capacitor $C_{IC}$. The resonant frequency of this resonant circuit corresponds to the carrier frequency. Any significant variation of the central frequency of the carrier frequency can be avoided even when the electric lengths of the antenna elements including the first radiation electrode 11 and the second radiation electrode 12 are varied, by disposing the feeding circuit as above. The multi-layered substrate 25 is connected to the first radiation electrode 11 and the second radiation electrode 12 respectively through the terminal electrodes 26a and 26b.

<Antenna Element>

The antenna elements form a dipole antenna including the first radiation electrode 11 and the second radiation electrode 12. The first radiation electrode 11 and the second radiation electrode 12 are each connected to the RFIC element at the feeding end on the one end side thereof, each have the open end formed on the other end side thereof, and each extend from the RFIC element 1 in a direction opposite to that of each other. A capacitor element 16 is connected in series between the first radiation electrode 11 and the second radiation electrode 12 (see FIG. 5).

For example, in FIG. 3A, the RFIC element 1, the first radiation electrode 11, and the second radiation electrode 12 are each directly connected to the first input and output terminal 26a and the second input and output terminal 26b in a DC manner while the manner of the connection is not limited to this. For example, the RFIC element 1, and the first radiation electrode 11 and the second radiation electrode 12 can be coupled with each other by any one of capacitive coupling, magnetic-field coupling, and the like not employing the direct connection.

<Capacitor Element>

Figure 5:
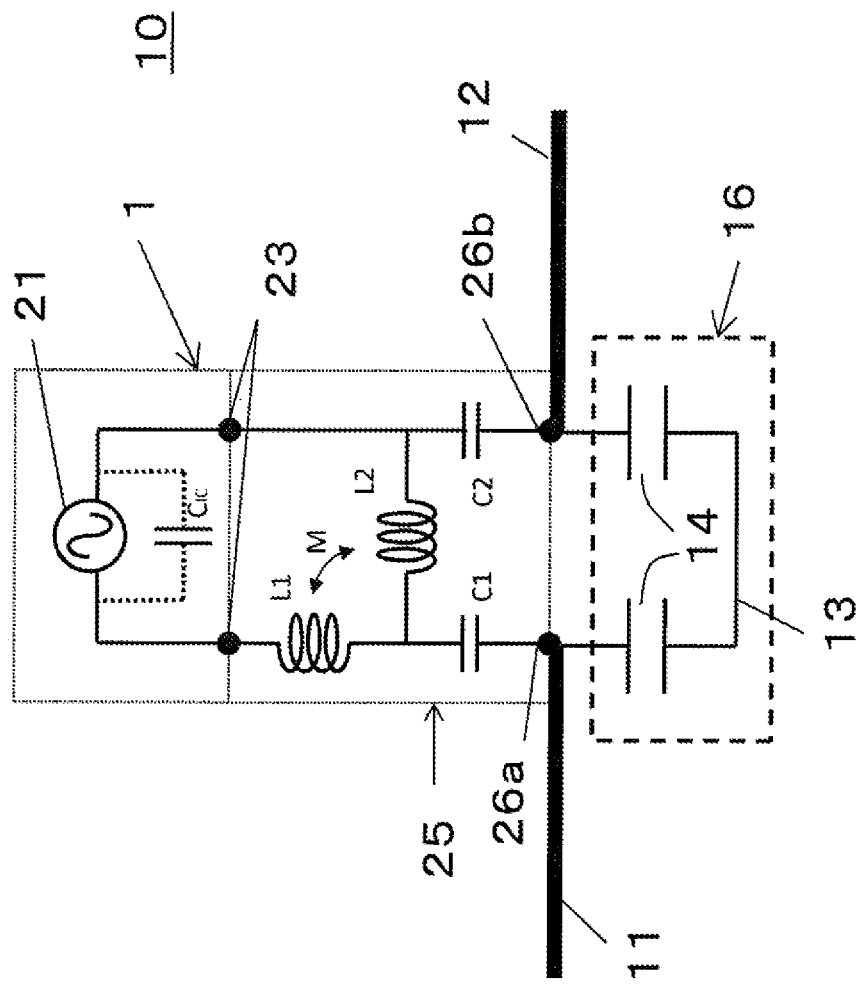
FIG. 5 is an equivalent circuit diagram as the overall moisture-detecting RFID tag of FIG. 3A.

FIG. 5 is an equivalent circuit diagram for the overall moisture-detecting RFID tag 10 according to the first embodiment.

As shown in the equivalent circuit diagram of FIG. 5, the capacitor element 16 is connected in series between the first radiation electrode 11 and the second radiation electrode 12, and is connected in parallel to the RFIC element 1. The capacitor element 16 includes a pair of capacitor electrodes and a moisture-absorptive material inserted between the pair of capacitor electrodes. The capacitor element 16 is a moisture-sensitive capacitor whose capacitance value is varied by the degree of moisture absorption of the moisture-absorptive material thereof. The capacitor element 16 is configured by disposing the opposite electrode 13 that is arranged to face at least a portion of each of the first radiation electrode 11 and the second radiation electrode 12. In this case, the pair of capacitor electrodes can be configured by the feeding end portion of the first radiation electrode 11 and the feeding end portion of the second radiation electrode 12, and the opposite electrode 13 that faces the feeding end portions of the radiation electrodes 11 and 12. For example, a first capacitor element can be configured by the first radiation electrode 11 and the opposite electrode 13. A second capacitor element can be configured by the second radiation electrode 12 and the opposite electrode 13. In this aspect, the first capacitor element and the second capacitor element form the capacitor element 16. Moreover, it should be appreciated that at least one capacitor element 16 only has to be present. The capacitor element 16 may separately be disposed from the antenna elements.

Together with the feeding circuit, the capacitor element 16 form a matching circuit to match the impedance between the RFIC element, and the first radiation electrode 11 and the second radiation electrode 12.

<Opposite Electrode>

The opposite electrode 13 is disposed to be arranged to face at least the portions of the first radiation electrode 11 and the second radiation electrode 12. For the opposite electrode 13, such material is usable as a copper foil, a copper plate, a copper-plated film, a gold foil, a gold plate, a gold-plated film, an aluminum foil, an aluminum plate, an aluminum film, a silver foil, a silver plate, or a silver plated-film that can be used in conventional electrodes, for example. Thus, the material is not limited to the above example and any conventional material can be used. The formation of the thin film and the like is not limited to plating and printing, vapor deposition, or the like may be used. The electrodes may each be configured using a conductive fiber. For example, the opposite electrode may be configured by vapor-depositing aluminum on a resin sheet or a resin film of polyethylene terephthalate (PET) or the like, as described in Examples described later, <Moisture-Absorptive Material>

In the exemplary aspect, the moisture-absorptive material 14 is continuously inserted between the first radiation electrode 11 and the opposite electrode 13 and between the second radiation electrode 12 and the opposite electrode 13. For example, a high-molecular moisture-absorptive material (a polymer-based moisture-absorptive material) or the like is usable as the moisture-absorptive material 14. An inorganic moisture-absorptive material is also usable. It is preferred that the degree of moisture absorption of the moisture-absorptive material be high. In this embodiment, the moisture-absorptive material 14 is continuously disposed between the first radiation electrode 11 and the opposite electrode 13 and between the second radiation electrode 12 and the opposite electrode 13 while the form of the insertion is not limited to this and moisture-absorptive materials may each be disposed separately from each other.

<Detection of State of Moisture Absorption>

Figure 6:
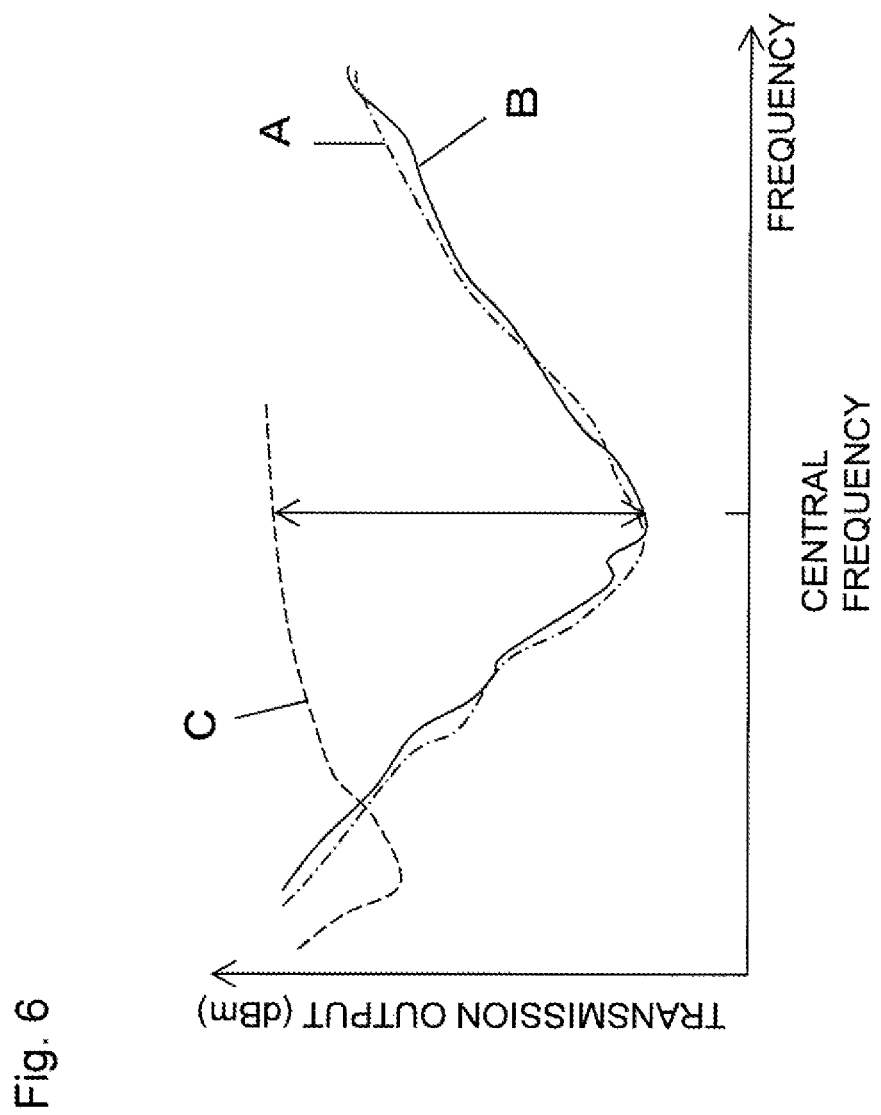
FIG. 6 is a graph of an example of the relation between the frequency and the transmission output acquired, before a capacitor element of the moisture-detecting RFID tag of FIG. 3A is disposed (A), after the capacitor element is disposed (B), and after a moisture-absorptive material absorbs moisture (C).

FIG. 6 is a graph of an example of the relation between the frequency and the transmission output acquired, before the capacitor element 16 of the moisture-detecting RFID tag 10 according to the first embodiment is disposed (A), after the capacitor element 16 is disposed (B), and after the moisture-absorptive material 14 absorbs moisture (C). The detection of the state of moisture absorption by the moisture-detecting RFID tag 10 will be described with reference to FIG. 6.

Even when the capacitor element 16 is not disposed, the moisture-detecting RFID tag 10 forms a matching circuit between the RFIC element 1 and the antenna elements including the first radiation electrode 11 and the second radiation electrode 12, and is adjusted such that the largest transmission output can be acquired at a predetermined frequency (FIG. 6:A). When the capacitor element 16 is disposed, the capacitor element 16 is formed for the antenna elements including the first radiation electrode 11 and the second radiation electrode 12. In this case, because the moisture-absorptive material 14 also has no moisture absorbed therein, no significant variation is observed in the relation between the frequency and the transmission output compared to that acquired before the capacitor element 16 is disposed (FIG. 6:B).

On the other hand, when the moisture-absorptive material 14 of the capacitor element 16 has moisture absorbed therein, the capacitance between the first radiation electrode 11 and the opposite electrode 13 and the capacitance between the second radiation electrode 12 and the opposite electrode 13 are each varied. As a result, the relation between the frequency and the transmission output is significantly varied after the moisture is absorbed compared to that acquired before the moisture is absorbed, and the transmission output at the predetermined frequency is therefore significantly reduced (FIG. 6:C). For example, in Example 1, described below, the transmission output is varied by 20 dBm or larger. In this case, any communication is unable between the moisture-detecting RFID tag 10 and a reader/writer (R/W). The state of the moisture absorption by the moisture-absorptive material 14 of the moisture-detecting RFID tag 10 can be detected by detecting the variation of the transmission output at the predetermined frequency. The relations (A, B, and C) between the frequency and the transmission output of FIG. 6 are the example and the relations are not limited to these.

FIG. 7A is a top diagram of another example (10a) of the moisture-detecting RFID tag used in the diaper 30 equipped with a moisture-detecting RFID tag, according to the first embodiment, FIG. 7B is a sectional side diagram of the cross-sectional configuration of FIG. 7A, and FIG. 7C is an equivalent circuit diagram of FIG. 7A.

The moisture-detecting RFID tag 10a of the other example includes the RFIC element 1, the first radiation electrode 11 and the second radiation electrode 12 that are connected to the RFIC element 1 and that each extend in a direction opposite to that of each other, and a moisture-absorptive material 2 that supports the first radiation electrode 11 and the second radiation electrode 12. The first radiation electrode 11 and the second radiation electrode 12 are each have a meander shape and include plural opposite portions 17 that can capacitively coupled with each other. The opposite portion 17 includes a pair of an element piece and an interval thereof that face each other in the antenna element. The moisture-absorptive material 2 is a base material sheet supporting the RFIC element 1, the first radiation electrode 11, and the second radiation electrode 12. As depicted in the equivalent circuit diagram of FIG. 7C, the RFID tag 10a includes the RFIC element 1, the first and the second radiation electrodes 11 and 12, and a capacitor 7. The capacitor 7 may be, for example, a pattern for the floating capacitance or the capacitor in the RFIC element 1.

Figure 8:
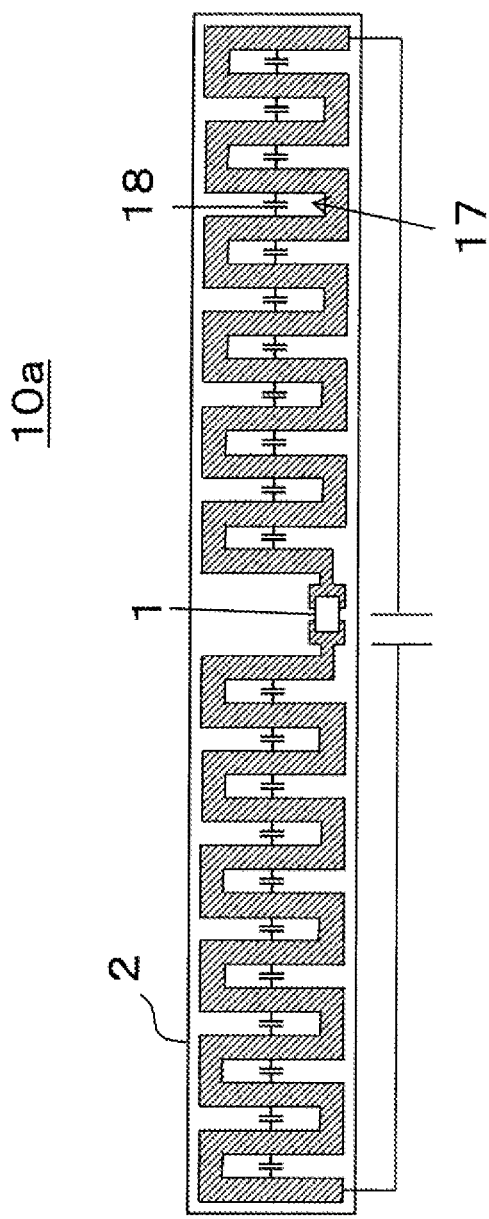
FIG. 8 is schematic diagram of capacitive coupling in the case where moisture is included in portions each sandwiched by meander-shaped portions of an antenna element of the moisture-detecting RFID tag of FIG. 7A.

FIG. 8 is a schematic diagram of capacitive coupling 18 in the case where moisture is included in each of the opposite portions 17 for the meander shapes of the first and the second radiation electrodes 11 and 12 of the moisture-detecting RFID tag 10a of FIG. 7A. Capacitance is also formed between the open ends.

As to the moisture-detecting RFID tag 10a depicted in FIG. 8, when the moisture-absorptive material 2 absorbs moisture, capacitive coupling 18 is generated between each two of the plural opposite portions 17 of the first radiation electrode 11 and the second radiation electrode 12, the floating capacitance is increased, and the electric length of each of the first and the second radiation electrodes 11 and 12 is varied. As a result, as depicted in FIG. 6, the communication distance is reduced, the state of the radio communication is varied, and the radio communication itself becomes unable. For example, when the base material sheet 2 is configured using a high-molecular moisture-absorptive material, the relative dielectric constant ε thereof with no moisture absorbed therein is about 5. The relative dielectric constant ε of the base material sheet 2 with moisture absorbed therein is about 60 in an exemplary aspect. As a result, the floating capacitance is increased in each of the plural opposite portions 17 for the meander shaped first and second radiation electrodes 11 and 12, and the length of the antenna is varied. The communication distance is therefore reduced, the state of the radio communication is varied, and the radio communication itself becomes unable. The presence of the moisture can be detected by detecting the variation of the state of the radio communication. Otherwise, even in the case where the base material sheet does not include any moisture-absorptive material, when the RFID tag 10a is inserted inside the diaper or is bonded to the outer layer of the diaper, the floating capacitance is also increased and the radio communication becomes unable to consequently enable the detection of the moisture.

FIG. 9A is a plan diagram of the configuration of yet another example (10b) of the moisture-detecting RFID tag used in the diaper 30 equipped with a moisture-detecting RFID tag, according to the first embodiment. FIG. 9B is a cross-sectional diagram seen from a B-B direction in FIG. 9A. The RFID tag 10b includes the RFIC element 1 that includes the first and the second input and output terminals 26a and 26b, and an antenna element that is connected to the first and the second input and output terminals 26a and 26b. The antenna element includes a radiation portion that includes a first radiation pattern 11 and a second radiation pattern 12, and a matching portion that includes a junctural pattern 3 that connects the first radiation pattern 11 and the second radiation pattern 12 to each other, and a first and a second connection patterns 4a and 4b that respectively branch from two points 8a and 8b distant from each other of the junctural pattern 3 and that respectively reach a first and a second end portions 5a and 5b respectively connected to the first and the second input and output terminals. The matching portion is a loop-shaped matching portion formed by the first connection pattern 4a, the second connection pattern 4b, and the junctural pattern 3. The RFID tag 10b has a configuration to have the loop-shaped matching portion between the two radiation patterns 11 and 12 constituting the dipole antenna, and the RFIC element 1. The first connection pattern 4a includes a turnback portion 9a that inverts the extension direction thereof, between the junctural pattern 3 and a first end portion 5a, and the second connection pattern 4b includes a turnback portion 9b that inverts the extension direction thereof, between the junctural pattern 3 and a second end portion 5b.

According to the RFID tag 10b, the first and the second connection patterns 4a and 4b branching from the junctural pattern 3 and connected to the RFIC element 1, respectively include the turnback portions 9a and 9b that each invert the extension direction thereof. When a stress is applied, the stress is thereby blocked by the junctural pattern 3 and the stress tends to avoid reaching the first and the second connection patterns 4a and 4b. Occurrence of any damage can therefore be suppressed at the connection points between the RFIC element and the antenna element. Even when a stress is applied associated with twist deformation or the like that is more significant than usual, the turnback portions 9a and 9b of the first and the second connection patterns 4a and 4b deform and the stress is thereby absorbed. The stress therefore tends to avoid reaching the first and the second end portions 5a and 5b that are the connection points thereof to the RFIC element 1, and occurrence of any damage can therefore be suppressed at the connection points between the RFIC element and the antenna element.

The moisture-detecting RFID tags 10, 10a, and 10b depicted in FIG. 3 to FIG. 9 are the examples and the moisture-detecting RFID tag is not limited to any one of these. No special RFID tag needs to be used as the moisture-detecting RFID tag. Any ordinarily usable moisture-detecting RFID tag is usable.

One or plural moisture-detecting RFID tag(s) may be arranged. When the plural moisture-detecting RFID tags are used, each of the moisture-detecting RFID tags 10 can also be read. Detection of the number of the excretion sessions and detection of the excretion position are enabled by arranging the plural moisture-detecting RFID tags side by side.

<Relay Antenna>

Figure 10B:
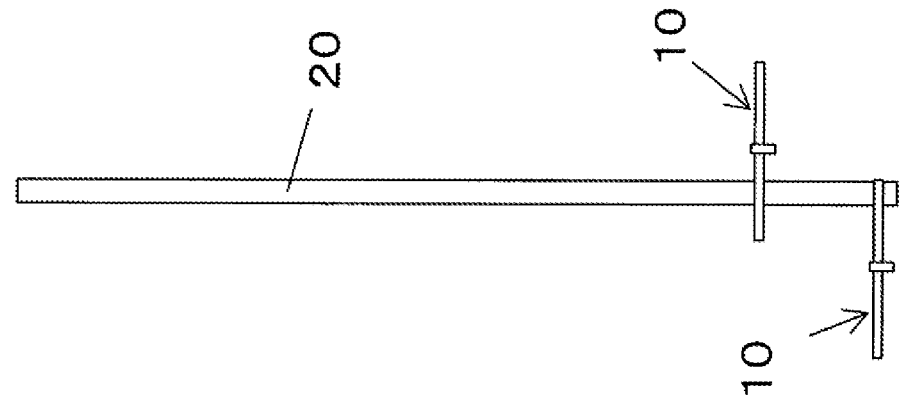
FIG. 10B is a diagram of an example where plural moisture-detecting RFID tags are connected to the relay antenna.
Figure 10A:
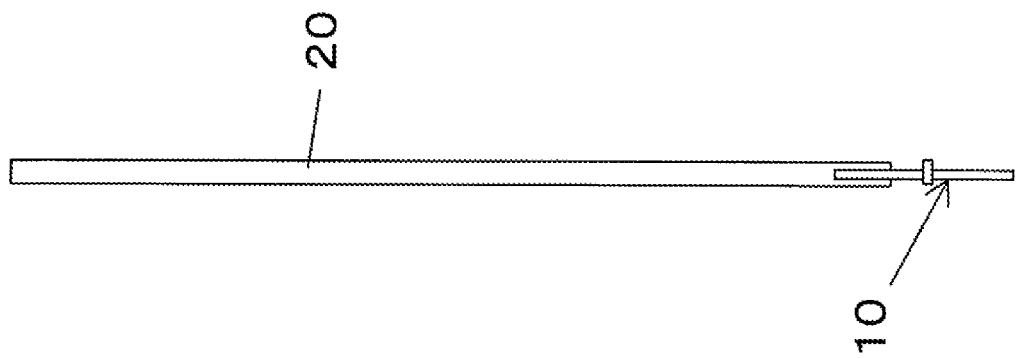
FIG. 10A is a diagram of an example of connection between a relay antenna and the moisture-detecting RFID tag that are used in the diaper equipped with a moisture-detecting RFID tag, according to the first embodiment

FIG. 10A is a diagram of an example of the connection between the relay antenna 20 and the moisture-detecting RFID tag 10 that are used in the diaper 30 equipped with a moisture-detecting RFID tag, according to the first embodiment. FIG. 10B is a diagram of an example where the plural moisture-detecting RFID tags 10 are connected to the relay antenna 20.

The relay antenna 20 is connected to the moisture-detecting RFID tags 10 and relays the outputs of the moisture-detecting RFID tag 10 to extend the communication range. The relay antenna 20 is extended from the crotch portion to the front face portion of the diaper 30. The relay antenna 20 may be extended from the crotch portion to the back face portion of the diaper 30. Otherwise, as described later, the relay antenna 20 may be extended from the back face portion to the front face portion of the diaper 30. Furthermore, the relay antenna 20 may be extended from the back face portion to the front face portion through the crotch portion of the diaper 30. The relay antenna 20 can execute the communication using the entirety thereof. The communication range in which the reader 40 can acquire a sufficient output can be disposed in a wide range by extending the relay antenna 20 along the face of the diaper 30.

It should be appreciated that the shape of the relay antenna 20 is not limited to a straight line shape and may be a curved line shape in alternative aspects. The relay antenna 20 is wound in the diaper 30 or around the diaper 30 and it is therefore preferred that the relay antenna 20 have a thin shape such as a plate-like shape, a thin plate-like shape, a mesh-like shape, or a foil-like shape while the shape is not limited to the above. For example, the shape may be a rod-like shape or a line-like shape.

The relay antenna 20 may be any relay antenna only when the relay antenna includes a conductive material that can radiate an electromagnetic wave. For example, such material is usable therein as a copper foil, a copper plate, a copper-plated film, a gold foil, a gold plate, a gold-plated film, an aluminum foil, an aluminum plate, an aluminum film, a silver foil, a silver plate, or a silver plated-film. The material is not limited to the above examples, and any ordinarily used material in antennas is usable as the material of the antenna. The formation of the antenna is not limited to plating and printing, vapor-deposition, or the like may be used. For example, the relay antenna 20 including a conductive ink may be formed on the outer face side of the diaper 30a using a printing crafting technique. The relay antenna may be configured using a conductive fiber. For example, the relay antenna may be configured by vapor-depositing aluminum onto a resin sheet or a resin film of polyethylene terephthalate (PET) or the like.

As depicted in FIGS. 10A and 10B, the direction of the insertion of the moisture-detecting RFID tag 10 relative to the relay antenna 20 may be at any direction only when the moisture-detecting RFID tag 10 and the relay antenna 20 overlap with each other. It is preferred that the relay antenna 20 be disposed in the vicinity of the open end portion of one radiation electrode of the first radiation electrode and the second radiation electrode that constitute the dipole antenna. Especially, it is preferred that the relay antenna 20 be capacitively coupled with the open end portion. It its noted that one or alternatively a plurality of moisture-detecting RFID tag(s) 10 may be arranged to be connected to one relay antenna 20. The connection between the moisture-detecting RFID tag 10 and the relay antenna 20 may be either the direct connection or the capacitive connection. For example, the capacitively-coupling relay antenna 20 may be attached on the outer face side of the diaper 30 or in the exterior of the diaper 30 (including the diaper cover, the clothes, and the like) such that the relay antenna 20 overlaps with the moisture-detecting RFID tag 10 inserted on the inner face side of the diaper 30.

The portion of the relay antenna 20 to overlap with the moisture-detecting RFID tag 10 may be set to have a large area such that the moisture-detecting RFID tag 10 and the relay antenna 20 easily overlap with each other. The moisture-detecting RFID tag 10 and the relay antenna 20 may be set to intersect each other such that the moisture-detecting RFID tag 10 and the relay antenna 20 easily overlap with each other.

<Relaying of Output of Moisture-Detecting RFID Tag by Relay Antenna>

The condition will be described for the relaying of the output of the moisture-detecting RFID tag 10 by the relay antenna 20.

Figure 12:
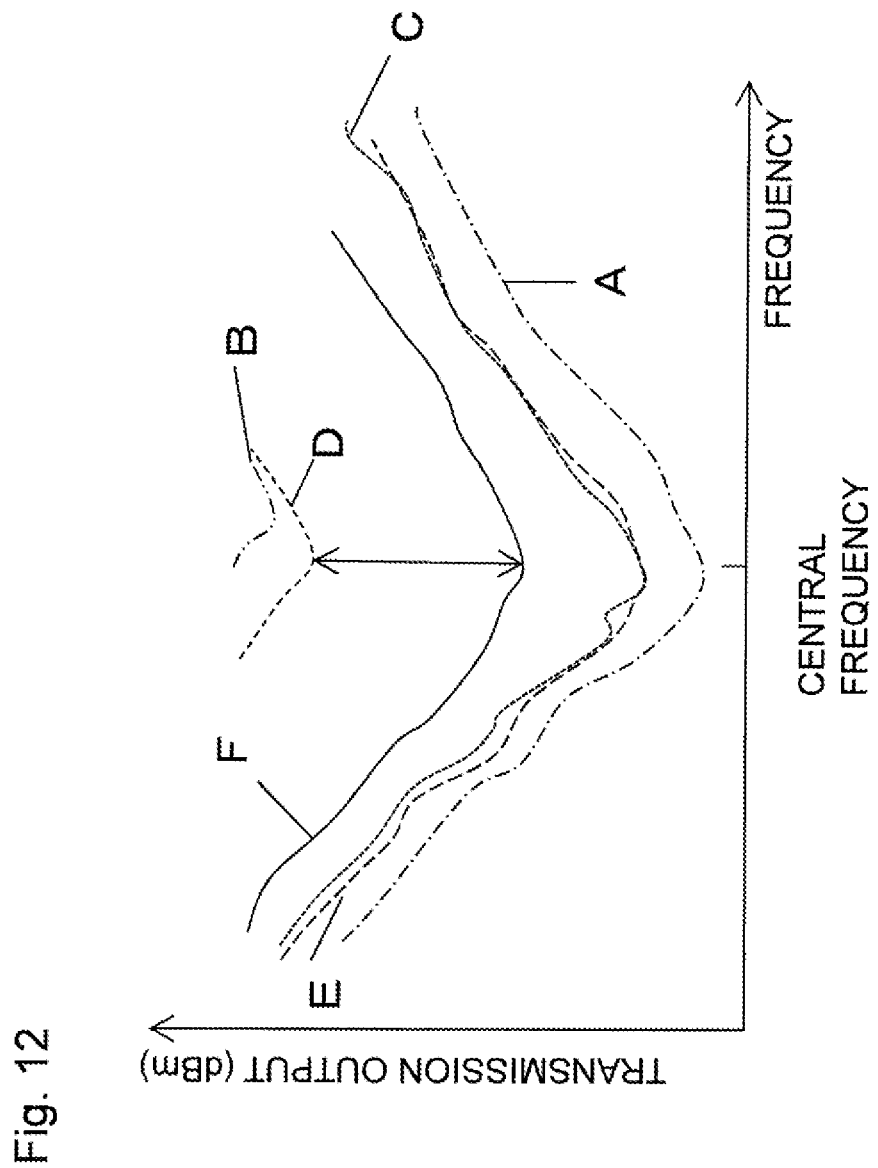
FIG. 12 is a graph of the relation between the frequency and the transmission output of the communication with the moisture-detecting RFID tag of each of the states (A to F) of FIG. 11.

FIG. 11A is a schematic perspective diagram of the case (A) where the communication by the reader 40 is executed in the vicinity of the moisture-detecting RFID tag 10 alone and the case (B) where the communication by the reader 40 is executed at a distance d corresponding to the distance between the crotch portion and the front face portion of the diaper. FIG. 11B is a schematic perspective diagram of the case (C) where the communication by the reader 40 is executed in the vicinity of the lone moisture-detecting RFID tag 10 inserted into the crotch portion of a diaper 50 and the case (D) where the communication by the reader 40 is executed in the front face portion of the diaper 50 that is distant from the crotch portion of the diaper 50 by a distance d. FIG. 11C is a schematic perspective diagram of the case (E) where the communication by the reader 40 is executed in the vicinity of the moisture-detecting RFID tag 10 inserted into the crotch portion of the diaper 30 equipped with a moisture-detecting RFID tag, according to the first embodiment and the case (F) where the communication by the reader 40 is executed in the front face portion of the diaper 30 that is distant from the crotch portion of the diaper 50 by the distance d. FIG. 12 is a graph of the relation between the frequency and the transmission output in the communication with the moisture-detecting RFID tag 10 of each of the cases (A to F) of FIG. 11.

(a) As depicted in FIG. 11A and FIG. 12, in the case (A) where the communication by the reader 40 is executed in the vicinity of the moisture-detecting RFID tag 10 alone, a high transmission output was acquired at the central frequency of the communication. On the other hand, in the case (B) where the communication is executed at the distance corresponding to the distance between the crotch portion and the front face portion of the diaper, substantially no transmission output was acquired.

(b) As depicted in FIG. 11B and FIG. 12, the case (C) where the communication is executed in the vicinity of the lone moisture-detecting RFID tag 10 inserted into the crotch portion of the diaper 50, a high transmission output was acquired at the central frequency of the communication. On the other hand, in the case (D) where the communication is executed in the front face portion of the diaper 50, substantially no transmission output was acquired.

(c) As depicted in FIG. 11C and FIG. 12, in the case (E) where the communication is executed in the vicinity of the moisture-detecting RFID tag 10 inserted into the crotch portion of the diaper 30 equipped with a moisture-detecting RFID tag, according to the first embodiment, a high transmission output was acquired at the central frequency of the communication. On the other hand, in the case (F) where the communication is executed in the front face portion of the diaper 30, a relatively high transmission output was also acquired. A transmission output was acquired that was higher by, for example, about 10 dBm than that in the case (D) where the lone moisture-detecting RFID tag 10 is inserted into the crotch portion of the diaper 50 and the communication is executed in the front face portion of the diaper 50.

As above, the output of the moisture-detecting RFID tag 10 can be relayed by the relay antenna 20. In the above, compared to the cases (B and D) where the relay antenna 20 is not disposed, in the case (F) where the relay antenna 20 is disposed, the high transmission output was acquired even in the front face portion that is distant from the crotch portion having the moisture-detecting RFID tag 10 arranged therein. The relay antenna 20 functions as an auxiliary antenna or a repeater to extend the communication distance or the communication area of the moisture-detecting RFID tag 10. The output from the moisture-detecting RFID tag 10 passing through the relay antenna 20 can highly sensitively be detected and presence or absence of any excretion can be checked.

<Intersectional Position for Relay Antenna and Moisture-Detecting RFID Tag>

Figures 13A, 13B:
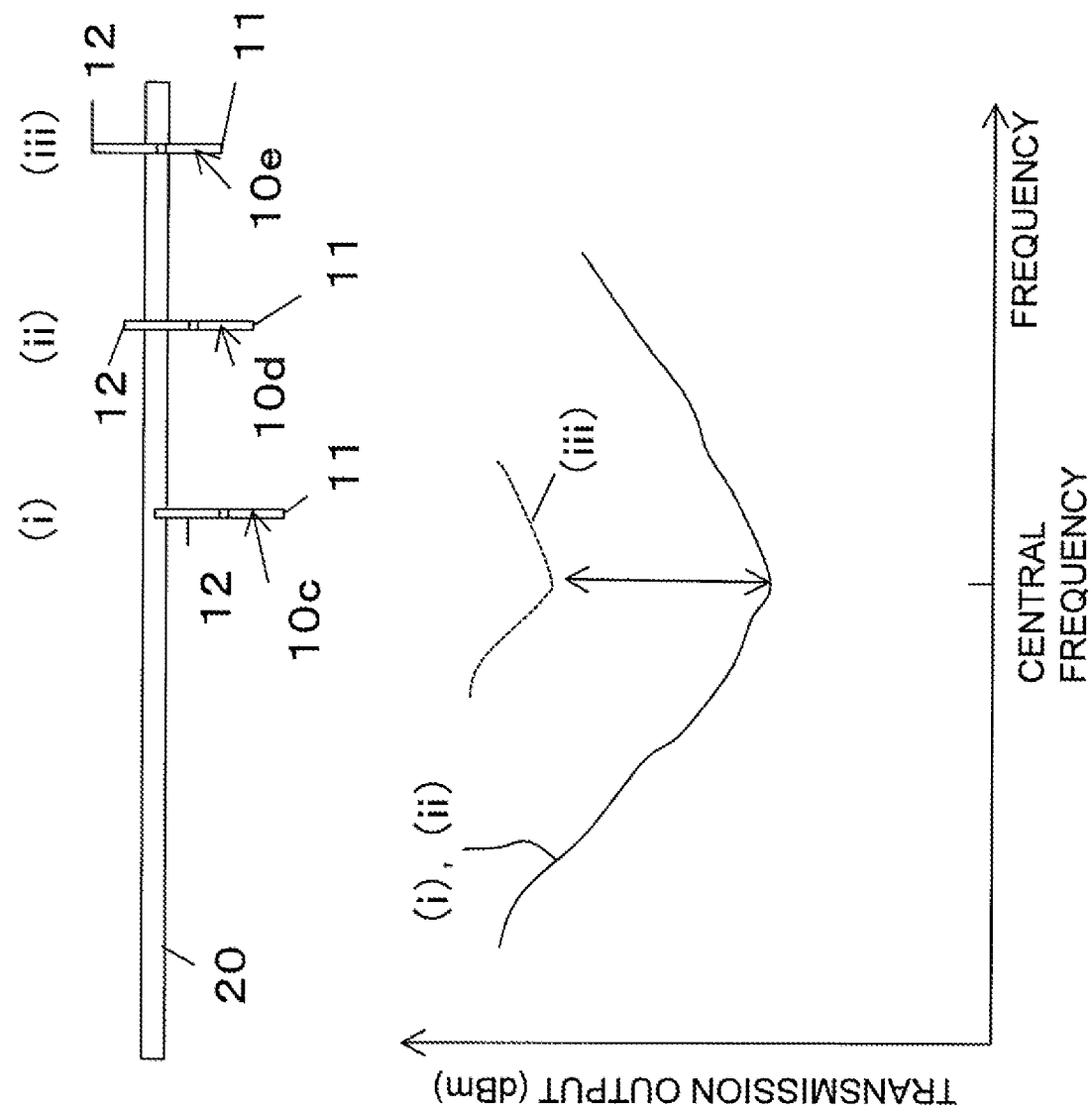
FIG. 13A is a schematic diagram of an example of an intersectional position for the relay antenna and the antenna of the moisture-detecting RFID tag in the diaper equipped with a moisture-detecting RFID tag and FIG. 13B is a graph of the relation between the frequency and the transmission output in the communication of both of the antennas of FIG. 13A with the moisture-detecting RFID tag in each of the arrangement examples thereof.

FIG. 13A is a schematic diagram of an example of the intersectional position for the relay antenna 20 and the antenna of each of moisture-detecting RFID tags 10c, 10d, and 10e in the diaper 30 equipped with a moisture-detecting RFID tag. FIG. 13B is a graph of the relation between the communication frequency and the transmission output acquired with the moisture-detecting RFID tag at the intersectional positions ((i), (ii), and (iii)) for the antennas of FIG. 13A.

As depicted in FIG. 13B, with the first radiation electrodes 11 of the moisture-detecting RFID tags 10c and 10d, and the relay antenna 20, substantially equal intensities of transmission output were acquired ((i) and (ii)) regardless of the intersectional positions. On the other hand, with the moisture-detecting RFID tag 10e, only a low transmission output was acquired ((iii)) because the connection portions between the RFIC element 1, and the first radiation electrode 11 and the second radiation electrode 12 intersect the relay antenna 20. When the relay antenna 20 is connected to the connection portions between the RFIC element 1, and the first radiation electrode 11 and the second radiation electrode 12 of the moisture-detecting RFID tag 10e, no effect of relaying any output by the relay antenna 20 was acquired. The output was reduced by, for example, about 10 dBm.

Based on the above, it turned out that the intersectional position for the relay antenna and the antenna of the moisture-detecting RFID tag only had to avoid overlapping with the connection portion between the RFIC element 1, and the first radiation electrode 11 and the second radiation electrode 12 of the moisture-detecting RFID tag.

<Projection Amount of Relay Antenna from Moisture-Detecting RFID Tag>

Figure 14A:
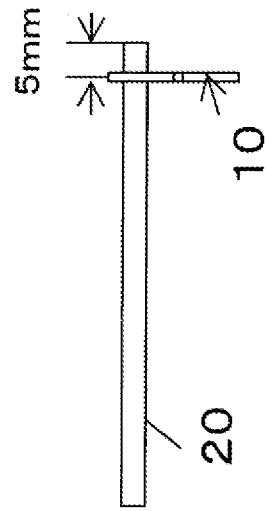
FIG. 14A is a schematic diagram of an example of a projection amount of the relay antenna from the moisture-detecting RFID tag of the diaper equipped with a moisture-detecting RFID tag.
Figure 14B:
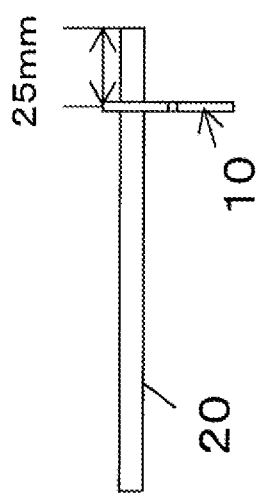
FIG. 14B is a schematic diagram of another example of the projection amount of the relay antenna from the moisture-detecting RFID tag.
Figure 14C:
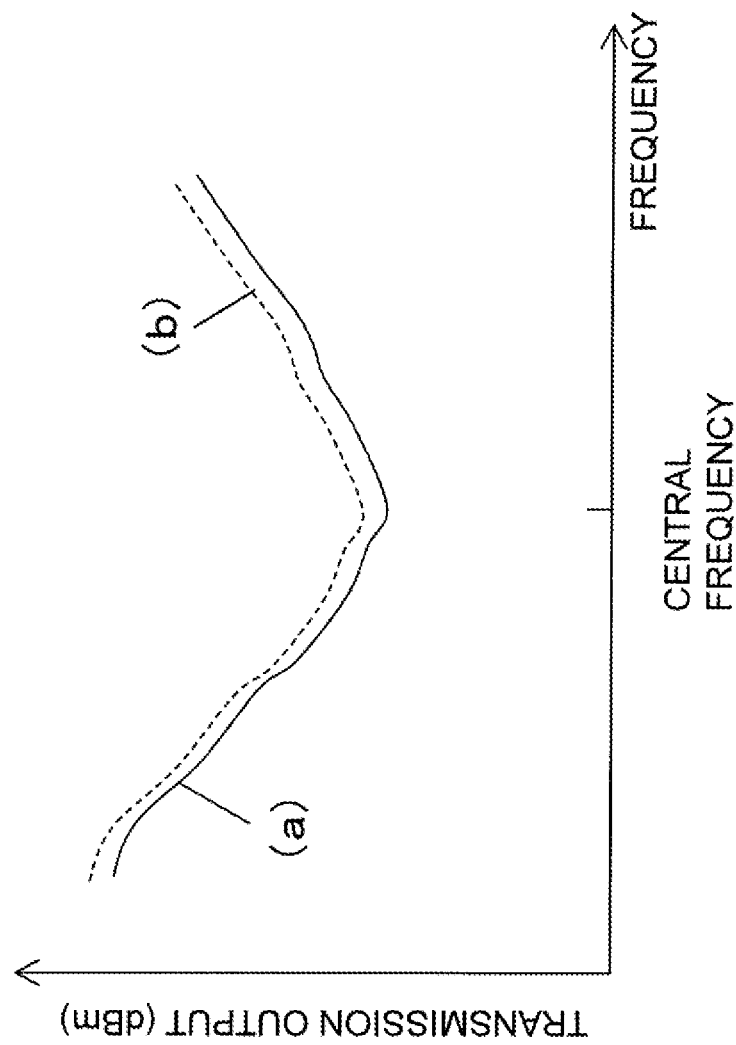
FIG. 14C is a graph of the relation between the frequency and the transmission output in the communication with the moisture-detecting RFID tag for the example and the other example of the projection amount of the relay antenna from the moisture-detecting RFID tag of FIGS. 14A and 14B.

FIG. 14A is a schematic diagram of an example of a projection amount of the relay antenna from the moisture-detecting RFID tag of the diaper equipped with a moisture-detecting RFID tag. FIG. 14B is a schematic diagram of another example of the projection amount of the relay antenna from the moisture-detecting RFID tag. FIG. 14C is a graph of the relation between the frequency and the transmission output in the communication with the moisture-detecting RFID tag for the example and the other example of the projection amount of the relay antenna from the moisture-detecting RFID tag of FIG. 14A and FIG. 14B.

As depicted in FIG. 14C, no significant variation of the relation is present between the projection amounts of the case (a) of 25 mm and the case (b) of 5 mm, of the relay antenna 20 from the moisture-detecting RFID tag. The projection amount of the relay antenna 20 therefore does not need to be taken into consideration.

<Width of Relay Antenna>

Figure 15A:
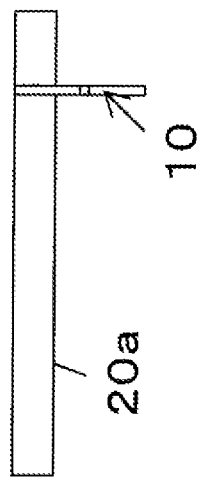
FIG. 15A is a schematic diagram of an example of the arrangement of the relay antenna for the moisture-detecting RFID tag in the diaper equipped with a moisture-detecting RFID tag.
Figure 15B:
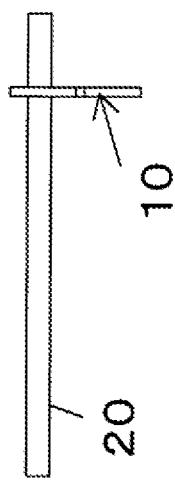
FIG. 15B is a schematic diagram of an example of the arrangement of the relay antenna for the moisture-detecting RFID tag in the case where the width of the relay antenna is set to be larger than that of FIG. 15A.
Figure 15C:
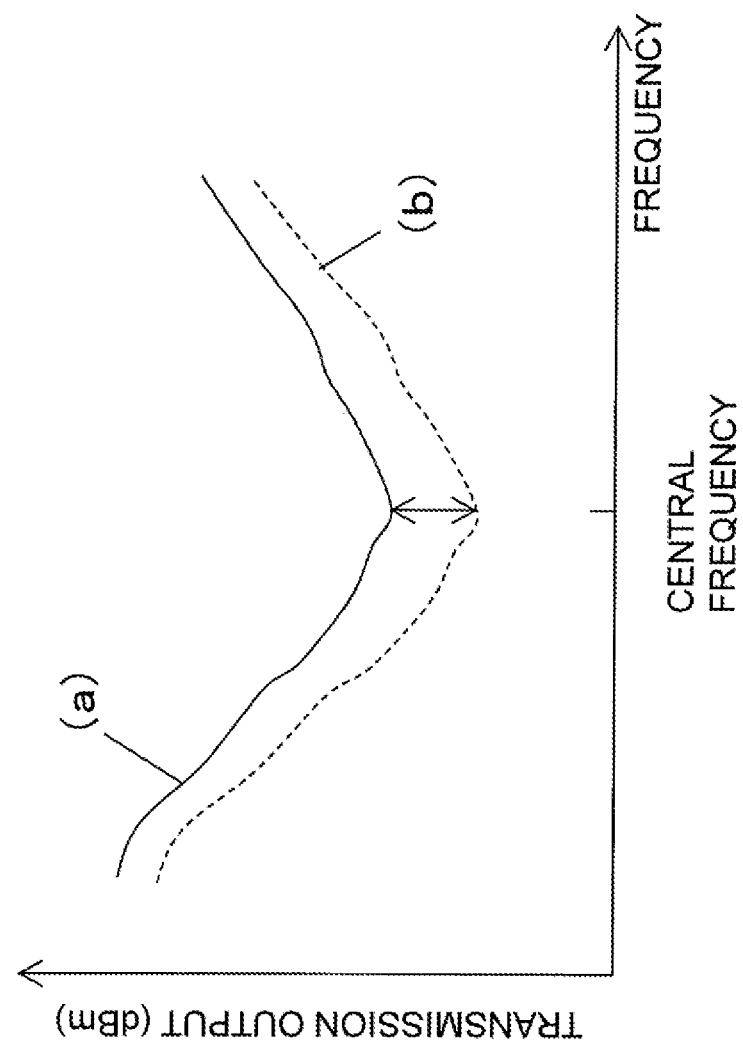
FIG. 15C is a graph of the relation between the frequency and the transmission output in the communication with the moisture-detecting RFID tag of the arrangement examples of FIGS. 15A and 15B.

FIG. 15A is a schematic diagram of an example of the arrangement of the relay antenna 20 (having a width of 5 mm) for the moisture-detecting RFID tag 10 in the diaper equipped with a moisture-detecting RFID tag. FIG. 15B is a schematic diagram of an example of the arrangement of a relay antenna 20a for the moisture-detecting RFID tag in the case where the width of the relay antenna 20a (having a width of 10 mm) is set to be larger than that of FIG. 15A. FIG. 15C is a graph of the relation between the frequency and the transmission output in the communication with the moisture-detecting RFID tag of the arrangement examples of FIG. 15A and FIG. 15B.

As depicted in FIG. 15C, when the width of the relay antenna was increased (b), the transmission output was increased compared to that of the case where the width was small (a). It is preferred that the width of the relay antenna be set to be wide.

Even with the relay antenna 20*a* (having the width of 10 mm), a practically usable transmission output was able to be acquired.

The above results were compared with each other under the same condition for the intersectional position for the moisture-detecting RFID tag 10 and the relay antenna 20.

<Method of Changing Diaper>

FIG. 16 is a flowchart of diaper changing in the case where the diaper 30 equipped with a moisture-detecting RFID tag of FIG. 1 is used.

(1) The person needing care him/herself or the caretaker causes the person needing care to wear the diaper 30 (S11).

(2) When a regular round is made to change the diaper, the caretaker executes reading of the moisture-detecting RFID tag 10 for the diaper 30 of the person needing care using, for example, a smartphone-combined reader 40 formed by incorporating a reader device into a communication terminal such as a smartphone, that is arranged at a specific distance (S12). The reader 40 is not limited to the smartphone-combined reader and may be a standing reader or a handheld reader that is not the smartphone-combined reader. Types of standing reader also include the one to be matted under the body of the lying person needing care like a sheet or a futon-mat. Otherwise, a mechanism may be employed according to which a small including a battery and having a function of communicating with an external network is attached to the diaper or the clothes, the person needing care thereby always wears the small unit, and the state is always monitored at specific intervals.

(3) After wearing the diaper, it is determined whether a time period equal to a prescribed time period or longer elapses (S13). When it is determined that the time period equal to the prescribed time period or longer elapses, the caretaker removes the diaper 30 of the person needing care (S14) and the person needing care wears a new diaper 30 having the moisture-detecting RFID tag 10 attached thereto or the caretaker causes the person needing care to wear (S15). Thereafter, the procedure returns to the reading of the moisture-detecting RFID tag 10 (S12).

When it is determined that the time period equal to the prescribed time period or longer does not elapse, the procedure moves to step S16 to be executed next.

In general, any diaper rash, bed sore, and the like can be prevented by changing the diaper in response to the time period elapsing after wearing the diaper, as above. For example, in the case where a diaper capable of executing plural absorption sessions is used, when the amount of the excreted urine is small, the urine adhering to the diaper touches the body for a long time period and may cause the bed sore and the like. In the case where any urine is not guided to the portion of the tag due to the posture, where the tag is accidentally detached, or the like, any urine can also be prevented from leaking onto the bed and the like by urging the change of the diaper by setting the prescribed time period.

(4) It is determined whether the signal intensity of the communication with the moisture-detecting RFID tag 10 is equal to a threshold value or higher (S16). When it is determined that the signal intensity is equal to the threshold value or higher (YES), this indicates that the moisture-absorptive material 14 of the moisture-detecting RFID tag 10 has no moisture absorbed therein. This means that any moisture is not yet present in the diaper 30 and the diaper is not changed (S17) and the procedure returns to the reading of the moisture-detecting RFID tag 10 executed when the regular round is made (S12).

On the other hand, when it is determined that the signal intensity of the communication with the moisture-detecting RFID tag 10 is lower than the threshold value (NO), it can be considered that the moisture-absorptive material 14 has absorbed moisture therein. In this case, a significant amount of moisture, that is, a significant amount of urine, solid waste, or the like is determined to be present in the diaper 30. The procedure moves to step S18.

(5) The caretaker removes the diaper 30 from the person needing care (S18) and the person needing care wears a new diaper 30 having the moisture-detecting RFID tag 10 attached thereto or the caretaker causes the person needing care to wear the diaper (S19).

(6) The reading of the moisture-detecting RFID tag 10 is executed by the reader 40 arranged at a specific distance relative to the diaper 30 immediately after changing the diaper (S20). The procedure thereafter moves to step S16 at which it is determined whether the signal intensity in the communication with the moisture-detecting RFID tag 10 is equal to the threshold value or higher. Any initial failure of the moisture-detecting RFID tag 10 can be detected by executing the reading of the moisture-detecting RFID tag 10 immediately after changing the diaper as above.

The procedure may return to the reading of the moisture-detecting RFID tag 10 executed when the regular round is made (S12) without executing the reading of the moisture-detecting RFID tag 10 executed immediately after the diaper is changed (S20). The reading of the moisture-detecting RFID tag 10 executed immediately after the diaper is changed may not be executed.

According to the above, the diaper can be changed by making the regular round using the smartphone-combined reader 40. According to the flowchart, the necessary number of diaper change sessions can repeatedly be executed in accordance with the actual state.

In this embodiment, the state of the variation of the state of the radio communication is detected by determining whether the signal intensity from the moisture-detecting RFID tag 10 is equal to the threshold value or higher. The state of the moisture absorption is thereby detected. The threshold value corresponding to the signal intensity for the acceptable amount only has to be set such that the diaper is changed when the acceptable amount is reached. The state of the wetness of the diaper 30 can more properly be understood and whether the diaper needs to be changed can more reliably be determined. For example, when the state of the moisture in the diaper 30 is displayed, the state of the wetness of the diaper 30 may be displayed by digitalizing or visualizing the state. For example, the state of the wetness of the diaper 30 may be displayed using plural colors such as yellow and red to facilitate the understanding of the necessity of changing the diaper.

In this embodiment, the case has been described where the moisture-detecting RFID tag 10 is configured such that the communication distance or the signal intensity after the moisture-absorptive material 14 absorbs any moisture is smaller than the communication distance or the signal intensity before the moisture-absorptive material 14 absorbs the moisture. Not limiting to this case, the case may be employed, for example, where, in contrast, the moisture-detecting RFID tag 10 is configured such that the communication distance or the signal intensity after the moisture-absorptive material 14 absorbs any moisture is larger than the communication distance or the signal intensity before the moisture-absorptive material 14 absorbs the moisture.

It is noted that the series of steps S13 to S15 to determine whether the time period equal to the prescribed time period or longer elapses after wearing the diaper are not essential and may be executed when necessary.

Second Embodiment

<Diaper Equipped with Moisture-Detecting RFID Tag>

Figure 17:
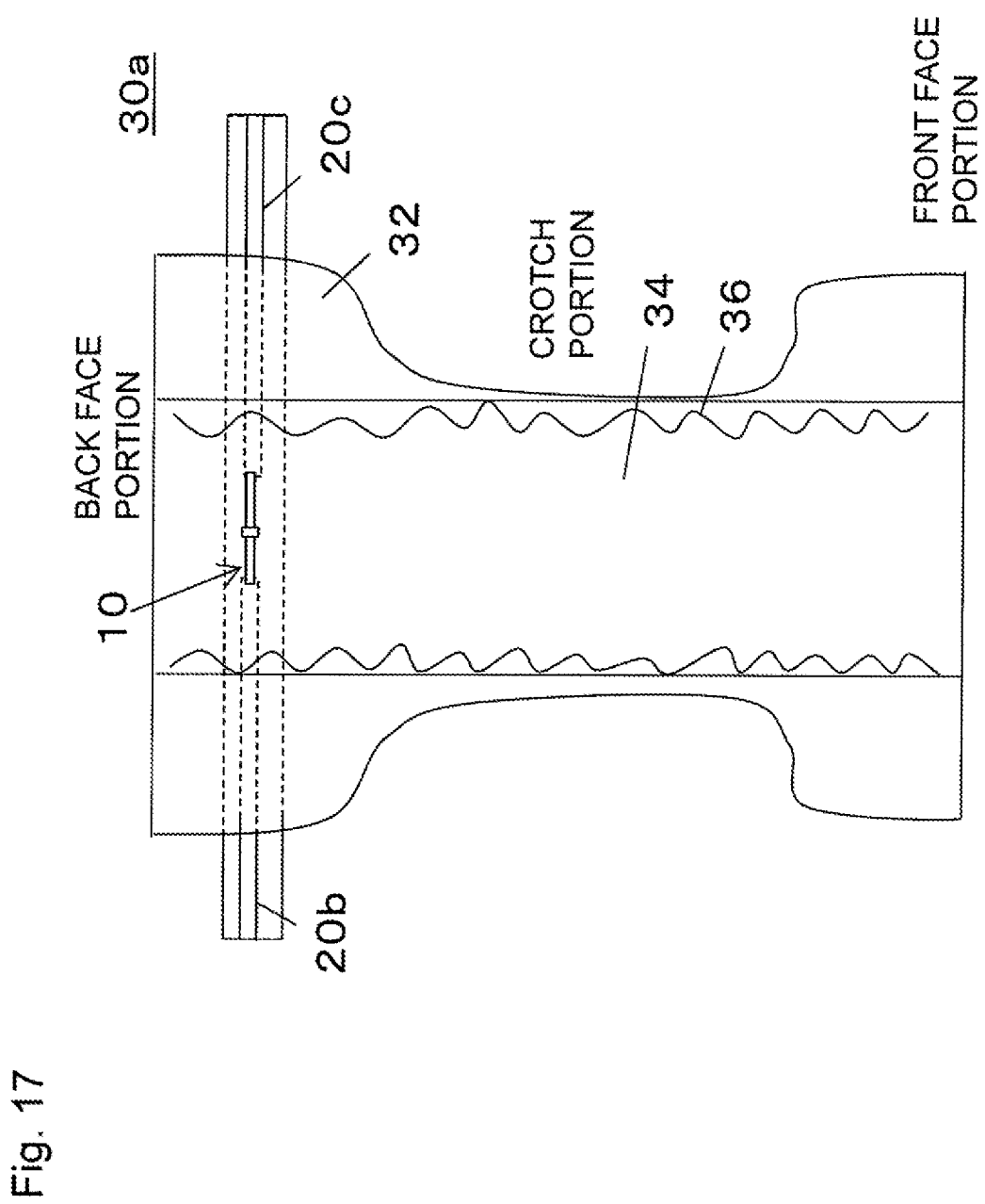
FIG. 17 is a diaper development diagram of the configuration of a diaper equipped with a moisture-detecting RFID tag, according to a second embodiment.
Figure 18:
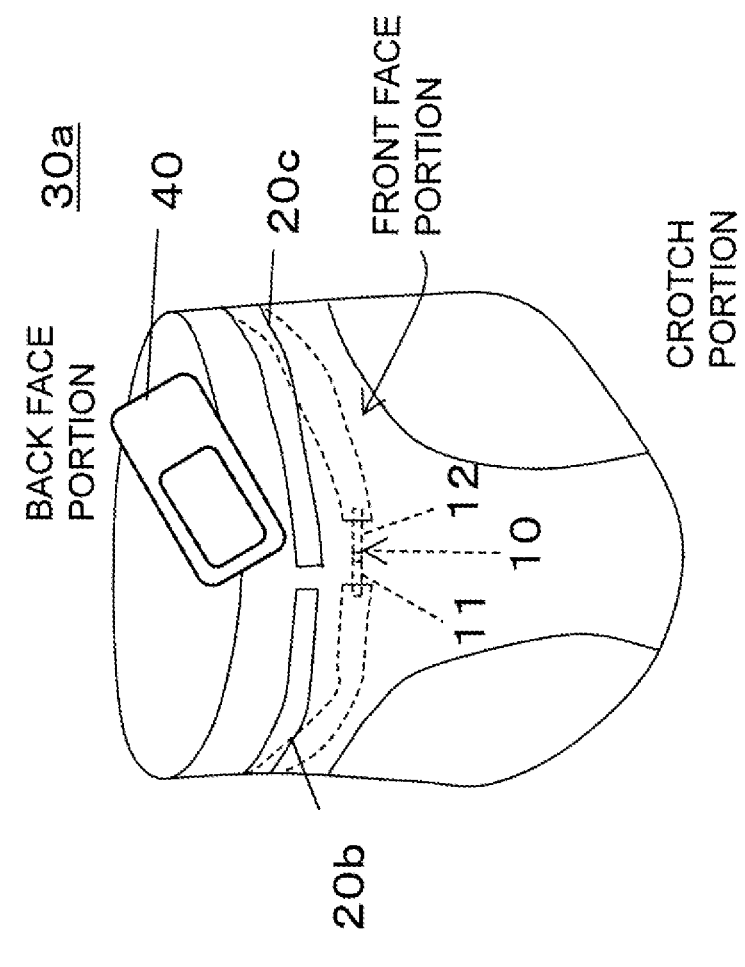
FIG. 18 is a schematic perspective diagram of the configuration of the diaper equipped with a moisture-detecting RFID tag of FIG. 17 in the case where the diaper is worn on a human body.

FIG. 17 is a diaper development diagram of the configuration of the diaper 30*a* equipped with a moisture-detecting RFID tag, according to a second embodiment. FIG. 18 is a schematic perspective diagram of the configuration of the diaper 30*a* equipped with a moisture-detecting RFID tag of FIG. 17 in the case where the diaper 30*a* is worn on a human body.

Compared to the diaper equipped with a moisture-detecting RFID tag according to the first embodiment, the diaper 30*a* equipped with a moisture-detecting RFID tag differs therefrom in that the moisture-detecting RFID tag 10 is not arranged in the crotch portion (the excretion portion) of the diaper 30*a* but is arranged in the back face portion on the inner side of the diaper 30*a*. The diaper 30*a* also differs therefrom in that relay antennas 20*b* and 20*c* are respectively connected to the first radiation electrode 11 and the second radiation electrode 12 of the moisture-detecting RFID tag 10 from the outer side of the diaper 30*a* through the diaper 30. The diaper 30*a* further differs therefrom in that the relay antennas 20*b* and 20*c* are extended from points in the circumference of the human waist along the hips to be from the back face portion on the outer side of the diaper 30*a* to the front face portion thereof. The diaper 30*a* equipped with a moisture-detecting RFID tag is configured as an all-in-one diaper that includes the relay antennas 20*b* and 20*c*. As depicted in FIG. 18, the relay antenna 20*c* is arranged from a point in the circumference of the waist in the back face portion along the hips while the arrangement is not limited to this. For example, the relay antenna 20*c* may also be arranged along the circumference of the waist on the back face side.

According to the diaper 30*a* equipped with a moisture-detecting RFID tag, the output passing through the relay antennas 20*b* and 20*c* can be detected by applying the reader 40 to the front face portion of the diaper 30*a* without applying the reader 40 to the back face portion of the diaper. The moisture can be detected without changing the posture of the person needing care even when the moisture-detecting RFID tag 10 is arranged in the back face portion on the inner side of the diaper 30*a*. For example, even when the person needing care takes a posture of lying on the person's side, the relay antennas 20*b* and 20*c* passes on the lower back and the output of the moisture-detecting RFID tag 10 can therefore be also detected on the lower back.

<Relay Antenna Unit for Diaper Equipped with Moisture-Detecting RFID Tag>

Figure 19A:
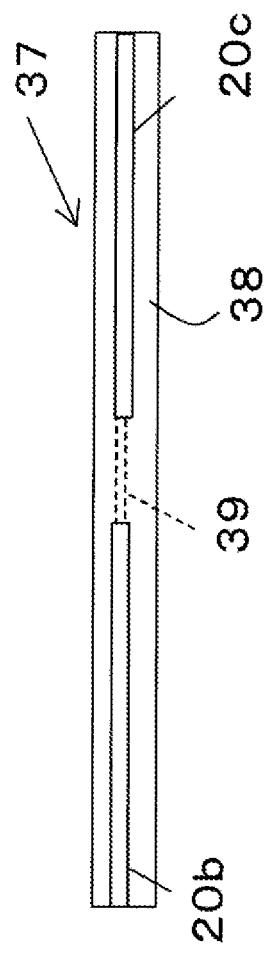
FIG. 19A is a schematic diagram of the configuration of a relay antenna unit used in the diaper equipped with a moisture-detecting RFID tag, according to the second embodiment
Figure 19B:
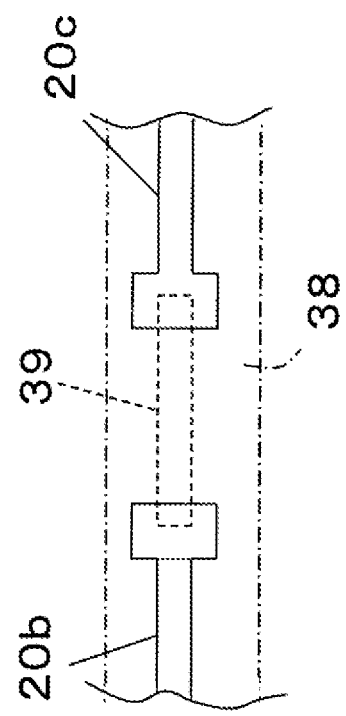
FIG. 19B is an enlarged diagram of the connection point between the relay antennas and the moisture-detecting RFID tag in the relay antenna unit of FIG. 19A.

FIG. 19A is a schematic diagram of the configuration of a relay antenna unit 37 used in the diaper 30*a* equipped with a moisture-detecting RFID tag, according to the second embodiment. FIG. 19B is an enlarged diagram of the connection points between the relay antennas 20*b* and 20*c*, and the moisture-detecting RFID tag in the relay antenna unit 37 of FIG. 19A.

As depicted in FIG. 19A, the relay antennas used in the diaper 30*a* equipped with a moisture-detecting RFID tag may be configured as the relay antenna unit 37 that is a separate article from the diaper. The relay antenna unit 37 includes a band-like supporter 38 and the relay antennas 20*b* and 20*c* disposed on the supporter. For example, a flexible object such as a cloth, a tape, a film, a paper sheet, or a silicone may be used as the supporter 38. The relay antennas 20*b* and 20*c* may be formed on the supporter 38 by printing, vapor-deposition, or the like. The relay antenna unit 37 may have any one shape of, for example, a band shape, a belt shape, a rope shape, and a film shape. As depicted in FIG. 19B, the supporter 38 may have guidelines 39 disposed thereon for the positions for the relay antennas 20*b* and 20*c* to be attached. The guidelines 39 correspond to the position to arrange the moisture-detecting RFID tag 10 arranged on the inner face side of the diaper. For example, the guidelines 39 may be those that correspond to the center of the moisture-detecting RFID tag 10. The guidelines 39 may not have the shape as that of the moisture-detecting RFID tag 10 itself. The alignment is facilitated for the relay antennas 20*b* and 20*c*, and the moisture-detecting RFID tag 10 by arranging the relay antennas 20*b* and 20*c* along the guidelines 39. The attachment of the relay antennas 20*b* and 20*c* is thereby facilitated. In this case, a mark indicating the arrangement position for the moisture-detecting RFID tag 10 may be presented on the outer face side of the diaper. Otherwise, a mark indicating the position to attach there at the relay antenna unit 37 may be presented on the outer face side of the diaper.

The relay antennas 20*b* and 20*c* may integrally be structured like those of the diaper 30*a* equipped with a moisture-detecting RFID tag as above or may be configured as a separate article from the diaper like the antenna unit 37.

Third Embodiment

Figure 20A:
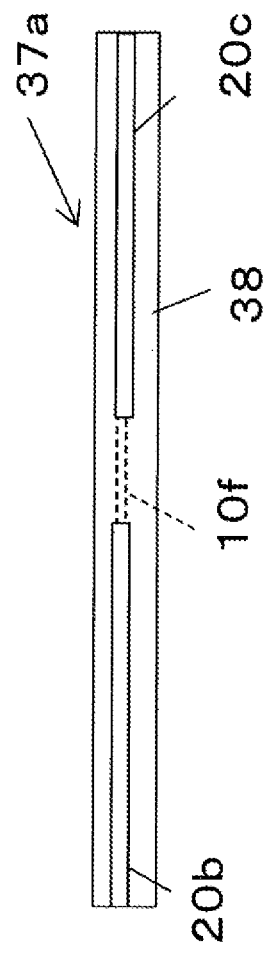
FIG. 20A is a top diagram of the configuration of a moisture-detecting RFID tag unit according to a third embodiment.
Figure 20B:
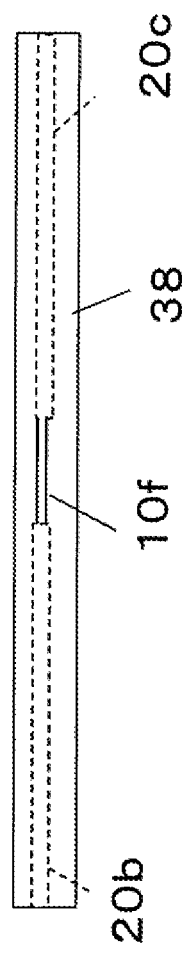
FIG. 20B is a bottom diagram of FIG. 20A.
Figure 20C:
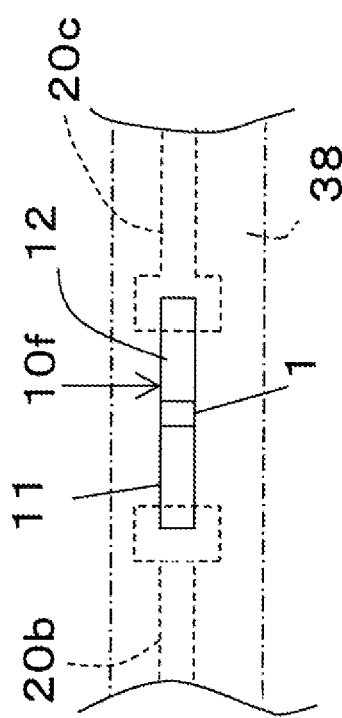
FIG. 20C is an enlarged diagram of the connection point between the relay antenna and the moisture-detecting RFID tag in the moisture-detecting RFID tag unit of FIG. 20A.

FIG. 20A is a top diagram of the configuration of a moisture-detecting RFID tag unit 37*a* according to a third embodiment. FIG. 20B is a bottom diagram of FIG. 20A. FIG. 20C is an enlarged diagram of the connection points between the relay antennas 20*b* and 20*c*, and a moisture-detecting RFID tag 10*f* in the moisture-detecting RFID tag unit 37*a* of FIG. 20A. FIG. 21A is a cross-sectional diagram of a cross-sectional structure of the moisture-detecting RFID tag unit 37*a* of FIG. 20A. FIG. 21B is a schematic cross-sectional diagram of the state where the moisture-detecting RFID tag unit 37*a* of FIG. 21A is attached to a waterproof material 32 on the outer face side of the diaper 30*a*.

Compared to the relay antenna unit 37 according to the second embodiment, this moisture-detecting RFID tag unit 37*a* differs therefrom in that the moisture-detecting RFID tag 10*f* is disposed. Compared to the moisture-detecting RFID tag 10 according to the first embodiment, the moisture-detecting RFID tag 10*f* differs therefrom in that the moisture-detecting RFID tag 10*f* does not include the opposite electrode 13 and the moisture-absorptive material 14. The moisture-detecting RFID tag 10*f* forms a capacitance with the object having moisture to be detected. The variation of the moisture amount of the object can thereby be output as the variation of the communication distance or the signal intensity originated from the variation of the electric lengths of the antenna elements, the variation of the capacitance between the antenna elements, or the like.

The attachment point of the moisture-detecting RFID tag 10*f* in the center to the diaper 30*a* may be processed such that the moisture-detecting RFID tag 10*f* is close to the moisture in the diaper 30*a*. For example, the moisture-detecting RFID tag 10*f* may be structured to adhere to the diaper 30*a* needing no protective film therefor. Otherwise, though the protective film is disposed, any thin material may be selected as the protective film. It is preferred that a structure be employed according to which an adhesive tape is disposed around the moisture-detecting RFID tag 10f to thereby bring the moisture-detecting RFID tag 10f and the diaper 30a into direct contact with each other.

The moisture-detecting RFID tag unit 37a includes the band-like supporter 38, the moisture-detecting RFID tag 10f disposed on the supporter 38, and the relay antennas 20b and 20c that are capacitively coupled with the antenna elements 11 and 12 of the moisture-detecting RFID tag 10f and that extend the communication range by relaying the output of the moisture-detecting RFID tag 10f. For example, the antenna elements 11 and 12 of the moisture-detecting RFID tag 10f, and the relay antennas 20b and 20c are respectively capacitively coupled with each other through the supporter 38.

The moisture-detecting RFID tag unit 37a is attached for the moisture-detecting RFID tag 10f to adhere to the moisture-absorptive material 32 on the outer face side of the diaper 30a, and can thereby be used to detect any moisture in the diaper 30a. In this case, moisture-absorptive materials 34a and 34b on the inner side of the diaper 30a form capacitance for the connection portions between the antenna elements 11 and 12, and the RFIC element 1 of the moisture-detecting RFID tag 10f, and any variations of the moisture amounts of the moisture-absorptive materials 34a and 34b can be output as the variation of the communication distance or the signal intensity originated from the variation of the electric lengths of the antenna elements 11 and 12, the variation of the capacitance between the antenna elements, or the like.

The use of the moisture-detecting RFID tag unit 37a is not limited to the detection of the moisture of a diaper. The moisture-detecting RFID tag unit 37a is usable for detecting moisture of any object only when the object forms capacitance for the connection portion between the antenna elements 11 and 12, and the RFIC element 1 of the moisture-detecting RFID tag 10f.

Fourth Embodiment

Compared to the diaper equipped with a moisture-detecting RFID tag according to the first embodiment, a diaper equipped with a moisture-detecting RFID tag according to the fourth embodiment differs therefrom in that the relay antenna has a water-soluble structure (not shown). With this structure, when the urine also leaks to an unintended point, though the moisture cannot be detected by the moisture-detecting RFID tag, the relay antenna itself is dissolved by the leaked urine. No effect of relaying the output by the relay antenna can thereby be acquired and detection of any moisture is thereby enabled.

Fifth Embodiment

Figure 22:
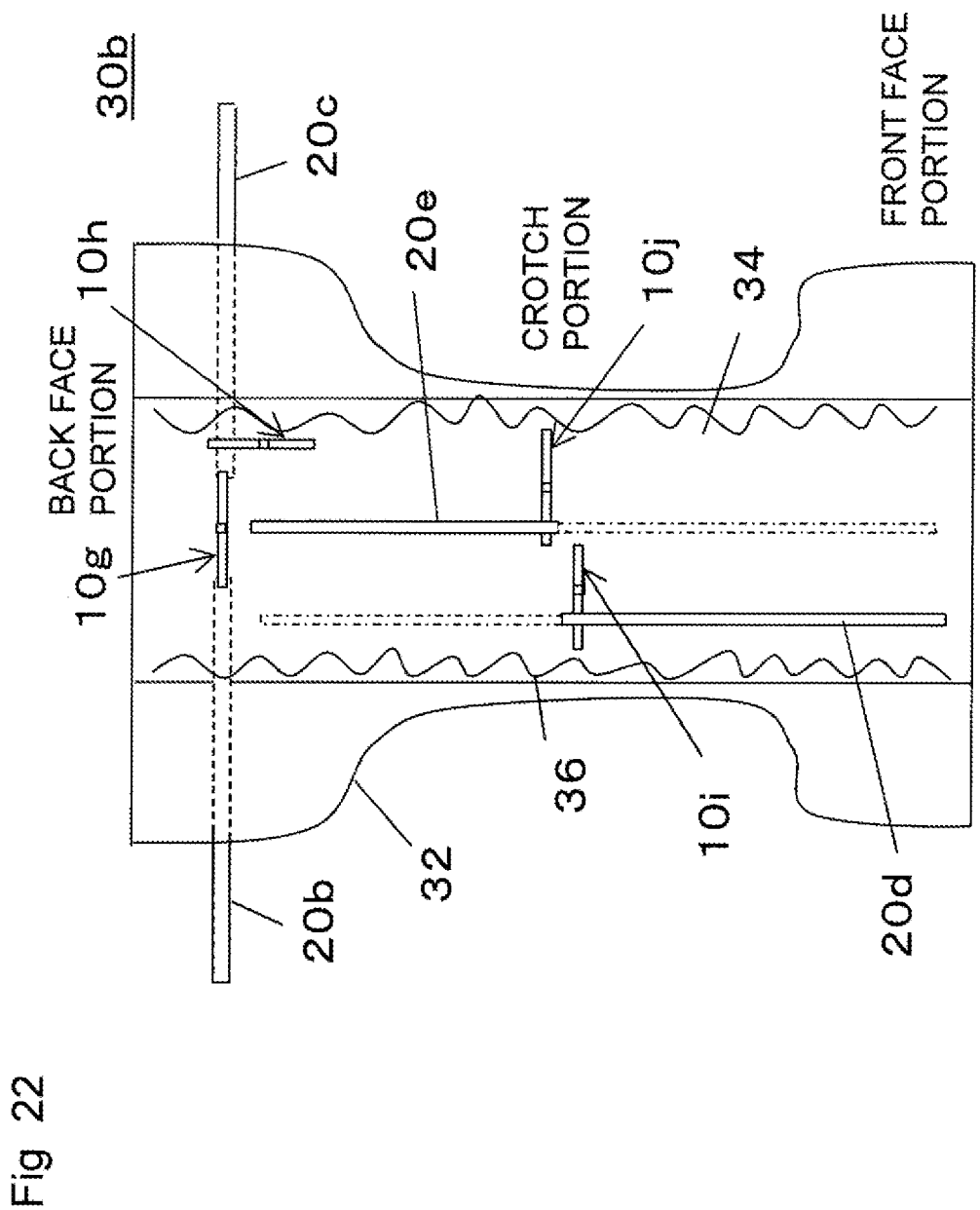
FIG. 22 is a diaper development diagram of the configuration of a diaper equipped with a moisture-detecting RFID tag, according to a fifth embodiment.

FIG. 22 is a diaper development diagram of the configuration of a diaper 30b equipped with a moisture-detecting RFID tag, according to the fifth embodiment.

Compared to the diapers each equipped with a moisture-detecting RFID tag according to the first and the second embodiments, the diaper 30b equipped with a moisture-detecting RFID tag differs therefrom in that moisture-detecting RFID tags 10g, 10h, 10i, and 10j are arranged in the back face portion and the crotch portion. The diaper 30b also differs therefrom in that the plural relay antennas 20b, 20c, 20d, and 20e are disposed. The relay antennas 20d and 20e may be extended from the back face portion to the front face portion through the crotch portion. The point at which a sufficient output can be acquired can be disposed for a wide angle. Detection of the number of the excretion sessions, detection of the excretion position, and the like are enabled by arranging the plural moisture-detecting RFID tags 10g, 10h, 10i, and 10j. The detectable range by the reader can be extended by arranging the plural relay antennas 20b, 20c, 20d, and 20e.

Sixth Embodiment

Figure 23A:
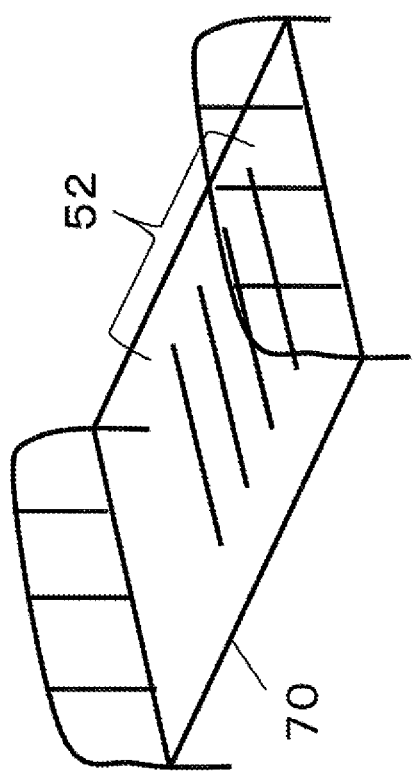
FIG. 23A is a schematic perspective diagram of the configuration of a relay antenna disposed on a bed in a relay system for a diaper equipped with a moisture-detecting RFID tag, according to a sixth embodiment.
Figure 23B:
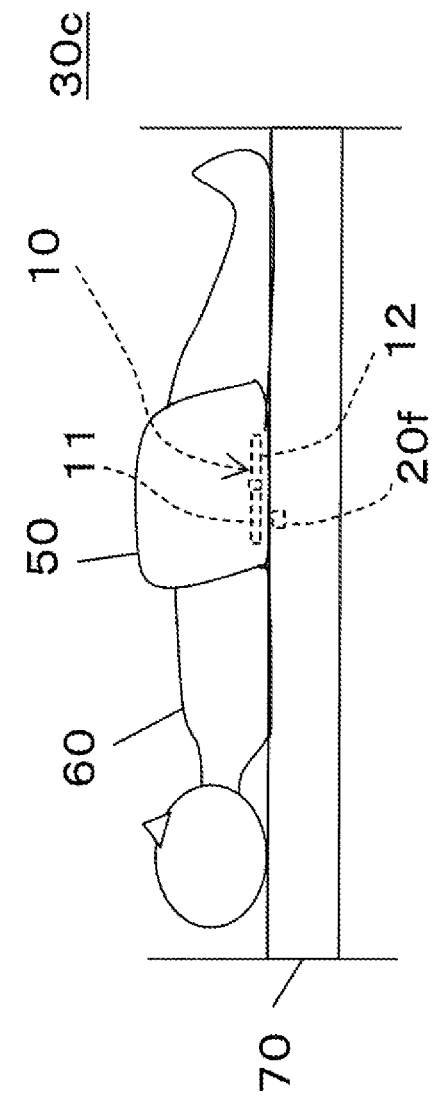
FIG. 23B is a side diagram of the state where a human body having the diaper equipped with a moisture-detecting RFID tag worn thereon lies on the bed.
Figure 23C:
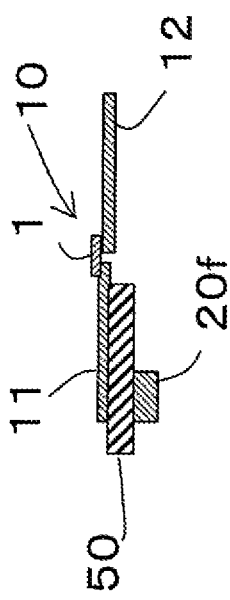
FIG. 23C is a schematic cross-sectional diagram of the connection point between the RFID tag and the relay antenna of FIG. 23B.

FIG. 23A is a schematic perspective diagram of the state where a position mark 52 is disposed that indicates the position of the relay antenna on a bed 70 in a relay system 30c for a diaper equipped with a moisture-detecting RFID tag, according to the sixth embodiment. FIG. 23B is a side diagram of the state where the human body 60 lies on the bed 70 who wears a diaper 50 having the moisture-detecting RFID tag 10 inserted therein. FIG. 23C is a schematic cross-sectional diagram of the connection point between the RFID tag 10 and a relay antenna 20f of FIG. 23B. In FIG. 23B, the clothes other than the diaper 50 are not depicted. In FIG. 23C, items other than the relevant members are not depicted.

The relay system 30c for a diaper equipped with a moisture-detecting RFID tag differs in that the diaper 50 only has lone moisture-detecting RFID tag 10 inserted therein and does not include the relay system. On the other hand, the relay antenna 20f is arranged on the upper face of the bed 70. The relay antenna 20f may include plural relay antennas. The human body lies on the bed, and the first radiation electrode 11 of the moisture-detecting RFID tag 10 arranged in the back face portion of the diaper 50 and the relay antenna 20f arranged on the bed 70 thereby adhere to each other through the diaper 50 to be capacitively coupled with each other (FIG. 23C). The relay system 30c for the diaper equipped with a moisture-detecting RFID tag is thereby configured. The position mark 52 to align the position of the moisture-detecting RFID tag 10 arranged in the diaper 50 with the relay antenna 20f may be disposed on the bed 70.

A relay antenna to be capacitively coupled with the moisture-detecting RFID tag 10 in the diaper 50 may be disposed in the diaper 50. In this case, coupling of the relay antenna in two stages may be configured with the relay antenna 20f of the bed 70 and the relay antenna disposed in the diaper 50. The relay antenna may be disposed in plural stages.

Sensing of a solid waste can also be realized by adding an odor sensor (not depicted) to the bed 70 in addition to the urine sensing that uses the moisture-detecting RFID tag and the relay antenna.

A function of detecting moisture using two conductor wires may further be disposed on the bed 70. When urine does not touch the tag in the diaper due to the posture and the urine adheres to the bed 70, this fact can be detected and reported by disposing the two conductor wires on the bed 70.

It is usually difficult to detect any output from the moisture-detecting RFID tag 10 arranged in the back face portion of the diaper. According to the configuration of the relay system 30c for the diaper equipped with a moisture-detecting RFID tag, the moisture-detecting RFID tag 10 arranged in the back face portion of the diaper 50 and the relay antenna 20f on the upper face of the bed 70 can capacitively be coupled. The output from the moisture-detecting RFID tag 10 can thereby be detected from the side face of the bed 70 through the relay antenna 20f.

Seventh Embodiment

Figure 24C:
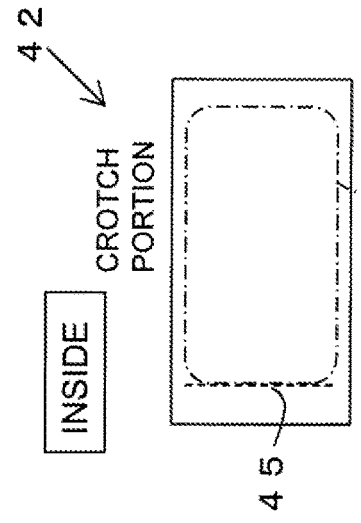
FIG. 24C is a schematic diagram of the inner side of the inner part.
Figure 24D:
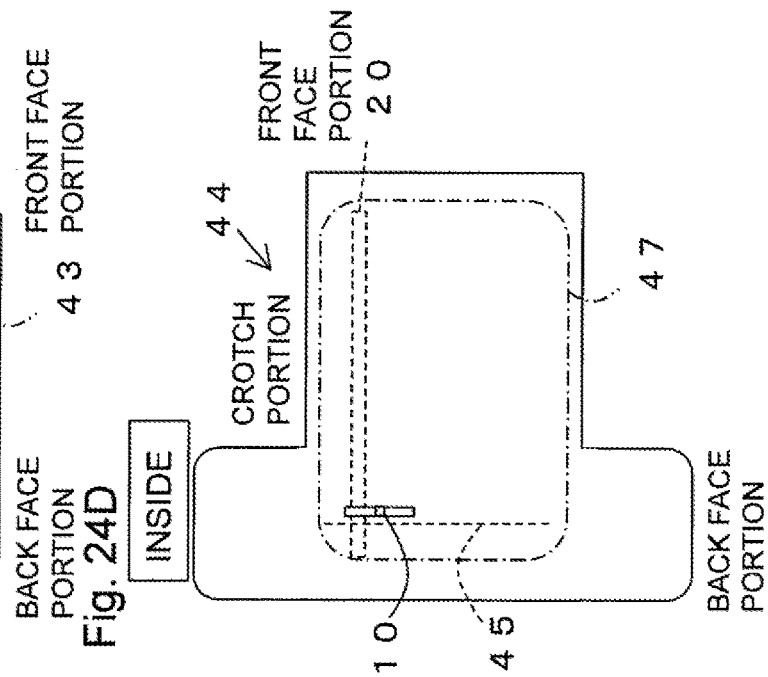
FIG. 24D is a schematic diagram of the inner side of the outer part.
Figure 24A:
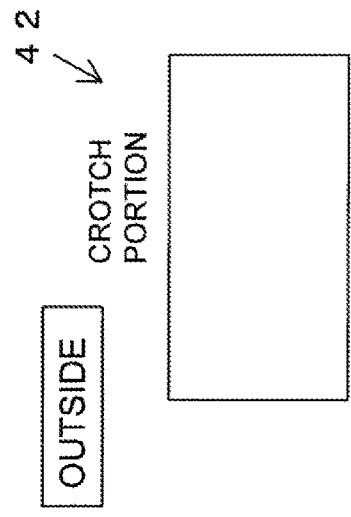
FIG. 24A is a schematic diagram of the outer side of an inner part that forms a diaper equipped with a moisture-detecting RFID tag, according to a seventh embodiment.
Figure 24B:
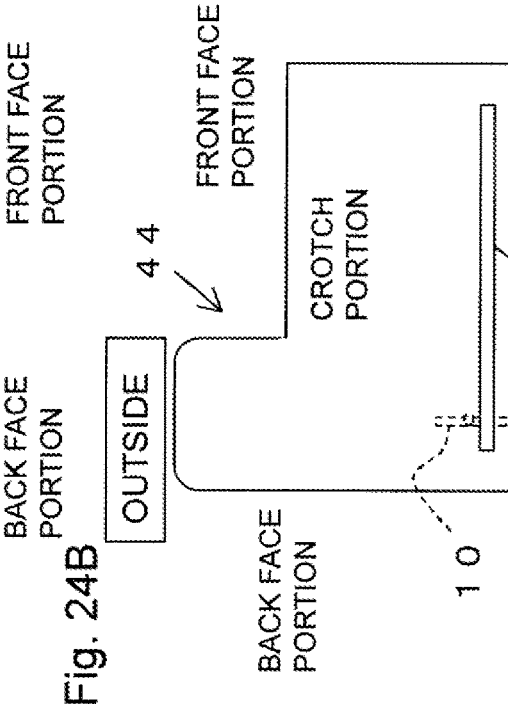
FIG. 24B is a schematic diagram of the outer side of an outer part.

FIG. 24A is a schematic diagram of the outer side of the inner part 42 that forms a diaper equipped with a moisture-detecting RFID tag, according to the seventh embodiment. FIG. 24B is a schematic diagram of the outer side of an outer part 44. FIG. 24C is a schematic diagram of the inner side of the inner part 42. FIG. 24D is a schematic diagram of the inner side of the outer part 44. The inner part 42 and the outer part 44 are depicted to be simplified compared to the actual ones.

FIGS. 24A to 24D depict the back face portion, the crotch portion, and the front face portion while these portions will not again be depicted to avoid redundancy in FIGS. 25 to 41 described later.

The diaper equipped with a moisture-detecting RFID tag includes the inner part 42 and the outer part 44. A border line 43 of the moisture-absorptive material is depicted by an imaginary line on the inner side of the inner part 42. Another border line 47 of the moisture-absorptive material is also depicted by an imaginary line on the inner side of the outer part 44. The RFID tag 10 is arranged on the inner side of the outer part 44 and the relay antenna 20 is extended from the back face portion on the outer side of the outer part 44 to the front face portion through the crotch portion to cause one end thereof to face the RFID tag 10 on the inner side sandwiching the outer part 44 therebetween. The RFID tag 10 on the inner side of the outer part 44 and the one end of the relay antenna 20 on the outer side capacitively couple with each other sandwiching the outer part 44 therebetween. The reading of the RFID tag 10 can be executed by, for example, a handheld reader through the relay antenna.

According to the diaper equipped with a moisture-detecting RFID tag, because the RFID tag 10 is attached to the outer part 44, the moisture detection can be executed for each of plural inner parts 42 changing the plural inner parts 42 one after another until the outer part 44 is discarded. The running cost can therefore be suppressed. Because the relay antenna 20 is only attached to the outer part 44, the diaper can be completed by executing additional processing for an existing diaper. To reduce the influence from the moisture in the inner part 42, the relay antenna 20 is arranged through the portion whose moisture-absorptive material is thick, of the outer part 44, that is, the outer side of the outer part 44.

In the diaper equipped with a moisture-detecting RFID tag, the RFID tag 10 is arranged on the inner side of the outer part 44 that corresponds to an absorption upper limit position 45 of the inner part 42. The RFID tag 10 is arranged in the lateral direction, i.e., that is perpendicular to the direction from the back face portion to the front face portion through the crotch portion for the outer part 44. The connection portion between the RFID tag 10 and the relay antenna 20 is sensitive to any moisture. The connection portion between the RFID tag 10 and the relay antenna 20 therefore may act as a moisture detection point when the RFID tag 10 is attached in the longitudinal direction, i.e., along the back face from the crotch portion. The moisture reaching the absorption upper limit position 45 can be received by the RFID tag 10 and the fact that the moisture reaches the upper limit can be learned, by arranging the RFID tag 10 in the lateral direction along the absorption upper limit position 45 as above. Any inaccurate report issued before the moisture reaches the upper limit can be prevented by arranging the RFID tag 10 in the lateral direction along the absorption upper limit position 45. On the other hand, any moisture can also be detected utilizing the property that the connection portion is sensitive to moisture between the RFID tag 10 and the relay antenna 20.

When the relay antenna 20 is caused to pass through the lower back of the outer part 44, because the lower back includes no absorptive object, the electric power received by the relay antenna from the handheld reader is absorbed by the human body in the lower back before the electric power reaches the RFID tag 10 on the back side and no transmission can be executed even when the RFID tag is not wet. The case may therefore be present where presence or absence of any moisture cannot be detected. To avoid this, a spacer needs to be added to the lower back. In contrast, absorptive objects are originally included in the diaper (in the inner part 42 and the outer part 44) in the crotch portion. It is noted that a device to avoid the influence of the human body is not needed by causing the relay antenna 20 to pass through the crotch portion as described above. When the thickness of the absorptive object of the outer part differs depending on the position thereof, the communication distance can be extended by attaching the relay antenna 20 to the portion whose absorptive object has a large thickness on the outer side of the outer part 44. The electric power flowing through the relay antenna 20 can be prevented from being absorbed by the human body before the electric power reaches the RFID tag 10 by setting the distance between the relay antenna 20 and the human body to be a distance corresponding to one absorptive object or longer.

As to the inner part 42, it is further noted that nothing needs to be attached thereto on the inner side and the outer side thereof, and any commercially available inner part 42 is usable as it is.

On the other hand, for example, the relay antenna 20 on the outer side of the outer part 44 may be attached by the diaper manufacturer in the shipping stage or may be attached by the caretaker. For example, the RFID tag 10 on the inner side of the outer part 44 may be attached in the shipping stage or by the caretaker. The RFID tag 10 is attached in the lateral direction at the position 45 that corresponds to the absorption upper limit of the inner part 42, on the inner side of the outer part 44. The RFID tag 10 is adapted to be detachable and the position for the attachment may properly be changed by the caretaker. In this case, overlapping with the relay antenna is essential and an indication of the guideline for the alignment for arranging the RFID tag 10 may be disposed inside the diaper (the outer part 44).

Eighth Embodiment

FIG. 25A is a schematic diagram of the outer side of the inner part 42 that forms a diaper equipped with a moisture-detecting RFID tag, according to the eighth embodiment. FIG. 25B is a schematic diagram of the outer side of the outer part 44. FIG. 25C is a schematic diagram of the inner side of the inner part 42. FIG. 25D is a schematic diagram of the inner side of the outer part 44.

The diaper equipped with a moisture-detecting RFID tag includes the inner part 42 and the outer part 44. Three RFID tags 10k, 10l, and 10m are arranged on the inner side of the outer part 44, and three relay antennas 20g, 20h, and 20i respectively corresponding to the RFID tags 10k, 10l, and 10m are extended from the back face portion on the outer side of the outer part 44 to the front face portion through the crotch portion. The reading of the RFID tags 10k, 10l, and 10m can be executed by, for example, a handheld reader through the relay antennas 20g, 20h, and 20i.

According to this diaper equipped with a moisture-detecting RFID tag, the RFID tags can be disposed at not only the absorption upper limit position 45 of the inner part 42 but also, for example, at positions to which urine tends to leak at the lateral recumbent position of the person needing care, by attaching the plural RFID tags 10*k*, 10*l*, and 10*m*. Leaking from the side and the like can thereby be also detected. The communication is unable when any urine leakage occurs in only the outer part portion to which the RFID tags 10*k*, 10*l*, and 10*m* are attached. The relay antennas 20*g*, 20*h*, and 20*i* can each be realized at a low cost by each being formed to have a folded structure of a straight-line conductor.

As to the inner part 42, nothing needs to be attached thereto on the inner side and on the outer side thereof and any commercially available inner part 42 is usable as it is.

On the other hand, the relay antennas 20*g*, 20*h*, and 20*i* on the outer side of the outer part 44 may be attached by the diaper manufacturer in the shipping stage or may be attached by the caretaker. For example, the RFID tags 10*k*, 10*l*, and 10*m* on the inner side of the outer part 44 may be attached in the shipping stage or by the caretaker.

In this diaper equipped with a moisture-detecting RFID tag, the three RFID tags 10*k*, 10*l*, and 10*m* can each be read by shifting the positions of terminating portions 41 from each other that are reading portions of the three relay antennas 20*g*, 20*h*, and 20*i*. For example, the reading can be executed using a handheld reader shifting the position for the reading.

In this eighth embodiment, the relay antennas 20*g*, 20*h*, and 20*i* are disposed to each be dedicated to one RFID tag of the RFID tags 10*k*, 10*l*, and 10*m*. This is because of a problem that, when one relay antenna is halfway branched into three, the electric power is not evenly dispersed into the three RFID tags and all of the three RFID tags cannot be read. All of the three RFID tags 10*k*, 10*l*, and 10*m* can be read by disposing the relay antennas 20*g*, 20*h*, and 20*i* respectively for the RFID tags 10*k*, 10*l*, and 10*m* as above.

Ninth Embodiment

FIG. 26A is a schematic diagram of the outer side of the inner part 42 that forms a diaper equipped with a moisture-detecting RFID tag, according to the ninth embodiment. FIG. 26B is a schematic diagram of the outer side of the outer part 44. FIG. 26C is a schematic diagram of the inner side of the inner part 42. FIG. 26D is a schematic diagram of the inner side of the outer part 44.

This diaper equipped with a moisture-detecting RFID tag includes the inner part 42 and the outer part 44. The RFID tag 10 is arranged on the inner side of the outer part 44, and two relay antennas 20*j* are extended on the right and the left sides of the lower back on the outer side of the outer part 44. In the exemplary aspect, the reading of the RFID tag 10 can be executed through the relay antennas 20*j* by, for example, a handheld reader.

This diaper equipped with a moisture-detecting RFID tag is characterized in that the two relay antennas 20*j* are extended on the right and the left sides of the lower back. When the relay antennas are caused to pass through the portion between the legs, the relay antennas are influenced by the moisture of the inner part 42 until the moisture reaches the absorption upper limit position 45 of the inner part 42, and the communication distance is reduced.

In contrast, when the relay antennas 20J are arranged to pass through the lower back as above, the relay antennas 20*j* are not influenced by the moisture of the inner part 42 and the caretaker can execute the reading at the communication distance equal to that in the initial state immediately after the wearing with no urine excreted until the moisture reaches the absorption upper limit position 45 of the RFID tag 10.

As to the inner part 42, nothing needs to be attached thereto on the inner side and the outer side thereof, and any commercially available inner part 42 is usable as it is.

On the other hand, for example, the relay antennas 20*j* of the outer part 44 may be attached by the diaper manufacturer in the shipping stage or may be attached by the caretaker. For example, the RFID tag 10 on the inner side of the outer part 44 may be attached by the diaper manufacturer in the shipping stage or may be attached by the caretaker. To avoid the influence of the human body, an absorptive object to be a spacer 29 may be arranged on the lower back on the inner side of the outer part 44, that corresponds to the position through which the relay antennas 20*j* pass, of the lower back on the outer side of the outer part 44. The absorptive object 29 may be attached by the diaper manufacturer in the shipping stage.

In this diaper equipped with a moisture-detecting RFID tag, the RFID tag 10 is arranged on the inner side of the outer part 44 that corresponds to the absorption upper limit position 45 of the inner part 42 in the same manner as that in the seventh embodiment. The RFID tag 10 is arranged in the lateral direction, i.e., perpendicular to the direction from the back face portion to the front face portion through the crotch portion for the outer part 44.

Tenth Embodiment

Figure 27C:
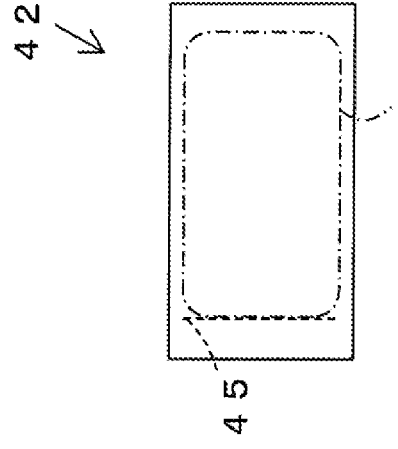
FIG. 27C is a schematic diagram of the inner side of the inner part.
Figure 27D:
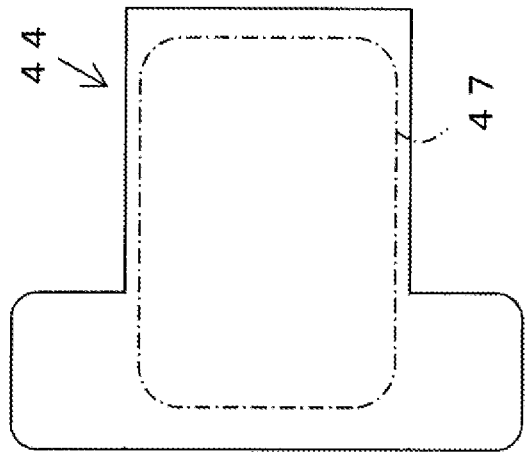
FIG. 27D is a schematic diagram of the inner side of the outer part.
Figure 27A:
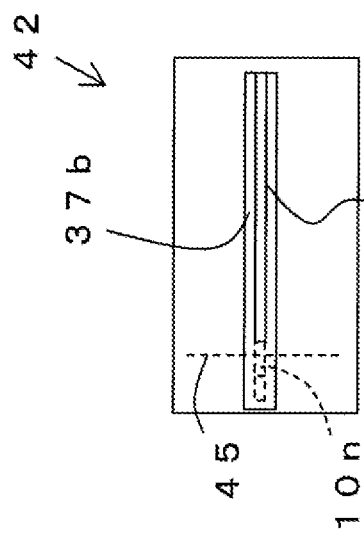
FIG. 27A is a schematic diagram of the outer side of an inner part that forms a diaper equipped with a moisture-detecting RFID tag, according to a tenth embodiment.
Figure 27B:
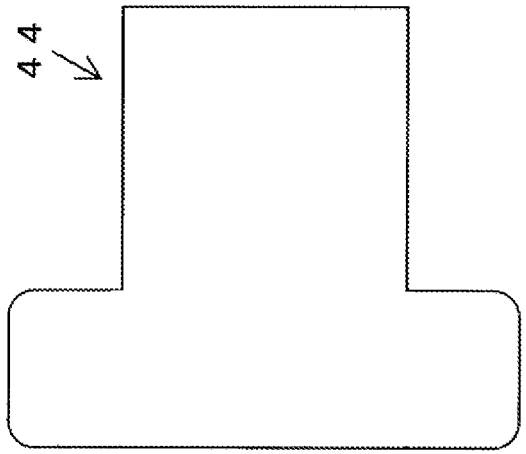
FIG. 27B is a schematic diagram of the outer side of an outer part.
Figure 28A:
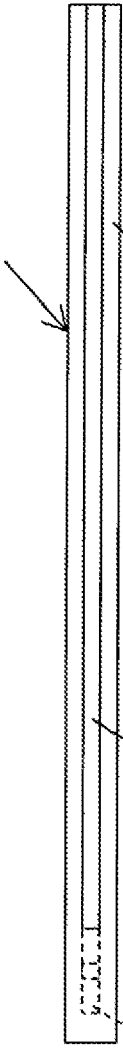
FIG. 28A is a plan diagram of the configuration on a surface side of a moisture-detecting RFID tag unit according to the tenth embodiment and FIG. 28B is a plan diagram of the configuration on a back side of FIG. 28A.
Figure 28B:

FIG. 27A is a schematic diagram of the outer side of the inner part 42 that forms a diaper equipped with a moisture-detecting RFID tag, according to the tenth embodiment. FIG. 27B is a schematic diagram of the outer side of the outer part 44. FIG. 27C is a schematic diagram of the inner side of the inner part 42. FIG. 27D is a schematic diagram of the inner side of the outer part 44. FIG. 28A is a plan diagram of the configuration on a surface side of a moisture-detecting RFID tag unit 37*b* according to the tenth embodiment. FIG. 28B is a plan diagram of the configuration on a back side of FIG. 28A.

The diaper equipped with a moisture-detecting RFID tag includes the inner part 42 and the outer part 44, and the all-in-one moisture-detecting RFID tag unit 37*b* including an RFID tag 10*n* and a relay antenna 20*k* is arranged on the outer side of the inner part 42.

The moisture-detecting RFID tag unit 37*b* has the relay antenna 20*k* disposed on its surface side and the RFID tag 10*n* disposed on its back side. The end portion of the RFID tag 10*n* and the end portion of the relay antenna 20*k* face each other through the supporter 38 and are capacitively coupled with each other.

The moisture-detecting RFID tag unit 37*b* is extended from the back face portion on the outer side of the inner part 42 to the front face portion through the crotch portion. The RFID tag 10 of the moisture-detecting RFID tag unit 37*b* faces the face on the outer side of the inner part 42. The reading of the RFID tag 10*n* can be executed by, for example, a handheld reader in the vicinity of the navel in the front face portion through the relay antenna 20*k* of the moisture-detecting RFID tag unit 37*b*.

In this moisture-detecting RFID tag unit 37*b*, the all-in-one moisture-detecting RFID tag unit 37*b* including the RFID tag 10*n* and the relay antenna 20*k* is arranged on the outer side of the inner part 42 and can therefore be attached to the commercially available inner part 42 by the caretaker when the person needing care wears the diaper. Detection of any excretion can thereby be easily executed. Water resistance may be imparted to the moisture-detecting RFID tag unit 37b for this unit 37b to be able to repeatedly be washed and used. To bond the moisture-detecting RFID tag unit 37b to the inner part 42, for example, a tape may be used.

The moisture-detecting RFID tag unit 37b only has to be attached to the commercially available inner part 42 as above and any commercially available inner part 42 is therefore usable as it is. The moisture-detecting RFID tag unit 37b can be attached by the caretaker when the person needing care wears the diaper. As to the outer part 44, nothing needs to be attached thereto on the inner side and the outer side thereof, and any commercially available outer part 44 is usable as it is.

As to the moisture-detecting RFID tag unit 37b, when the thickness of the supporter 38 of the relay antenna 20k is large, any influence of the moisture of the inner part 42 tends to be avoided and the reading distance becomes long. On the other hand, when the thickness of the supporter 38 of the relay antenna 20k is small, any influence of the moisture of the inner part 42 tends to be received and the reading distance becomes short.

Eleventh Embodiment

Figure 29C:
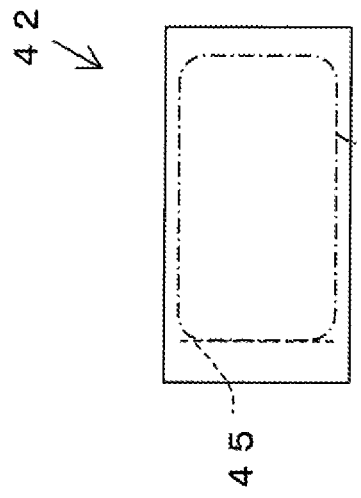
FIG. 29C is a schematic diagram of the inner side of the inner part.
Figure 29D:
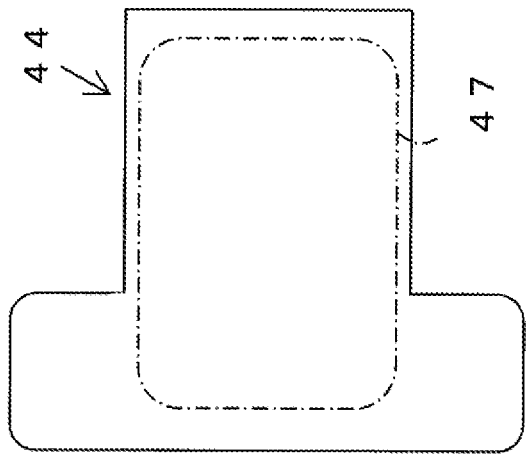
FIG. 29D is a schematic diagram of the inner side of the outer part.
Figure 29A:
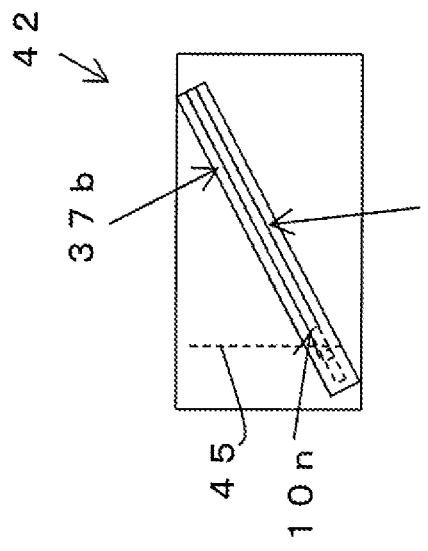
FIG. 29A is a schematic diagram of the outer side of an inner part that forms a diaper equipped with a moisture-detecting RFID tag, according to an eleventh embodiment.
Figure 29B:
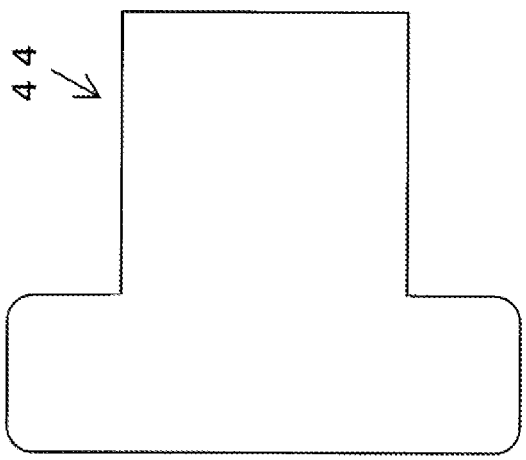
FIG. 29B is a schematic diagram of the outer side of an outer part.

FIG. 29A is a schematic diagram of the outer side of the inner part 42 that forms a diaper equipped with a moisture-detecting RFID tag, according to the eleventh embodiment. FIG. 29B is a schematic diagram of the outer side of the outer part 44. FIG. 29C is a schematic diagram of the inner side of the inner part 42. FIG. 29D is a schematic diagram of the inner side of the outer part 44.

The diaper equipped with a moisture-detecting RFID tag includes the inner part 42 and the outer part 44, and the all-in-one moisture-detecting RFID tag unit 37b including the RFID tag 10n and the relay antenna 20k is obliquely arranged on the outer side of the inner part 42. The RFID tag can be installed at the optimal position matching with the state of the person needing care. In this case, the relay antenna 20k for the reading can be extended from the back face portion to the front face portion through the crotch portion. The reading can thereby be also executed at the position desired by the caretaker such as, for example, a position in the vicinity of the navel in the front face portion as the reading position.

When the RFID tag and the relay antenna are not brought into direct contact with the human body, a portion of the relay antenna 20k can be brought into contact with the human body such as the lower back depending on the thickness of the supporter 38. For example, it is preferred that the supporter 38 have a thickness that corresponds to one absorptive object.

The moisture-detecting RFID tag unit 37b only has to be attached to the commercially available inner part 42 as above and any commercially available inner 42 is therefore usable as it is. The moisture-detecting RFID tag unit 37b can be attached by the caretaker when the person needing care wears the diaper. As to the outer part 44, nothing needs to be attached thereto on the inner side and the outer side thereof, and any commercially available outer part 44 is usable as it is.

Twelfth Embodiment

Figure 30C:
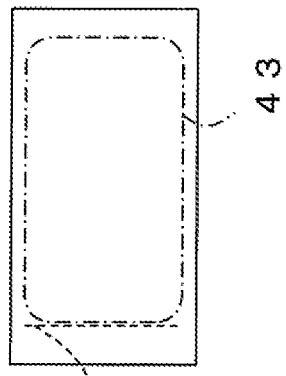
FIG. 30C is a schematic diagram of the inner side of the inner part.
Figure 30D:
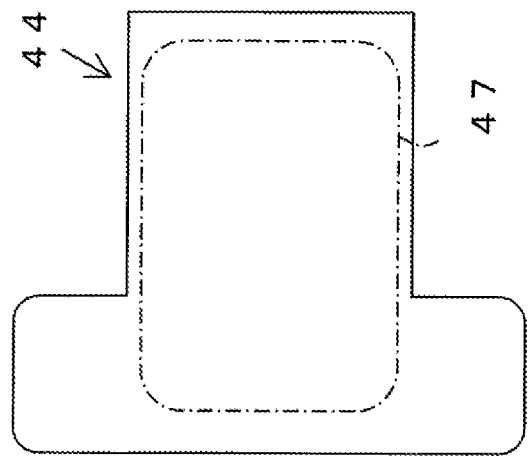
FIG. 30D is a schematic diagram of the inner side of the outer part.
Figure 30A:
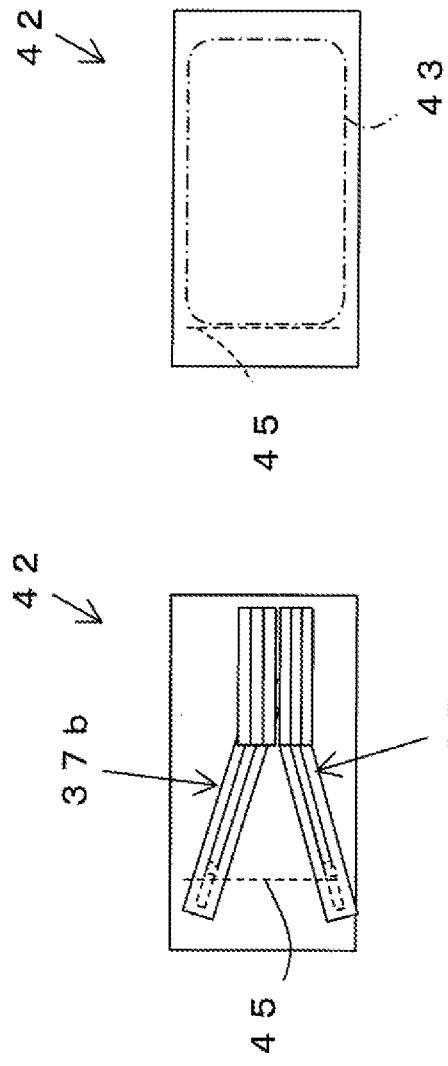
FIG. 30A is a schematic diagram of the outer side of an inner part that forms a diaper equipped with a moisture-detecting RFID tag, according to a twelfth embodiment.
Figure 30B:
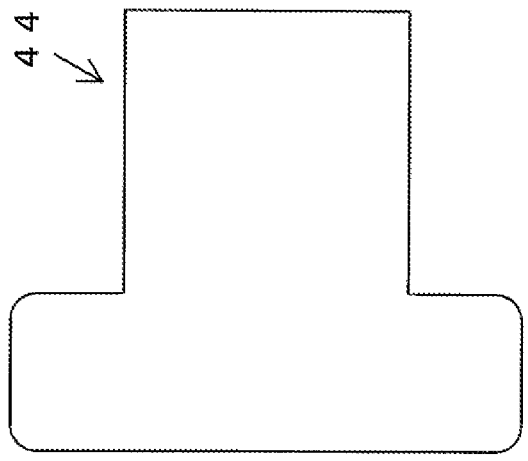
FIG. 30B is a schematic diagram of the outer side of an outer part.

FIG. 30A is a schematic diagram of the outer side of the inner part 42 that forms a diaper equipped with a moisture-detecting RFID tag, according to the twelfth embodiment. FIG. 30B is a schematic diagram of the outer side of the outer part 44. FIG. 30C is a schematic diagram of the inner side of the inner part 42. FIG. 30D is a schematic diagram of the inner side of the outer part 44.

The diaper equipped with a moisture-detecting RFID tag includes the inner part 42 and the outer part 44, and two all-in-one moisture-detecting RFID tag units 37b and 37c each including the RFID tag 10n and the relay antenna 20k are arranged in parallel to each other on the outer side of the inner part 42. For example, the RFID tags 10n of the two moisture-detecting RFID tag units 37b and 37c are adapted to each be arranged at one of the end portions in the back face portion on the outer side of the inner part 42, that is, substantially at the absorption upper limit position 45. The attachment positions of the RFID tags 10n are not limited to the absorption upper limit position 45 and, for example, may be the positions at which urine leakage or the like of the person to be cared tends to occur. The number of the moisture-detecting RFID tag units is not limited to two, and three or more moisture-detecting RFID tag units may be used. When the plural moisture-detecting RFID tag units are used, the RFID tags can further be arranged at plural positions.

On the other hand, the two moisture-detecting RFID tag units 37b and 37c are each halfway folded and the relay antennas 20k thereof are arranged in parallel to each other.

For the reading of the RFID tags 10n, the reading can be executed by a handheld reader through the relay antennas 20k in, for example, the vicinity of the navel of the front face portion of the two moisture-detecting RFID tag units 37b and 37c.

The moisture-detecting RFID tag units 37b and 37c only have to be attached to the commercially available inner part 42 as above, and any commercially available inner part 42 is therefore usable as it is. The moisture-detecting RFID tag units 37b and 37c can be attached by the caretaker when the person needing care wears the diaper. As to the outer part 44, nothing needs to be attached thereto on the inner side and the outer side thereof, and the commercially available outer part 44 is usable as it is.

For the moisture-detecting RFID tag units 37b and 37c, the caretaker can cut each of the relay antennas 20k at an optional point to vary the overall length thereof to an optional length. It is therefore unnecessary to retain plural types of moisture-detecting RFID tag units 37b and 37c, and the cost can be reduced.

Thirteenth Embodiment

Figure 31C:
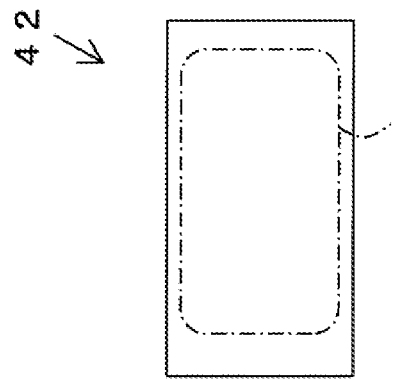
FIG. 31C is a schematic diagram of the inner side of the inner part.
Figure 31D:
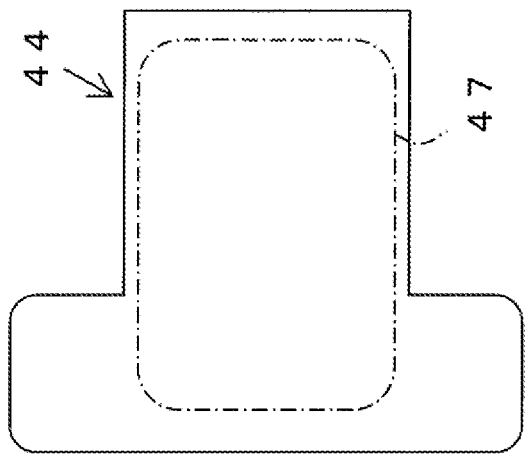
FIG. 31D is a schematic diagram of the inner side of the outer part.
Figure 31A:
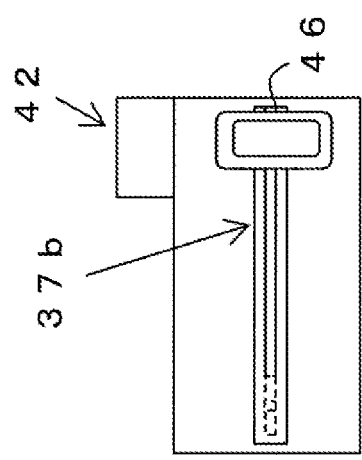
FIG. 31A is a schematic diagram of the outer side of an inner part that forms a diaper equipped with a moisture-detecting RFID tag, according to a thirteenth embodiment.
Figure 31B:
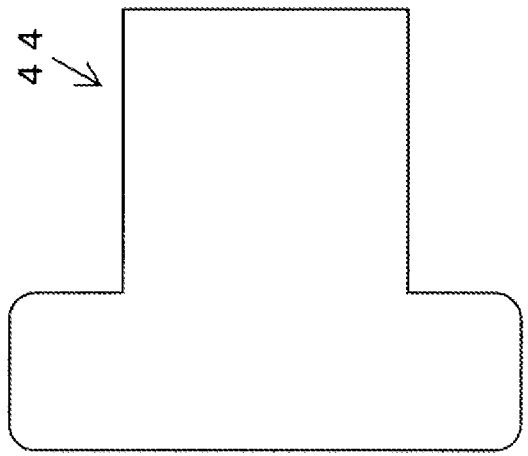
FIG. 31B is a schematic diagram of the outer side of an outer part.

FIG. 31A is a schematic diagram of the outer side of the inner part 42 that forms a diaper equipped with a moisture-detecting RFID tag, according to the thirteenth embodiment. FIG. 31B is a schematic diagram of the outer side of the outer part 44. FIG. 31C is a schematic diagram of the inner side of the inner part 42. FIG. 31D is a schematic diagram of the inner side of the outer part 44.

The diaper equipped with a moisture-detecting RFID tag includes the inner part 42 and the outer part 44, and the all-in-one moisture-detecting RFID tag unit 37b including the RFID tag 10n and the relay antenna 20k is arranged on the outer side of the inner part 42. An RFID reader and radio transfer unit 46 capable of communicating with the relay antenna 20k by the RFID is arranged in the vicinity of the relay antenna 20k. The RFID reader and radio transfer unit 46 may be configured as one all-in-one component, or the RFID reader and the radio transfer unit may each be configured as a separate component from each other. The RFID reader and radio transfer unit 46 may be arranged in, for example, the vicinity of the navel in the front face portion.

For the diaper equipped with a moisture-detecting RFID tag, the RFID reader and radio transfer unit 46 is arranged for the reading and the reading result can be informed of to the external caretaker in real time using, for example, Bluetooth (a registered trademark) or WiFi (a registered trademark). Because the information of the RFID tag 10*n* can be transferred using the radio transmission and the signal therefore does not necessarily need to be guided to the front face of the human body using the relay antenna 20*k*. Thus, when the RFID reader is placed immediately above the RFID tag 10*n*, however, even when any moisture is present in the inner part 42, the reading can be executed and the detection system does not function. For detecting the moisture, the RFID reader and radio transfer unit 46 needs to read not directly from the RFID tag 10*n* but indirectly from the RFID tag 10*n* through the relay antenna.

Because the RFID reader and radio transfer unit 46 is arranged for the reading, the reading result can be transferred to the caretaker and/or the person needing care in real time. Data can also be automatically collected. The unit 46 for the RFID and the radio transfer is structured to be separate from the moisture-detecting RFID tag unit 37*b* for the RFID tag and the relay antenna and may be fixed by, for example, a button/a tape/nipping or the like. The two units are structured to each be separate from each other and the moisture-detecting RFID tag unit 37*b* thereby only has to be replaced when the moisture-detecting RFID tag unit 37*b* for the RFID tag and the relay antenna fails to operate, and any increase of the cost can be suppressed.

Detection of any solid waste is enabled by adding to this unit an odor sensor that detects any odor included in the solid waste such as methylmercaptan.

It is noted that the moisture-detecting RFID tag unit 37*b* only has to be attached to the commercially available inner part 42 as above and the commercially available inner part 42 is therefore usable as it is. The moisture-detecting RFID tag unit 37*b* can be attached by the caretaker when the person needing care wears the diaper. As to the outer part 44, nothing needs to be attached thereto on the inner side and the outer side thereof, and any commercially available outer part 44 is usable as it is. The RFID reader and radio transfer unit 46 can be attached by the caretaker when the person needing care wears the diaper.

Figure 32A:
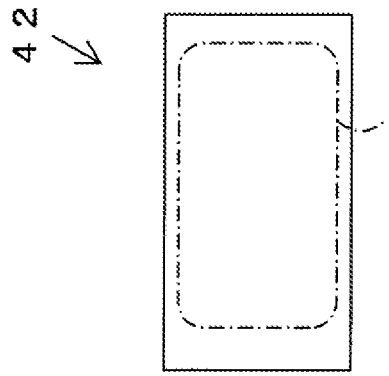
FIG. 32A is a schematic diagram of the outer side of an inner part that forms a diaper equipped with a moisture-detecting RFID tag, according to a modification example of the thirteenth embodiment.
Figure 32C:
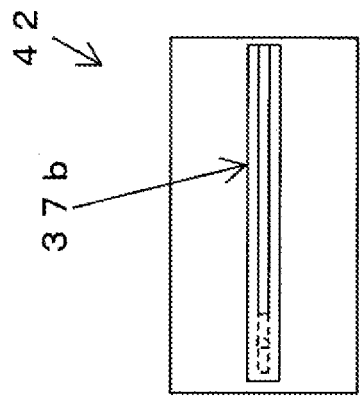
FIG. 32C is a schematic diagram of the inner side of the inner part.
Figure 32B:
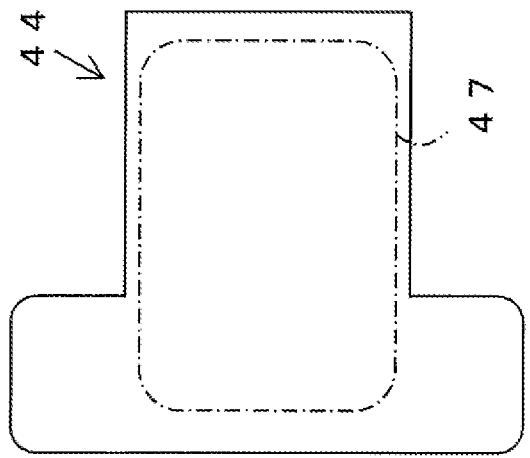
FIG. 32B is a schematic diagram of the outer side of an outer part.
Figure 32D:
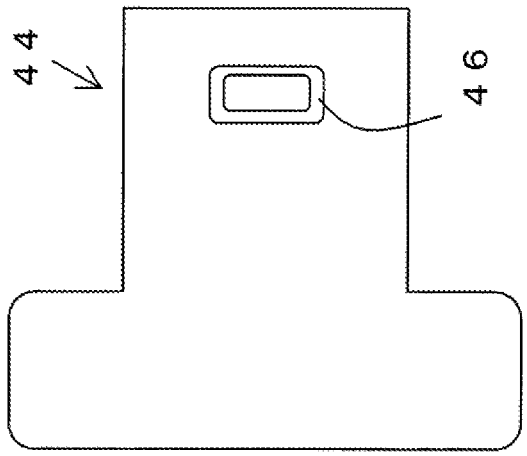
FIG. 32D is a schematic diagram of the inner side of the outer part.

FIG. 32A is a schematic diagram of the outer side of the inner part 42 that forms a diaper equipped with a moisture-detecting RFID tag, according to a modification example of the thirteenth embodiment. FIG. 32B is a schematic diagram of the outer side of the outer part 44. FIG. 32C is a schematic diagram of the inner side of the inner part 42. FIG. 32D is a schematic diagram of the inner side of the outer part 44.

As compared to the diaper equipped with a moisture-detecting RFID tag of FIG. 31, the exemplary diaper equipped with a moisture-detecting RFID tag differs therefrom in that the RFID reader and radio transfer unit 46 is arranged on the outer side of not in the inner part 42 but in the outer part 44. The RFID reader and radio transfer unit 46 may be arranged on the outer side of the outer part 44.

Figure 33C:
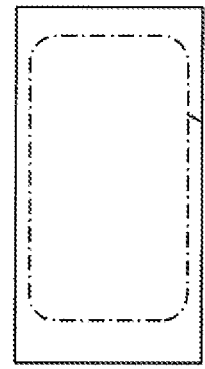
FIG. 33C is a schematic diagram of the inner side of the inner part.
Figure 33D:
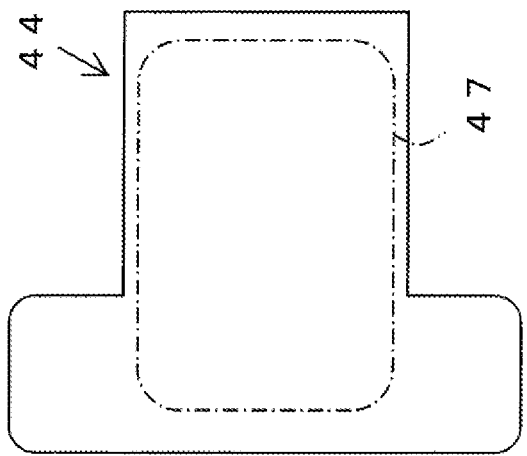
FIG. 33D is a schematic diagram of the inner side of the outer part.
Figure 33A:
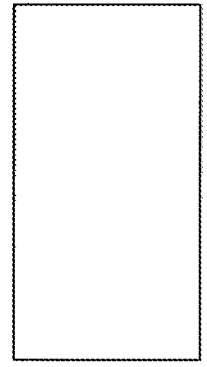
FIG. 33A is a schematic diagram of the outer side of an inner part that forms a diaper equipped with a moisture-detecting RFID tag, according to yet another modification example of the thirteenth embodiment.
Figure 33B:
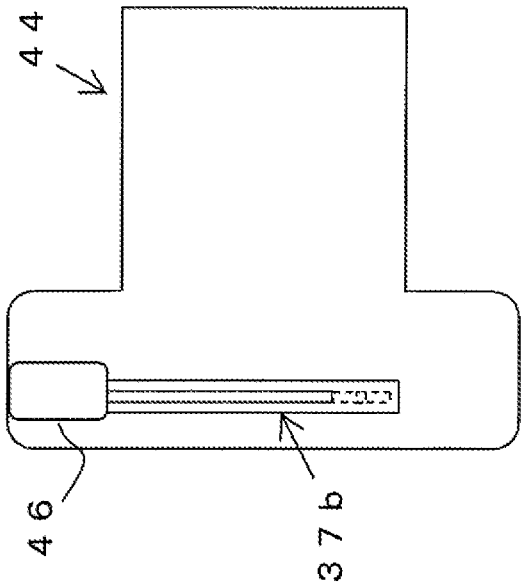
FIG. 33B is a schematic diagram of the outer side of an outer part.

FIG. 33A is a schematic diagram of the outer side of the inner part 42 that forms a diaper equipped with a moisture-detecting RFID tag, according to yet another modification example of the thirteenth embodiment. FIG. 33B is a schematic diagram of the outer side of the outer part 44. FIG. 33C is a schematic diagram of the inner side of the inner part 42. FIG. 33D is a schematic diagram of the inner side of the outer part 44.

Compared to the diaper equipped with a moisture-detecting RFID tag of FIG. 31, this diaper equipped with a moisture-detecting RFID tag differs therefrom in that the moisture-detecting RFID tag unit 37*b* is arranged along the lower back of the back face portion on the outer side of the outer part 44. This diaper equipped with a moisture-detecting RFID tag also differs therefrom in that the RFID reader and radio transfer unit 46 capable of communicating with the relay antenna 20*k* by RFID arranged on the lower back in the vicinity of the relay antenna 20*k*. A system may be constructed according to which the moisture-detecting RFID tag unit 37*b* for the RFID tag and the relay antenna, and the RFID reader and radio transfer unit 46 is attached only on the side of the back (in the back face portion) and no signal is guided to the side of the navel in the front face portion.

Fourteenth Embodiment

Figure 34A:
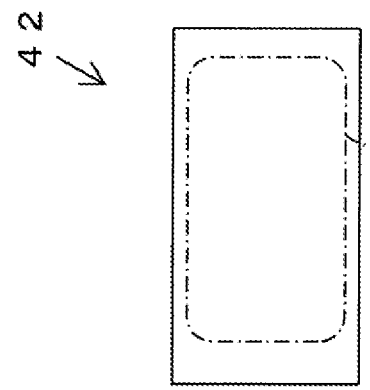
FIG. 34A is a schematic diagram of the outer side of an inner part that forms a diaper equipped with a moisture-detecting RFID tag, according to a fourteenth embodiment.
Figure 34B:
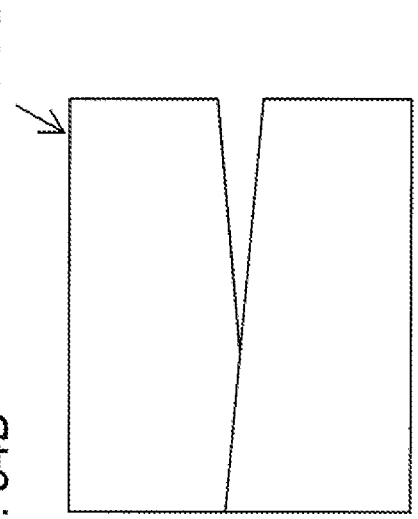
FIG. 34B is a schematic diagram of the outer side of an underpants-type outer part.
Figure 34C:
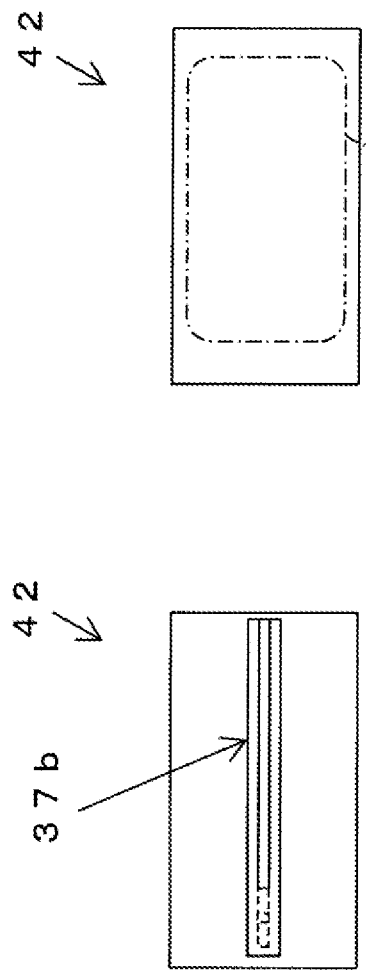
FIG. 34C is a schematic diagram of the inner side of the inner part.

FIG. 34A is a schematic diagram of the outer side of the inner part 42 that forms a diaper equipped with a moisture-detecting RFID tag, according to the fourteenth embodiment. FIG. 34B is a schematic diagram of the outer side of an underpants-type outer part 44*a*. FIG. 34C is a schematic diagram of the inner side of the inner part 42.

This diaper equipped with a moisture-detecting RFID tag includes the inner part 42 and the underpants-type outer part 44*a*, and the all-in-one moisture-detecting RFID tag unit 37*b* including the RFID tag 10*n* and the relay antenna 20*k* is arranged on the outer side of the inner part 42. The moisture-detecting RFID tag unit 37*b* is extended from the back face portion on the outer side of the inner part 42 to the front face portion through the crotch portion. The RFID tag 10 of the moisture-detecting RFID tag unit 37*b* is caused to face the face on the outer side of the inner part 42. The reading of the RFID tag 10*n* can be executed by, for example, a handheld reader in the vicinity of the navel in the front face portion through the relay antenna 20*k* of the moisture-detecting RFID tag unit 37*b*. Instead of the handheld reader, the RFID reader and the radio transfer unit may be used for the reading.

This diaper equipped with a moisture-detecting RFID tag is described for the case where an underpants-type outer part 44*a* having an underpants-like shape such as, for example, a cloth outer part is applied. The underpants-like shape is a shape that has one opening to accommodate the trunk on the one end of its main body of the cylinder-like portion and that has two openings to accommodate legs on the other end thereof, similar to that of an ordinary underpants. For example, a paper inner part 42 and the cloth underpants-type outer part 44*a* may be used in combination. The cloth outer part 44*a* has high adhesiveness for the body in the inner part and has sufficient detection precision. According to the cloth outer part 44*a*, the route of the human body, moisture in the absorptive object, and the RFID tag tends to be formed.

The moisture-detecting RFID tag unit 37*b* only has to be attached to the commercially available inner part 42 as above and any commercially available inner part 42 is therefore usable as it is. The moisture-detecting RFID tag unit 37*b* can be attached by the caretaker when the person needing care wears the diaper. As to the underpants-type outer part 44, nothing needs to be attached thereto on the inner side and the outer side thereof, and any commercially available outer part 44 is usable as it is.

Figure 35A:
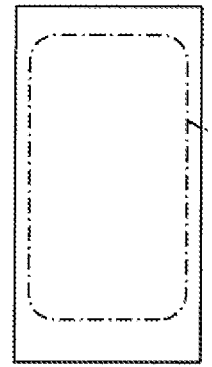
FIG. 35A is a schematic diagram of the outer side of an inner part that forms a diaper equipped with a moisture-detecting RFID tag, according to a modification example of the fourteenth embodiment.
Figure 35C:
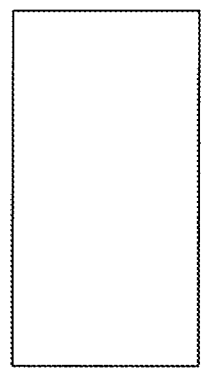
FIG. 35C is a schematic diagram of the inner side of the inner part.
Figure 35B:
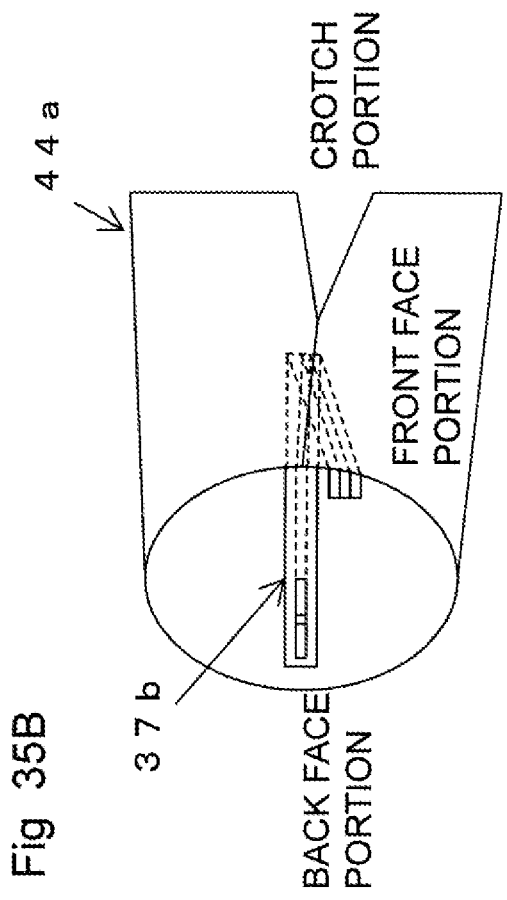
FIG. 35B is a schematic diagram of the outer side of a underpants-type outer part.
Figure 36:
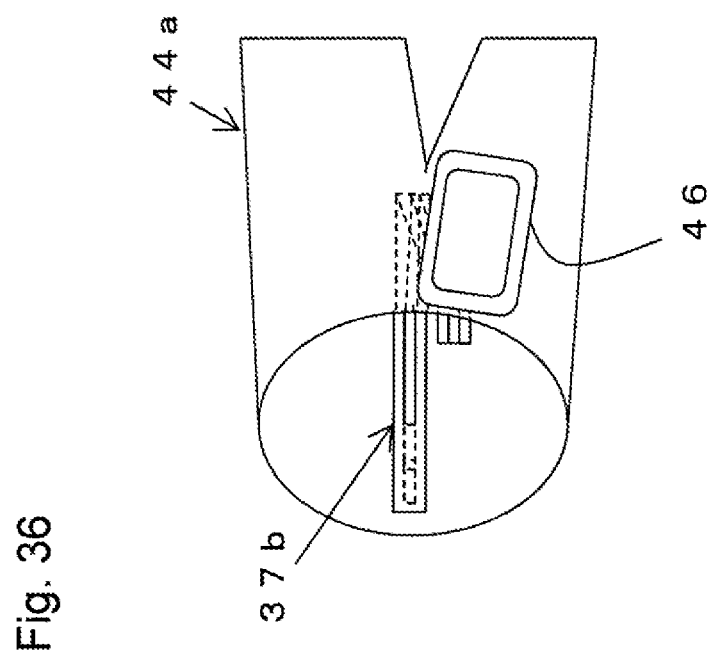
FIG. 36 is a schematic diagram of the case where an RFID reader and a radio transfer unit are used for reading of a diaper equipped with a moisture-detecting RFID tag, according to a modification example of the fourteenth embodiment.

FIG. 35A is a schematic diagram of the outer side of the inner part 42 that forms a diaper equipped with a moisture-detecting RFID tag, according to a modification example of the fourteenth embodiment. FIG. 35B is a schematic diagram of the outer side of the pants-type outer part 44a. FIG. 35C is a schematic diagram of the inner side of the inner part 42. FIG. 36 is a schematic diagram of the case where the RFID reader and radio transfer unit 46 is used for the reading.

Compared to the diaper equipped with a moisture-detecting RFID tag of FIG. 34, this diaper equipped with a moisture-detecting RFID tag differs therefrom in that the moisture-detecting RFID tag unit 37b is arranged on the inner side not in the inner part 42 but in the underpants-type outer part 44. For example, the moisture-detecting RFID tag unit 37b is arranged to be extended from the back face portion on the inner side of the underpants-type outer part 44a to the front face portion through the crotch portion. Any attachment and detachment of the moisture-detecting RFID tag unit 37b by the caretaker are unnecessary for each wearing session by causing the moisture-detecting RFID tag unit 37b to be usually installed on the inner side of the cloth outer part 44a as above. As depicted in FIG. 36, the reading may be executed by, for example, the RFID reader and radio transfer unit 46 instead of the handheld reader.

Fifteenth Embodiment

Figure 37A:
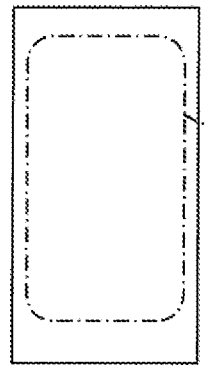
FIG. 37A is a schematic diagram of the outer side of an inner part that forms a diaper equipped with a moisture-detecting RFID tag, according to a fifteenth embodiment.
Figure 37C:
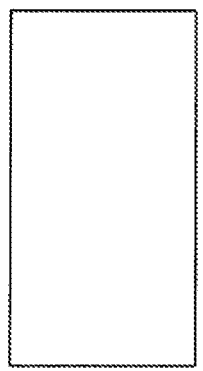
FIG. 37C is a schematic diagram of the inner side of the inner part.
Figure 37B:
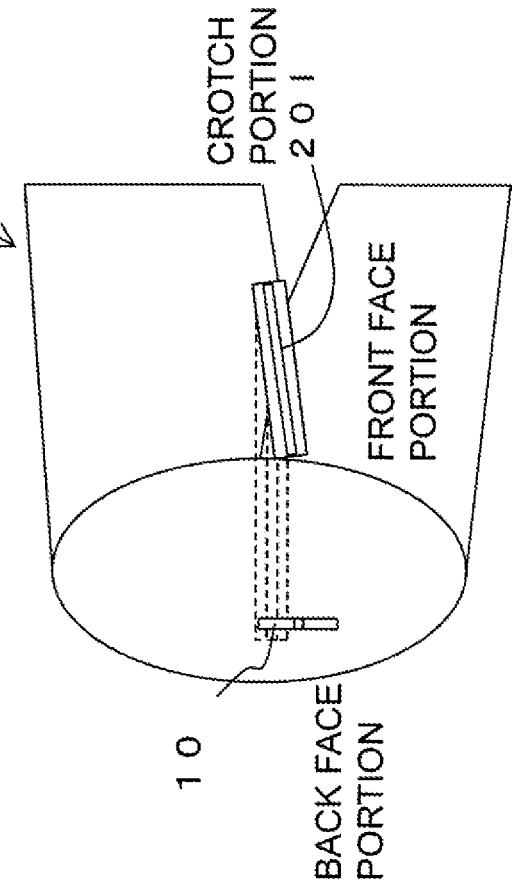
FIG. 37B is a schematic diagram of the outer side of a underpants-type outer part.

FIG. 37A is a schematic diagram of the outer side of the inner part 42 that forms a diaper equipped with a moisture-detecting RFID tag, according to the fifteenth embodiment. FIG. 37B is a schematic diagram of the outer side of the underpants-type outer part 44a. FIG. 37C is a schematic diagram of the inner side of the inner part 42. FIG. 38 is a schematic diagram of the case where the RFID reader and radio transfer unit 46 is used for the reading.

This diaper equipped with a moisture-detecting RFID tag includes the inner part 42 and the underpants-type outer part (for example, the cloth outer part) 44a. The RFID tag 10 is arranged in the back face portion on the inner side of the underpants-type outer part 44a. The relay antenna 20l is arranged to be extended from the back face portion on the outer side of the underpants-type outer part 44a to the front face portion through the crotch portion. The reading of the RFID tag 10n can be executed by, for example, a handheld reader in the vicinity of the navel in the front face portion through the relay antenna 20l. As depicted in FIG. 38, the RFID reader and radio transfer unit 46 may be used for the reading instead of the handheld reader.

For this diaper equipped with a moisture-detecting RFID tag, the thickness of the cloth of the cloth outer part 44a can be used by attaching the relay antenna on the outer side of the cloth outer part 44a that is an example of the underpants-type outer part. The relay antenna 20l is not brought into direct contact with the inner part 42 and the influence on the relay antenna 20l by the moisture of the inner part 42 can be minimized.

The moisture-detecting RFID tag unit 37b only has to be attached to the commercially available inner part 42 as above and any commercially available inner part 42 is therefore usable as it is. The moisture-detecting RFID tag unit 37b can be attached by the caretaker when the person needing care wears the diaper. As to the underpants-type outer part 44a, nothing needs to be attached thereto on the inner side and the outer side thereof, and any commercially available underpants-type outer part 44a is usable as it is.

As to the inner part 42, nothing needs to be attached thereto on the inner side and the outer side thereof, and any commercially available inner part 42 is usable as it is.

On the other hand, for example, the relay antenna 20l of the underpants-type outer part 44a may be attached by the diaper manufacturer in the shipping stage or may be attached by the caretaker. For example, the RFID tag 10 on the inner side of the underpants-type outer part 44a may be attached by the diaper manufacturer in the shipping stage or may be attached by the caretaker.

Sixteenth Embodiment

Figure 39A:
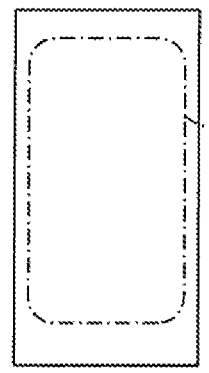
FIG. 39A is a schematic diagram of the outer side of an inner part that forms a diaper equipped with a moisture-detecting RFID tag, according to a sixteenth embodiment.
Figure 39B:
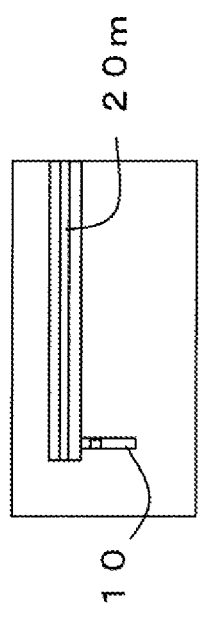
FIG. 39B is a schematic diagram of the outer side of an outer part.
Figure 39C:
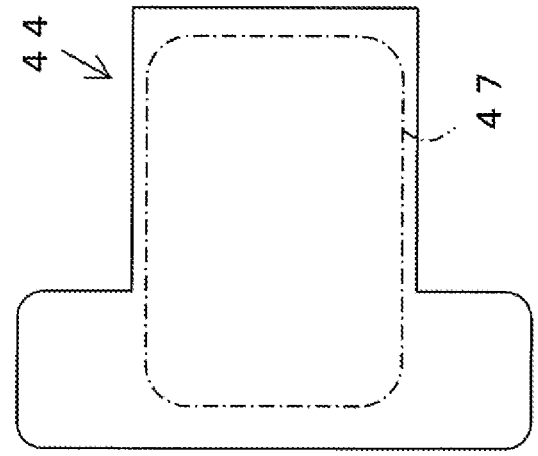
FIG. 39C is a schematic diagram of the inner side of the inner part.
Figure 39D:
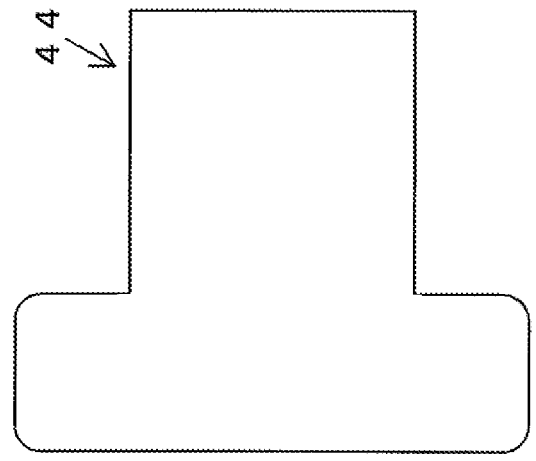
FIG. 39D is a schematic diagram of the inner side of the outer part 44.
Figure 40:
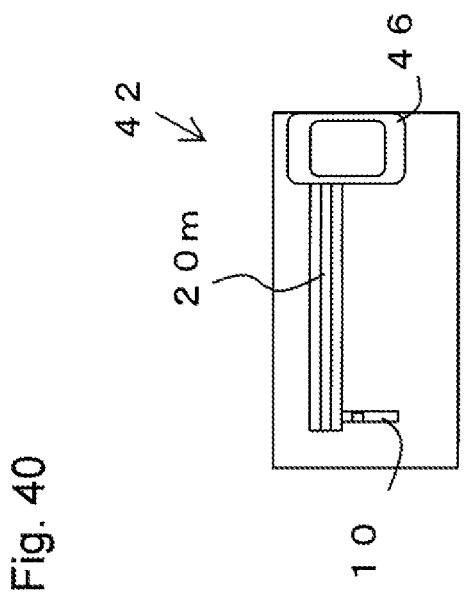
FIG. 40 is a schematic diagram of the case where the RFID reader and radio transfer unit 46 is used for reading of the diaper equipped with a moisture-detecting RFID tag, according to the sixteenth embodiment.

FIG. 39A is a schematic diagram of the outer side of the inner part 42 that forms a diaper equipped with a moisture-detecting RFID tag, according to the sixteenth embodiment. FIG. 39B is a schematic diagram of the outer side of the outer part 44. FIG. 39C is a schematic diagram of the inner side of the inner part 42. FIG. 39D is a schematic diagram of the inner side of the outer part 44. FIG. 40 is a schematic diagram of the case where the RFID reader and radio transfer unit 46 is used for reading.

This diaper equipped with a moisture-detecting RFID tag includes the inner part 42 and the outer part 44. The RFID tag 10 is arranged on the outer side of the inner part 42. The RFID tag 10 may be used alone or held by a holding material. The relay antenna 20m is arranged to be extended from the back face portion on the outer side of the inner part 42 to the front face portion through the crotch portion. The reading of the RFID tag 10 can be executed by, for example, a handheld reader through the relay antenna 20m. As depicted in FIG. 40, the RFID reader and the radio transfer unit may be used for the reading instead of the handheld reader.

In this diaper equipped with a moisture-detecting RFID tag, the RFID tag 10 and the relay antenna 20l are disposed separately from each other. Either one of these components can easily be repaired or replaced even when any defect occurs in the component such as a failure, by disposing these components each to be alone. No restriction is imposed on the attachment of the RFID tag 10 and the relay antenna 20m and the degree of freedom of each of the attachment positions thereof is high.

Seventeenth Embodiment

FIG. 41A is a schematic diagram of the outer side of the inner part 42 that forms a diaper equipped with a moisture-detecting RFID tag, according to the seventeenth embodiment. FIG. 41B is a schematic diagram of the outer side of the outer part 44. FIG. 41C is a schematic diagram of the inner side of the inner part 42. FIG. 41D is a schematic diagram of the inner side of the outer part 44.

This diaper equipped with a moisture-detecting RFID tag includes the inner part 42 and the outer part 44. The all-in-one moisture-detecting RFID tag unit 37b including the RFID tag 10n and the relay antenna 20k is arranged along the lower back on the back face side on the outer side of the inner part 42. The RFID tag 10n of the moisture-detecting RFID tag unit 37b is arranged to face the absorption upper limit position 45 on the back face side on the outer side of the inner part 42. The relay antenna 20n is arranged to be extended from the back face portion on the outer side of the inner part 42 to the front face portion through the crotch portion. The relay antenna 20n is arranged to face the relay antenna 20k of the moisture-detecting RFID tag unit 37b and these relay antennas 20n and 20k are directly connected to or capacitively coupled with each other. The relay antenna 20*n* is the antenna to further relay from the relay antenna 20*k*. The reading of the RFID tag 10*n* can be executed by, for example, a handheld reader through the moisture-detection RFID tag unit 37*b* and the relay antenna 20*n*.

In this diaper equipped with a moisture-detecting RFID tag, the all-in-one moisture-detecting RFID tag unit 37*b* and the relay antenna 20*n* are arranged in combination. The degree of freedom of each of the attachment positions of these components is high. In the exemplary aspect, the relay antenna 20*n* includes no battery and is a relay antenna unit only for the "relaying" only including the antenna for the relaying.

The moisture-detecting RFID tag unit 37*b* and the relay antenna 20*n* only have to be attached to the commercially available inner part 42 as above and any commercially available inner part 42 is therefore usable as it is. The moisture-detecting RFID tag unit 37*b* and the relay antenna 20*n* can be attached by the caretaker when the person needing care wears the diaper. As to the outer part 44, nothing needs to be attached thereto on the inner side and the outer side thereof, and any commercially available outer part 44 is usable as it is.

Eighteenth Embodiment

Figure 42:
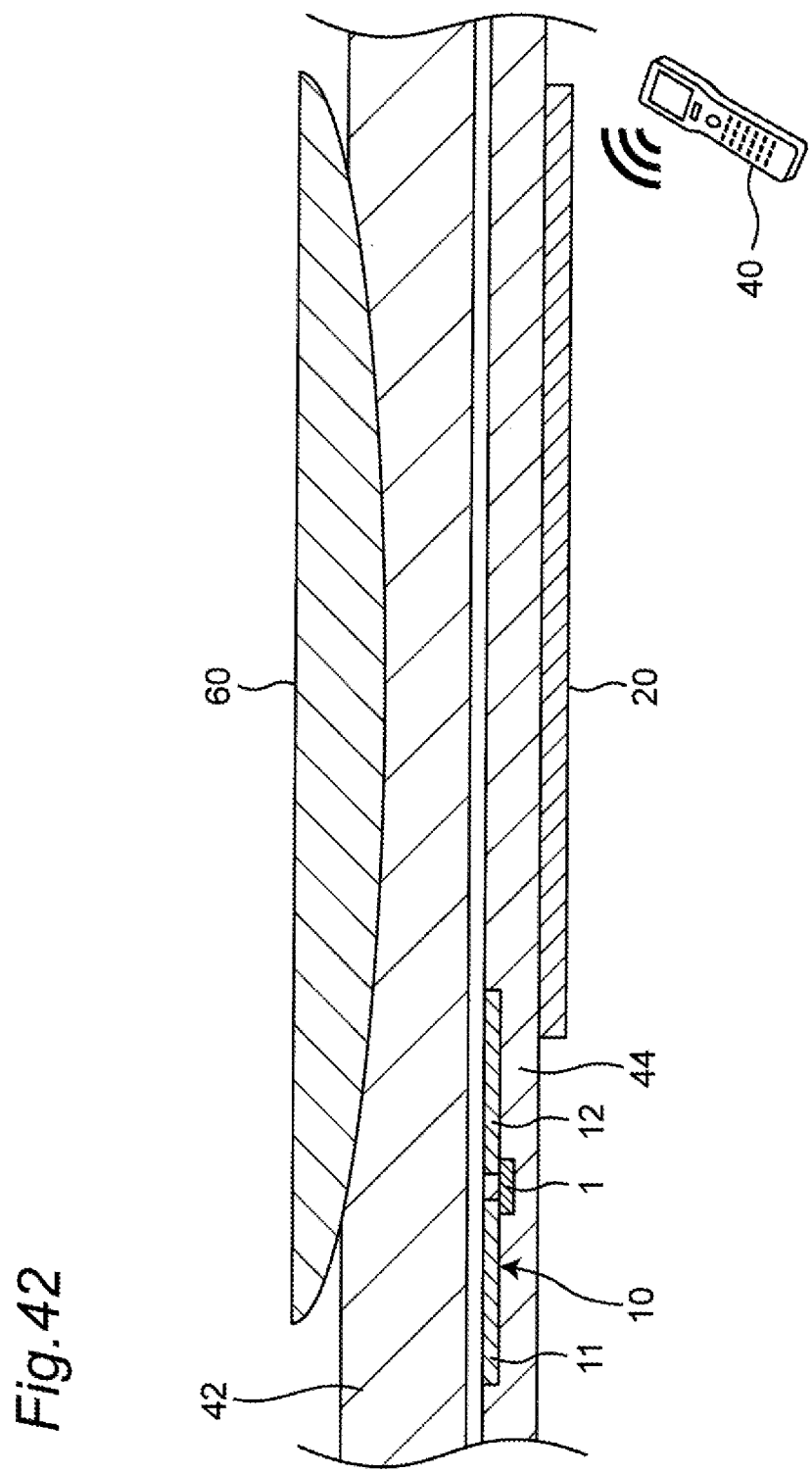
FIG. 42 is a schematic cross-sectional diagram of a cross-sectional configuration of a diaper equipped with an RFID tag, according to an eighteenth embodiment.

FIG. 42 is a schematic cross-sectional diagram of a cross-sectional configuration of a diaper equipped with an RFID tag, according to the eighteenth embodiment. FIG. 43A is a schematic diagram of the outer side of the inner part 42 that forms a diaper equipped with an RFID tag, according to the eighteenth embodiment. FIG. 43B is a schematic diagram of the outer side of the outer part 44. FIG. 43C is a schematic diagram of the inner side of the inner part 42. FIG. 43D is a schematic diagram of the inner side of the outer part 44. FIG. 44A is a schematic diagram of the outer side of the inner part 42 that forms a diaper equipped with an RFID tag, according to another example of the eighteenth embodiment. FIG. 44B is a schematic diagram of the outer side of the outer part 44. FIG. 44C is a schematic diagram of the inner side of the inner part 42. FIG. 44D is a schematic diagram of the inner side of the outer part 44.

As to the diaper equipped with an RFID tag according to the eighteenth embodiment, the diaper includes the inner part 42 and the outer part 44. The RFID tag 10 is arranged on the inner side of the outer part 44, and the relay antenna 20 is arranged on the outer side of the outer part 44 to be capacitively coupled with the one antenna elements of the RFID tag 10 through the outer part 44.

FIG. 42 depicts the cross-section taken when the long axis of the antenna element of the RFID tag 10 and the long axis of the relay antenna 20 match with each other, as depicted in FIG. 44. On the other hand, no cross-sectional diagram is presented for the case where the long axis of the antenna element of the RFID tag 10 and the long axis of the relay antenna 20 intersect each other at a right angle, as depicted in FIG. 43.

FIG. 45A is a schematic cross-sectional diagram of a route of a transmission signal S in the communication with the reader 40 executed when the diaper equipped with an RFID tag, according to the eighteenth embodiment is dry. FIG. 45B is a diagram of a circuit that includes the RFID tag 10 and the relay antenna 20. FIG. 46A is a schematic cross-sectional diagram of a route of the transmission signal S in the communication with the reader 40 executed when the diaper equipped with an RFID tag, according to the eighteenth embodiment has moisture absorbed therein. FIG. 46B is a diagram of a circuit that includes a human body 60, the moisture 54, the RFID tag 10, and the relay antenna 20.

In the above circuit diagram, the human body 60 is depicted as the ground. The moisture 54 is depicted as capacitance. The transmission signal S is depicted by a solid arrow as its transmission direction. In the circuit diagram, for example, only the main circuits are depicted that are each formed between the human body 60, the moisture 54, the antenna element of the RFID tag 10, and the relay antenna 20.

As shown in the circuit diagram of FIG. 45B, when the diaper is dry, the transmission signal S is transmitted between the RFID tag 10 and the reader 40 through the relay antenna 20 and the communication is thereby enabled. In this case, the impedance of the circuit between the human body 60, and the RFID tag 10 and the relay antenna 20 is high and the transmission signal S tends to avoid its transmission to the human body 60.

On the other hand, when the diaper has moisture absorbed therein, the moisture 54 is present inside the inner part 42. In this case, as depicted in the circuit diagram of FIG. 46B, the transmission signal S from the reader 40 flows to the human body 60 through the relay antenna 20 and the moisture 54. In this case, the impedance of the circuit between the human body 60 and the relay antenna 20 is low and the transmission signal S from the reader 40 cannot reach the RFID tag 10. Any communication is therefore unable between the RFID tag 10 and the reader 40.

The RFID tag 10 and the relay antenna 20 are capacitively coupled through the outer part 44. When the moisture 54 is present at a point in the inner part 42 that corresponds to the capacitive coupling between the RFID tag 10 and the relay antenna 20, the impedance of the circuit between the human body 60 and the relay antenna 20 is low. The transmission signal S from the reader 40 flows (escapes) to the human body and does not reach the RFID tag 10.

Reference Example 1

Figures 47A, 47B:
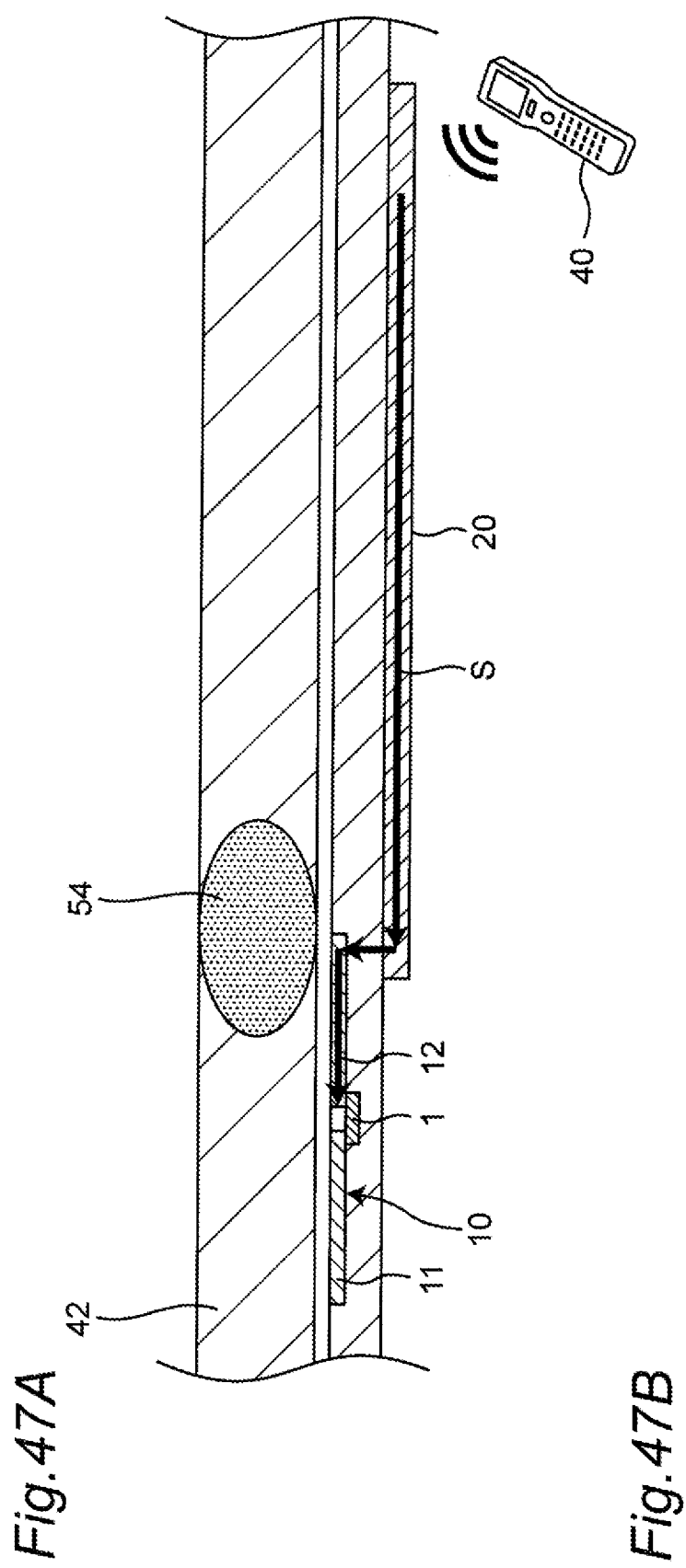
FIG. 47A is a schematic cross-sectional diagram of a route of a transmission signal in the communication with a reader executed when a diaper equipped with an RFID tag, according to Reference Example 1 has moisture absorbed therein
FIG. 47B is a diagram of a circuit that includes the moisture, the RFID tag, and the relay antenna.

FIG. 47A is a schematic cross-sectional diagram of a route of a transmission signal S in the communication with the reader 40 executed when a diaper equipped with an RFID tag, according to Reference Example 1 has moisture absorbed therein. FIG. 47B is a diagram of a circuit that includes the moisture 54, the RFID tag 10, and the relay antenna 20.

Compared to the eighteenth embodiment, this diaper equipped with an RFID tag, according to Reference Example 1 differs therefrom in that no human body is present.

As depicted in the circuit diagram of FIG. 47B, in the case where no human body is present, even when the moisture 54 is present at the point inside the inner part 42 that corresponds to the point of the capacitive coupling between the RFID tag 10 and the relay antenna 20, the transmission signal S from the reader 40 flows from the relay antenna 20 to the RFID tag. Any communication is therefore enabled between the RFID tag 10 and the reader 40 through the relay antenna 20.

Reference Example 2

Figure 48A:
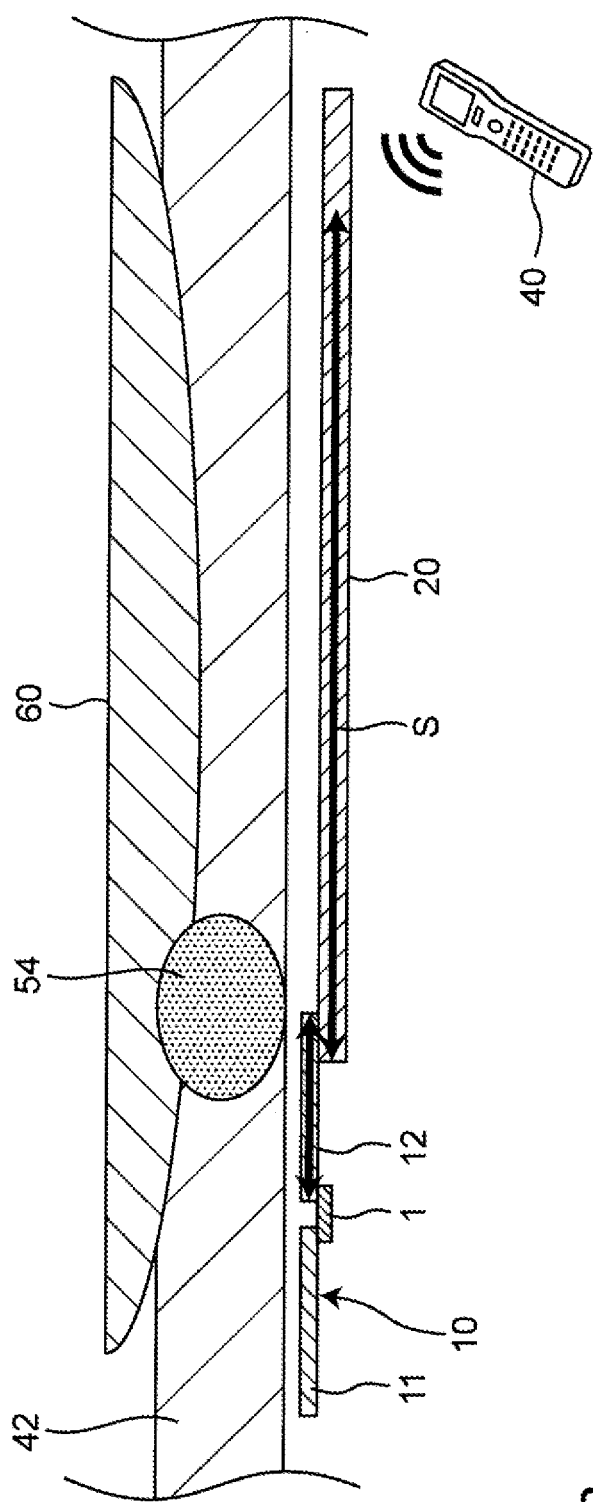
FIG. 48A is a schematic cross-sectional diagram of a route of a transmission signal in the communication with a reader executed when a diaper equipped with an RFID tag, according to Reference Example 2 has moisture absorbed therein
Figure 48B:
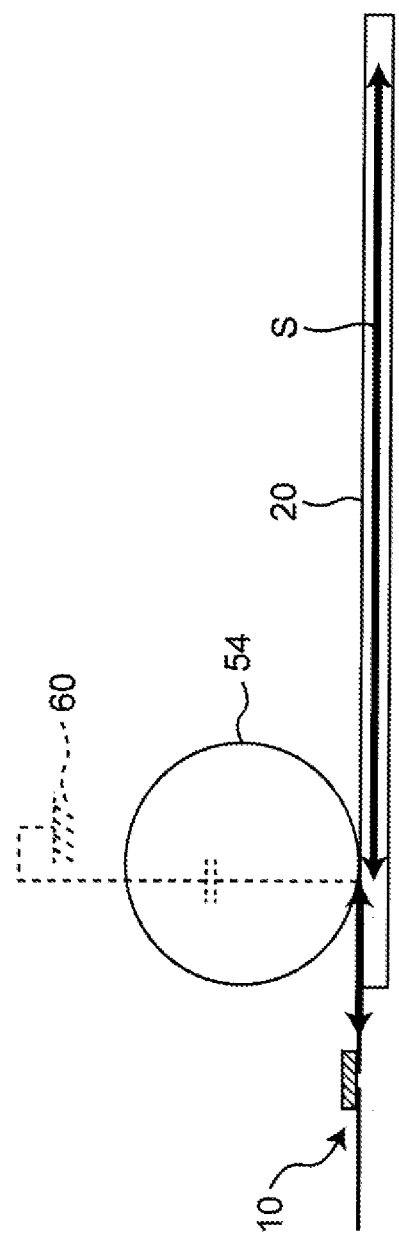
FIG. 48B is a diagram of a circuit that includes a human body, the moisture, the RFID tag, and the relay antenna.

FIG. 48A is a schematic cross-sectional diagram of a route of the transmission signal S in the communication with the reader 40 executed when a diaper equipped with an RFID tag, according to Reference Example 2 has moisture absorbed therein. FIG. 48B is a diagram of a circuit that includes the human body 60, the moisture 54, the RFID tag 10, and the relay antenna 20. Compared to the eighteenth embodiment, the diaper equipped with an RFID tag, according to Reference Example 2 differs therefrom in that the outer part 44 is not included, and the RFID tag 10 and the relay antenna 20 are not capacitively coupled with but are directly connected to each other.

As depicted in the circuit diagram of FIG. 48B, in the diaper equipped with an RFID tag, according to Reference Example 2, the RFID tag 10 and the relay antenna 20 are directly connected to each other. The moisture 54 is present at the point of the capacitive coupling between the RFID tag 10 and the relay antenna 20 inside the inner part 42. In this case, however, the impedance of the direct connection between the RFID tag 10 and the relay antenna 20 is lower than the impedance of the circuit of the relay antenna 20 to the human body 60 through the moisture 54. The transmission signal S from the reader 40 flows from the relay antenna 20 to the RFID tag 10. Any communication is therefore enabled between the RFID tag 10 and the reader 40 through the relay antenna 20.

The case where the connection between the RFID tag 10 and the relay antenna 20 is a direct connection to each other may be not only the case where the relay antenna 20 and the RFID tag 10 are physically in close contact with each other but also the case where the connection portion between the relay antenna 20 and the RFID tag 10 electrically connects these components to each other through solder or the like. For example, the case may further be also the case where the relay antenna 20 and the RFID tag 10 are connected to each other by a micro gap.

Reference Example 3

Figure 49A:
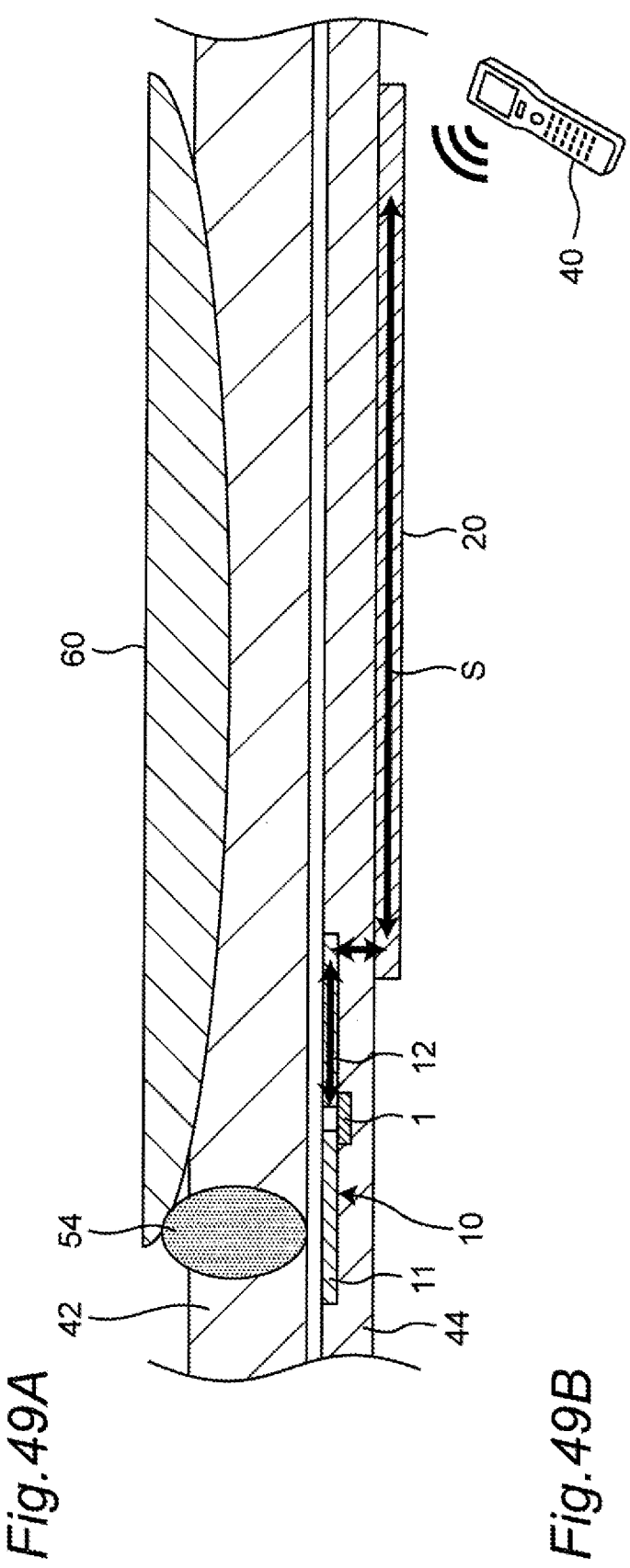
FIG. 49A is a schematic cross-sectional diagram of a route of a transmission signal in the communication with a reader executed when a diaper equipped with an RFID tag, according to Reference Example 3 has moisture absorbed therein
Figure 49B:
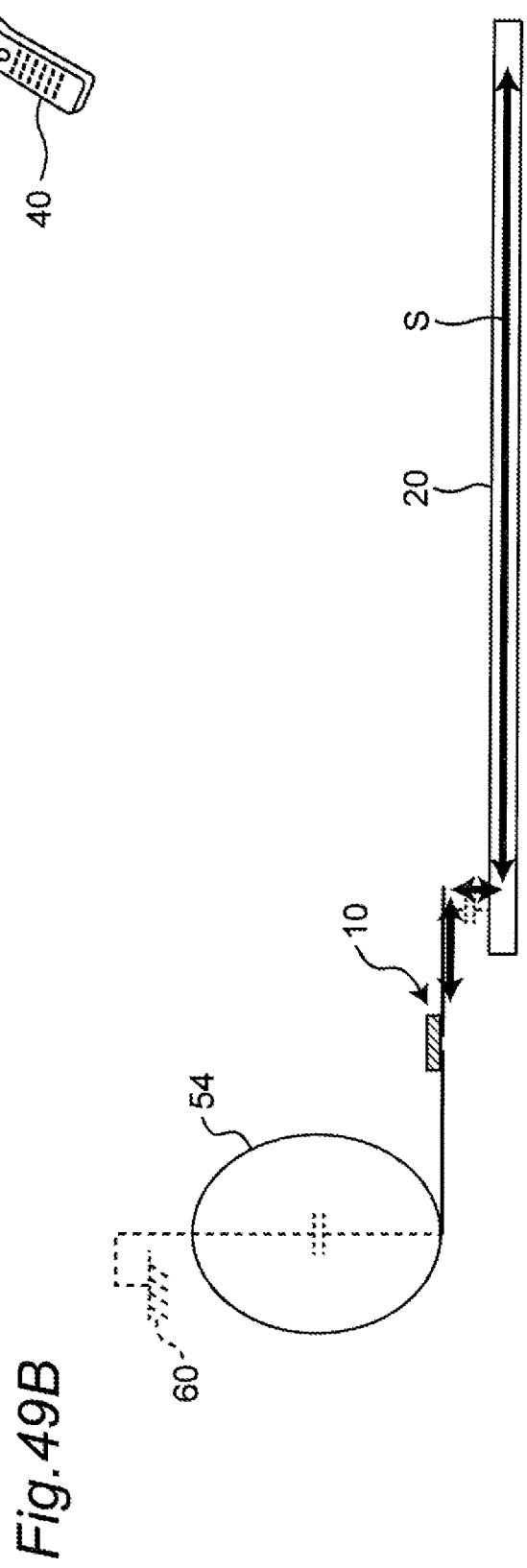
FIG. 49B is a diagram of a circuit that includes a human body, the moisture, the RFID tag, and the relay antenna.

FIG. 49A is a schematic cross-sectional diagram of a route of the transmission signal S in the communication with the reader 40 executed when a diaper equipped with an RFID tag, according to Reference Example 3 has moisture absorbed therein. FIG. 49B is a diagram of a circuit that includes the human body 60, the moisture 54, the RFID tag 10, and the relay antenna 20.

Compared to the eighteenth embodiment, the diaper equipped with an RFID tag, according to Reference Example 3 differs therefrom in that the moisture 54 is present on the side of the antenna element on the side opposite to the antenna element of the RFID tag 10 that is capacitively coupled with the relay antenna 20.

As depicted in the circuit diagram of FIG. 49B, in the diaper equipped with an RFID tag, according to Reference Example 3, for the antenna element on the side opposite to the antenna element capacitively coupled with the relay antenna 20, the impedance of the circuit to the human body 60 through the moisture 54 is low. The transmission signal S from the reader 40 however reaches the RFID tag 10 through the relay antenna 20 and communication is enabled between the RFID tag 10 and the reader 40 through the relay antenna 20.

Nineteenth Embodiment

FIG. 50A is a schematic cross-sectional diagram of a route of the transmission signal S in the communication with the reader 40 executed when a diaper equipped with an RFID tag, according to the nineteenth embodiment has moisture absorbed therein. FIG. 50B is a diagram of a circuit that includes the human body 60, the moisture 54, the RFID tag 10, and the relay antenna 20.

Compared to the diaper equipped with an RFID tag, according to the eighteenth embodiment, the diaper equipped with an RFID tag, according to the nineteenth embodiment differs therefrom in that the moisture 54 is present only in a slit portion between the two antenna elements of the RFID tag 10.

As depicted in the circuit diagram of FIG. 50B, in the diaper equipped with an RFID tag, according to the nineteenth embodiment, the impedance of the circuit between each of the antenna elements and the human body 60 through the moisture 54 is low compared to that of the dry state. Each of the antenna elements and the human body 60 form capacitance through the moisture 54. As a result, any communication is unable because the resonance frequency of the RFID tag is significantly shifted from the resonance frequency in the dry state due to the influence of the circuit by the moisture. In this case, the presence of the moisture 54 can be detected that is present only in the slit portion between the two antenna elements of the RFID tag 10.

Twentieth Embodiment

FIG. 51A is a schematic cross-sectional diagram of a route of the transmission signal S in the communication with the reader 40 executed when a diaper equipped with an RFID tag, according to the twentieth embodiment has moisture absorbed therein. FIG. 51B is a diagram of a circuit that includes the moisture 54, the RFID tag 10, and the relay antenna 20.

Compared to the diaper equipped with an RFID tag, according to the nineteenth embodiment, the diaper equipped with an RFID tag, according to the twentieth embodiment differs therefrom in that no human body is present.

As depicted in the circuit diagram of FIG. 51B, in the diaper equipped with an RFID tag, according to the twentieth embodiment, the two antenna elements form capacitance through the moisture 54. As a result, any communication is unable because the resonance frequency of the RFID tag is significantly shifted from the resonance frequency in the dry state due to the influence of the circuit by the moisture. In this case, the presence of the moisture 54 can be detected that is present only in the slit portion between the two antenna elements of the RFID tag 10.

Twenty-First Embodiment

Figures 52A, 52B:
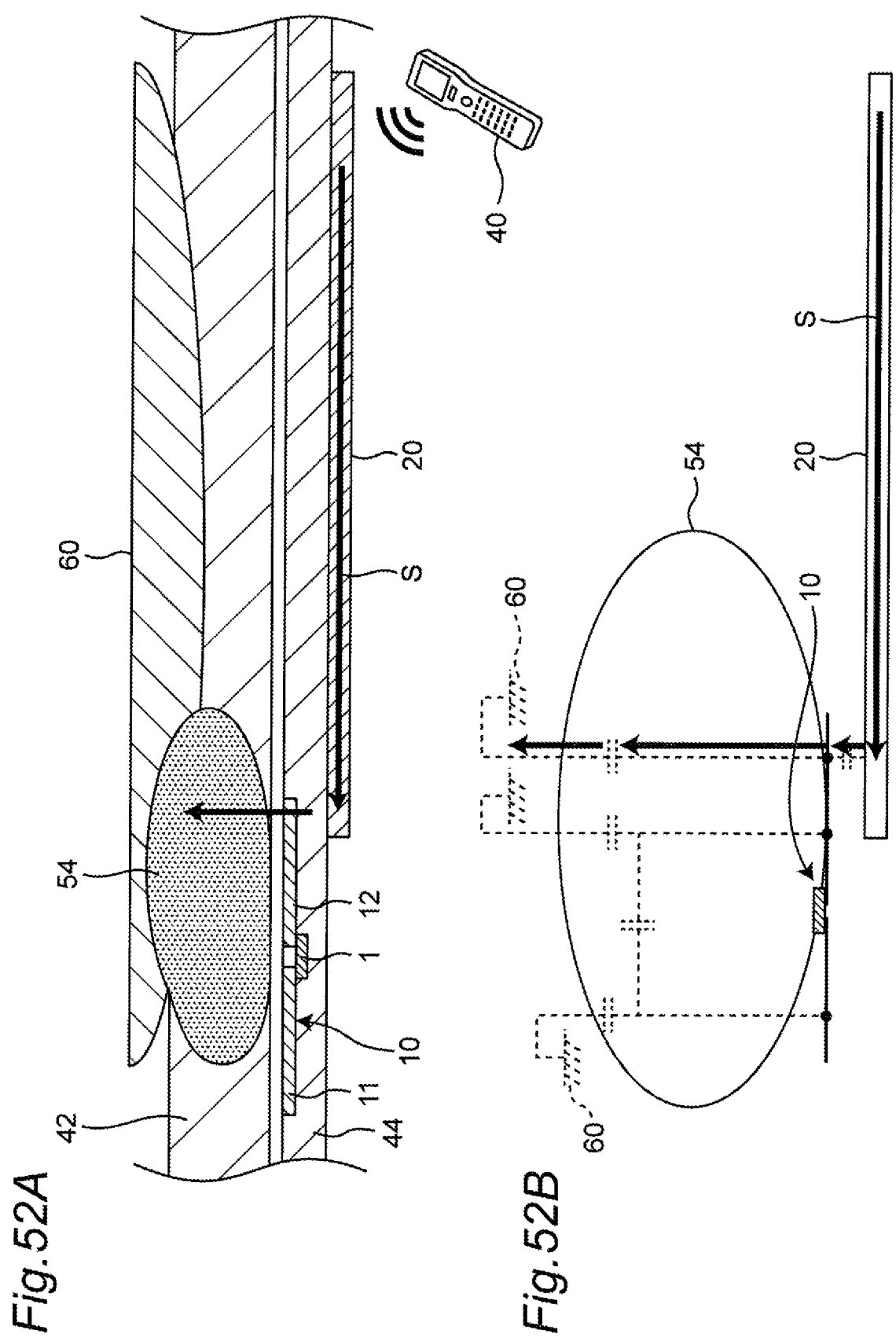
FIG. 52A is a schematic cross-sectional diagram of a route of a transmission signal in the communication with a reader executed when a diaper equipped with an RFID tag, according to a twenty-first embodiment has moisture absorbed therein
FIG. 52B is a diagram of a circuit that includes a human body, the moisture, the RFID tag, and the relay antenna.

FIG. 52A is a schematic cross-sectional diagram of a route of the transmission signal S in the communication with the reader 40 executed when a diaper equipped with an RFID tag, according to the twenty-first embodiment has moisture absorbed therein. FIG. 52B is a diagram of a circuit that includes the human body 60, the moisture 54, the RFID tag 10, and the relay antenna 20.

Compared to the diaper equipped with an RFID tag, according to the nineteenth embodiment, the diaper equipped with an RFID tag, according to the twenty-first embodiment differs therefrom in that the moisture 54 is not only present in the slit portion between the two antenna elements of the RFID tag 10 but also present to the point of the capacitive coupling between the RFID tag 10 and the relay antenna 20.

As depicted in the circuit diagram of FIG. 52B, in the diaper equipped with an RFID tag, according to the twenty-first embodiment, the impedance of the circuit between each of the antenna elements and the human body 60 through the moisture 54 is significantly low compared to that in the dry state. Each of the antenna elements and the human body 60 form capacitance through the moisture 54. As a result, the resonance frequency of the RFID tag is significantly shifted from the resonance frequency in the dry state due to the influence of the circuit by the moisture. The impedance of the circuit between the human body 60 and the relay antenna 20 is significantly low at the point of the capacitive coupling between the RFID tag 10 and the relay antenna 20, and the transmission signal S from the reader 40 therefore flows (escapes) to the human body 60 and does not reach the RFID tag 10. As a result, any communication is unable because of the two effects of the shift of the resonance frequency, and the escaping of the transmission signal S to the human body due to the reduction of the impedance. In this case, the presence of the moisture 54 can more reliably be detected that is present in the slit portion between the two antenna elements of the RFID tag 10 and at the point of the capacitive coupling between the antenna elements and the relay antenna.

Twenty-Second Embodiment

Figure 53A:
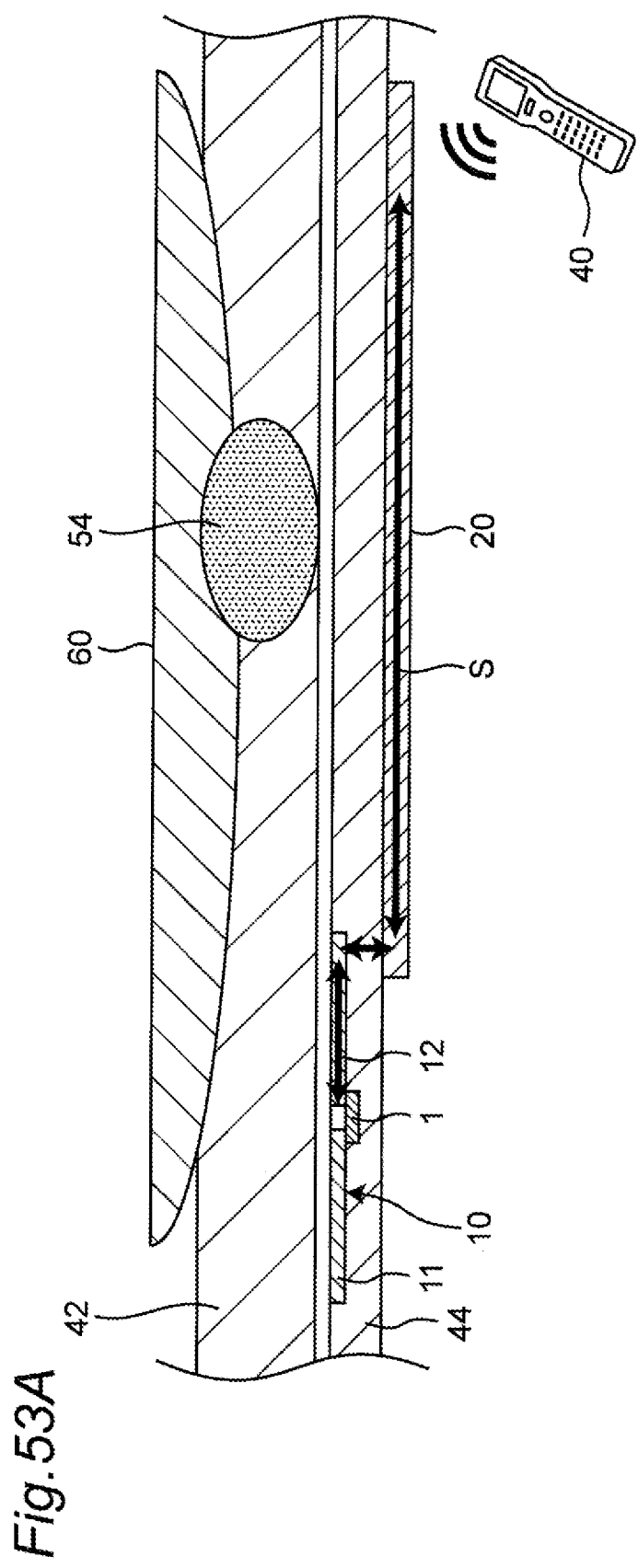
FIG. 53A is a schematic cross-sectional diagram of a route of a transmission signal in the communication with a reader executed when a diaper equipped with an RFID tag, according to a twenty-second embodiment has moisture absorbed therein
Figure 53B:
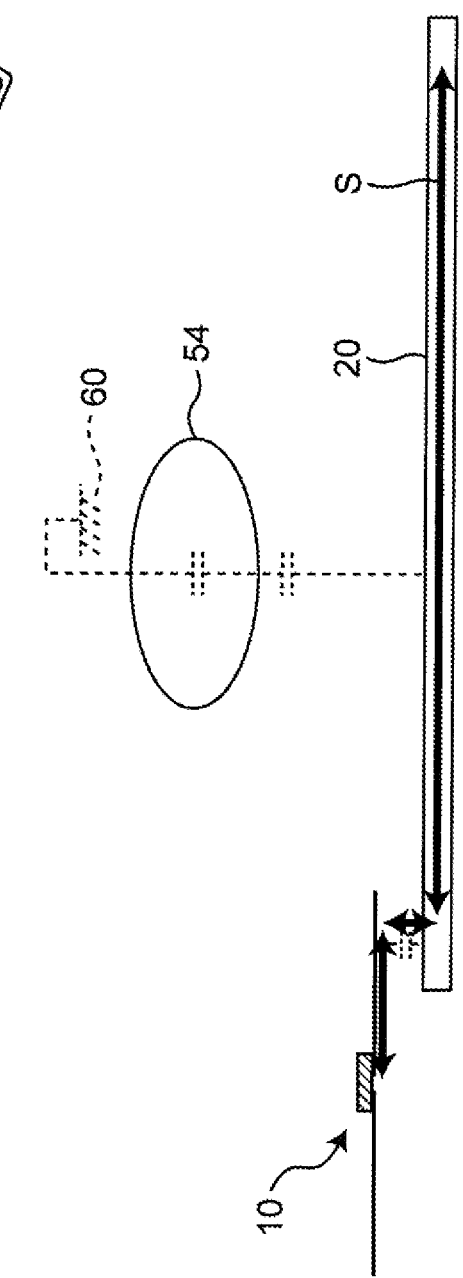
FIG. 53B is a diagram of a circuit that includes a human body, the moisture, the RFID tag, and the relay antenna.

FIG. 53A is a schematic cross-sectional diagram of a route of the transmission signal S in the communication with the reader 40 executed when a diaper equipped with an RFID tag, according to the twenty-second embodiment has moisture absorbed therein. FIG. 53B is a diagram of a circuit that includes the human body 60, the moisture 54, the RFID tag 10, and the relay antenna 20.

Compared to the diaper equipped with an RFID tag, according to the eighteenth embodiment, the diaper equipped with an RFID tag, according to the twenty-second embodiment differs therefrom in that the moisture 54 is present not at the point of the capacitive coupling between the RFID tag 10 and the relay antenna 20 but in the inside of the inner part 42 that corresponds to the intermediate portion of the relay antenna 20.

As depicted in the circuit diagram of FIG. 53B, in the diaper equipped with an RFID tag, according to the twenty-second embodiment, for the circuit between the intermediate portion of the relay antenna 20 and the human body 60 through the moisture 54 in the inner part 42, the impedance of the circuit including the moisture 54 of the inner part 42 is low while the impedance of the circuit sandwiching the outer part 44 in the dry state is high. The transmission signal S from the reader 40 reaches the RFID tag 10 without escaping to the human body 60. As a result, even when the moisture 54 is present in the inside of the inner part 42 that corresponds to the intermediate portion of the relay antenna 20, the influence of the moisture 54 tends to be avoided through the outer part 44 and communication is enabled between the RFID tag 10 and the reader 40.

Reference Example 4

FIG. 54A is a schematic cross-sectional diagram of a route of the transmission signal S in the communication with the reader 40 executed when a diaper equipped with an RFID tag, according to Reference Example 4 has moisture absorbed therein. FIG. 54B is a diagram of a circuit that includes the human body 60, the moisture 54, the RFID tag 10, and the relay antenna 20.

Compared to the diaper equipped with an RFID tag, according to the twenty-second embodiment, the diaper equipped with an RFID tag, according to the Reference Example 4 differs therefrom in that the outer part 44 is not included and the moisture 54 faces the intermediate portion of the relay antenna 20.

As depicted in the circuit diagram of FIG. 54B, in the diaper equipped with an RFID tag, according to Reference Example 4, the impedance of the circuit between the intermediate portion of the relay antenna 20 and the human body 60 through the moisture 54 in the inner part 42 is low. The transmission signal S from the reader 40 therefore escapes to the human body 60 and does not reach the RFID tag 10. As a result, any communication is unable.

<Consideration on Influence by Point of Presence of Moisture>

Figure 55:
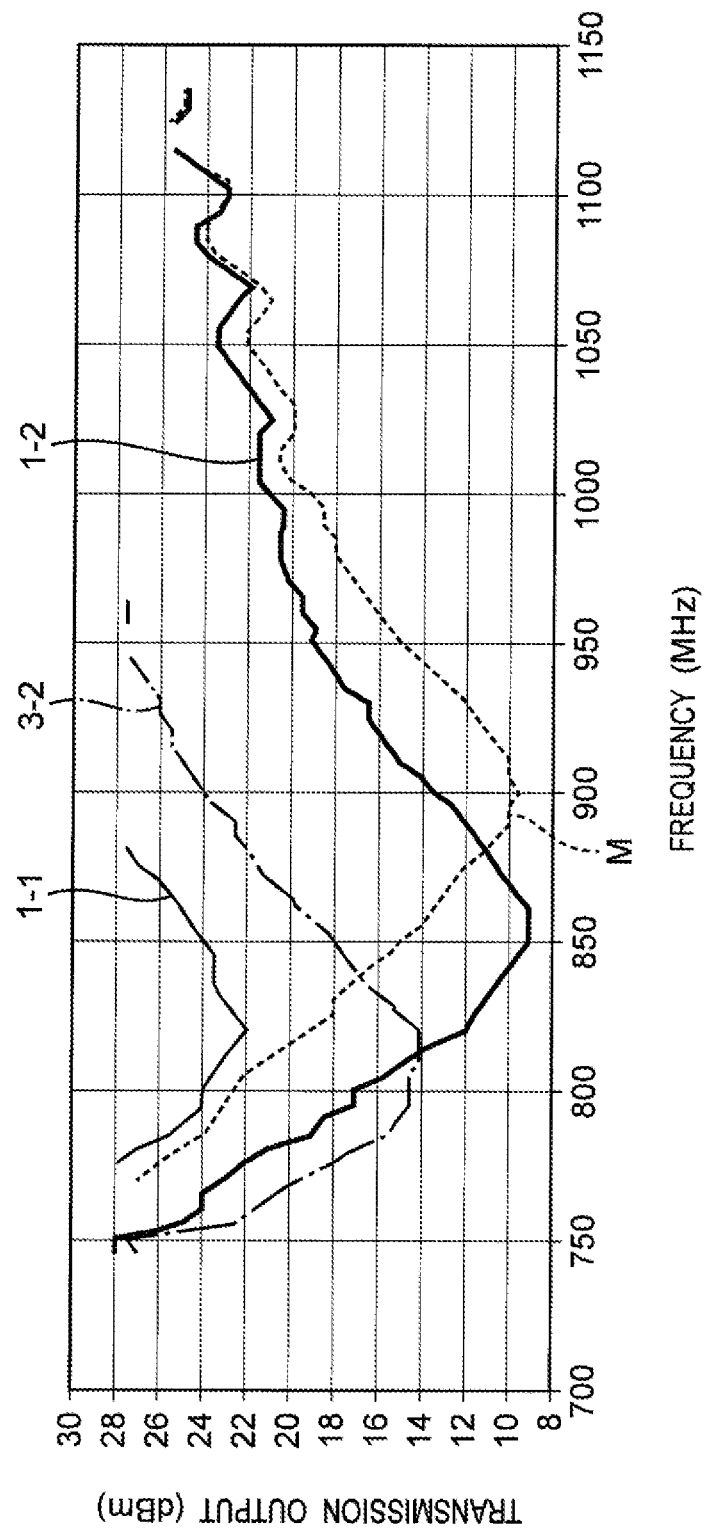
FIG. 55 is a graph of an example of the relation between the frequency and the transmission output for explaining an influence of moisture that is present at a point of the capacitive coupling between the RFID tag and the relay antenna or a point corresponding to a slit portion of the RFID tag.

FIG. 55 is a graph of an example of the relation between the frequency and the transmission output for explaining the influence of moisture that is present at a point of the capacitive coupling between the RFID tag and the relay antenna or a point corresponding to the slit portion of the RFID tag.

FIG. 55 depicts the relation between the frequency and the transmission output in the dry state (M) of the diaper equipped with an RFID tag according to the eighteenth embodiment, a moisture-absorbed state (1-1) of the point corresponding to the point of the capacitive coupling between the RFID tag 10 and the relay antenna 20, a moisture-absorbed state (1-2) of the point corresponding to the point of the capacitive coupling between the RFID tag 10 and the relay antenna 20 in the diaper equipped with an RFID tag, according to Reference Example 1, a moisture-absorbed state (3-1) of the point corresponding to the point of the capacitive coupling between the RFID tag 10 and the relay antenna 20 in the diaper equipped with an RFID tag, according to the nineteenth embodiment, and a moisture-absorbed state (3-2) of the point corresponding to the point of the capacitive coupling between the RFID tag 10 and the relay antenna 20 in the diaper equipped with an RFID tag, according to the twentieth embodiment. The transmission output in the moisture-absorbed state (3-1) according to the twentieth embodiment is not depicted in FIG. 55 because this transmission output is significantly attenuated.

<Influence of Moisture Corresponding to Point of Capacitive Coupling between RFID Tag and Relay Antenna>

It can be seen that, as depicted in FIG. 55, comparing the transmission output between (M) and (1-1), when the moisture 54 is present (1-1) at the point corresponding to the point of the capacitive coupling between the RFID tag 10 and the relay antenna 20, the transmission output is significantly attenuated and any communication is unable. It can be considered that this is because, when the moisture 54 is present at the point corresponding to the point of the capacitive coupling between the RFID tag 10 and the relay antenna 20, the impedance of the circuit between the relay antenna 20 and the human body 60 through the moisture 54 is reduced. When the human body is not present (1-2), the human body to be the escaping destination of the transmission signal S is not present and the transmission output therefore is not substantially varied.

<Influence of Moisture Present at Point Corresponding to Slit Portion of RFID Tag>

It can be seen that, as depicted in FIG. 55, comparing the transmission output between (3-1) and (3-2), when the moisture 54 is present at the point corresponding to the slit portion of the RFID tag, the resonance frequency is shifted from the resonance frequency in the dry state due to the influence of the capacitance between the RFID tag 10 and the two antenna elements through the moisture 54 and the any communication becomes difficult. For example, for the reading at 920 MHz, the transmission output is significantly reduced. Even when the human body is not present (3-2), the shifting of the resonance frequency occurs due to the influence of the moisture and the moisture can be detected for the point corresponding to the slit portion of the RFID tag.

<Direction to Attach RFID Tag to Relay Antenna>

It can be seen that, as depicted in FIG. 55, comparing the transmission output between (1-1) and (3-1), the sensitivity is higher for the presence of the moisture 54 in the case (3-1) where the moisture is present at the point corresponding to the slit portion of the RFID tag than in the case (1-1) where the moisture 54 is present at the point corresponding to the point of the capacitive coupling between the RFID tag 10 and the relay antenna 20.

On the other hand, the cases are present where the RFID tag 10 and the relay antenna 20 are arranged to intersect each other as depicted in FIGS. 43B and 43D and where these components are arranged in the same direction as depicted in FIGS. 44B and 44D, as the direction to attach the RFID tag 10 to the relay antenna 20. When the RFID tag 10 and the relay antenna 20 are arranged in the same direction, the detection is executed at the point of the capacitive coupling sooner than that at the slit portion and the moisture may therefore be detected before the moisture absorption upper limit of the diaper. The moisture absorption upper limit of the diaper may therefore not be accurately detected.

It is more preferred that the relay antenna 20 and the RFID tag 10 be arranged to intersect each other as the direction to attach the RFID tag 10 to the relay antenna 20. The end of the RFID tag 10 may be placed on, for example, the central line of the diaper 30. The relay antenna 20 may be placed on, for example, the central line of the diaper 30.

<Influence of Moisture at Point Corresponding to Intermediate Portion of Relay Antenna>

Figure 56:
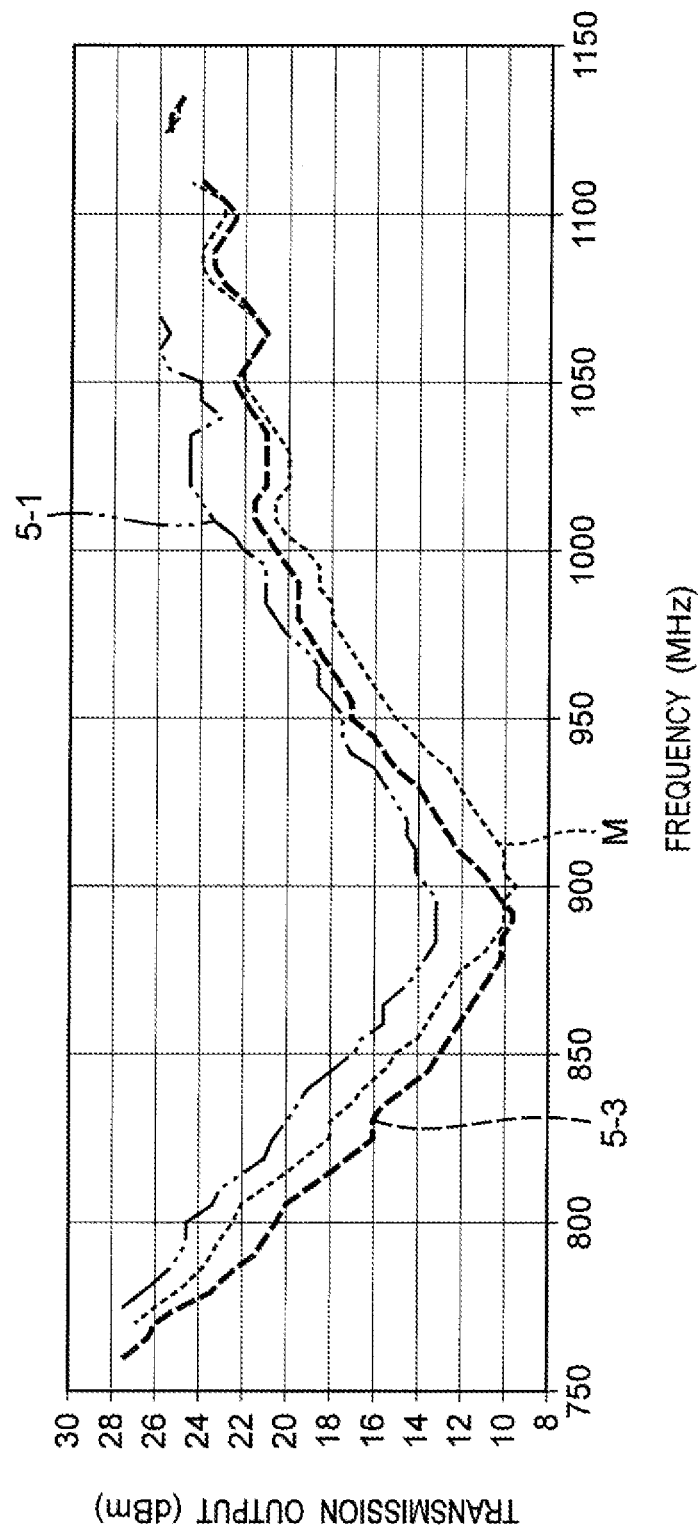
FIG. 56 is a graph of an example of the relation between the frequency and the transmission output for explaining an influence of moisture that is present at a point corresponding to an intermediate portion of the relay antenna.

FIG. 56 is a graph of an example of the relation between the frequency and the transmission output for explaining an influence of the moisture that is present at the point corresponding to the intermediate portion of the relay antenna 20.

FIG. 56 depicts the relation between the frequency and the transmission output in the dry state (M) of the diaper equipped with an RFID tag, according to the eighteenth embodiment and, of the diaper equipped with an RFID tag, according to the twenty-second embodiment, a moisture-absorbed state (5-1) where the moisture 54 is present in the inside of the inner part 42 corresponding to the intermediate portion of the relay antenna 20 and a moisture-absorbed state (5-3) where the human body is not present in the moisture-absorbed state (5-1).

As depicted in FIG. 56, even in the case (5-1) where the moisture 54 is present in the inside of the inner part 42 corresponding to the intermediate portion of the relay antenna 20, any influence of the moisture 54 tends to be avoided when the communication is executed through the outer part 44, and the communication is enabled between the RFID tag 10 and the reader 40. When the human body is not present (5-3), substantially no change from the dry state (M) occurs and the communication is enabled.

In the case where the communication is executed through the outer part 44, even when any moisture is present at the point of the inner part corresponding to the intermediate portion of the relay antenna 20, the influence thereof is weak.

<Influence of Moisture at Point Corresponding to Each of Two Antenna Elements of RFID Tag>

Figure 57:
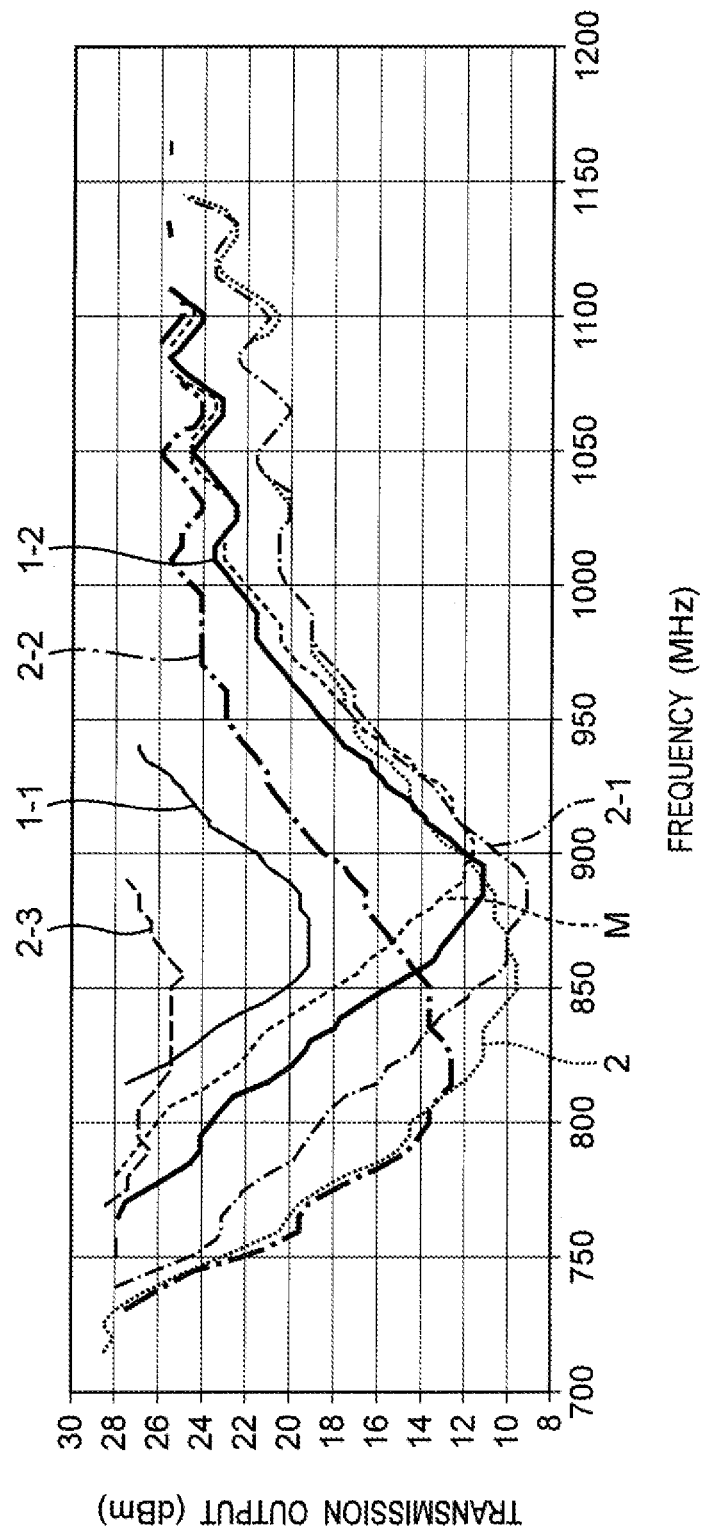
FIG. 57 is a graph of an example of the relation between the frequency and the transmission output for explaining an influence of moisture at a point corresponding to each of two antenna elements of the RFID tag.

FIG. 57 is a graph of an example of the relation between the frequency and the transmission output for explaining the influence of the moisture at a point corresponding to each of the two antenna elements of the RFID tag 10.

FIG. 57 depicts the relation between the frequency and the transmission output in the dry state (M) of the diaper equipped with an RFID tag, according to the eighteenth embodiment, the moisture-absorbed state (1-1) of the point corresponding to the point of the capacitive coupling between the RFID tag 10 and the relay antenna 20, the moisture-absorbed state (1-2) of the point corresponding to the point of the capacitive coupling between the RFID tag 10 and the relay antenna 20 in the case where the human body is not present in the diaper equipped with an RFID tag, according to Reference Example 1, the case (2) where the moisture 54 is present on the side of the antenna element on the side opposite to the antenna element of the RFID tag 10 capacitively coupled with the relay antenna 20 in the diaper equipped with an RFID tag, according to Reference Example 3, the case (2-1) where the human body is not present in (2), the case (2-2) where the moisture 54 is present on the side of the antenna element on the side opposite to the antenna element of the RFID tag 10 capacitively coupled with the relay antenna 20 and in the slit portion between the two antenna elements of the RFID tag 10 for the case where the human body is not present, and the case (2-3) where the moisture 54 is present on the side of the antenna element on the side opposite to the antenna element of the RFID tag 10 capacitively coupled with the relay antenna 20 and in the slit portion between the two antenna elements of the RFID tag 10 for the case where the human body is present.

As illustrated in in FIG. 57, it is shown that the result as to whether the communication is unable (1-1) or is enabled (2) is changed depending on whether the point at which the moisture is present is on the side (1-1) of the antenna element of the RFID tag 10 capacitively coupled with the relay antenna 20 or the side (2) of the antenna element on the opposite side.

It is further shown that the transmission output is significantly reduced in the case (2-3) where the moisture 54 is present on the side of the antenna element on the side opposite to the antenna element of the RFID tag 10 capacitively coupled with the relay antenna 20 and, in addition, the moisture 54 is also present in the slit portion between the two antenna elements of the RFID tag 10.

In the cases (1-2, 2-1, and 2-2) where the human body is not present, the communication is enabled in any of these cases.

As above, it can be seen that not only the presence of the moisture but also the presence of the human body are important for detecting the moisture. It can also be seen that whether the detection is enabled or unable is changed in accordance with the point at which the moisture is present.

The fact that the moisture reaches a specific point in the diaper can be detected by optimizing the way of placing the RFID tag 10 in the diaper 30.

As to the diaper equipped with a moisture-detecting RFID tag, the moisture-detecting RFID tag may be an RFID tag.

The frequency band to use the moisture-detecting RFID tag may be any band such as an LF-band, an HF-band, a UHF-band, or an SHF-band. The moisture-detecting RFID tag is not limited to the one that has a what-is-called tag function and may have other functions such as a moisture-detecting RFID tag having a reader/writer function.

This disclosure includes any proper combination of any optional embodiments and/or any optional Examples of the above various embodiments and/or Examples, and the effects to be achieved by the combined embodiments and/or Examples can be achieved.

According to the sanitary article equipped with a moisture-detecting RFID tag of the present invention, the relay antenna is included therein that is connected to the moisture-detecting RFID tag 10 and that extends the communication range by relaying the output of the moisture-detecting RFID tag. Any moisture can thereby be highly sensitively detected in the communication range extended by the relay antenna.

EXPLANATIONS OF LETTERS OR NUMBERS

1 RFID element
2 moisture-absorptive material
3 junctural pattern
4a first connection pattern
4b second connection pattern
5a, 5b end portion
6a, 6b open end
7 capacitor (capacitance)
8a, 8b branching point
9a, 9b turnback portion
10, 10a, 10b, 10c, 10d, 10e, 10f, 10g, 10h, 10i, 10j, 10k, 10l, 10m, 10n moisture-detecting RFID tag
11 first radiation electrode (antenna element)
12 second radiation electrode (antenna element)
13 opposite electrode
14 moisture-absorptive material
15 capacitor element
16 opposite portion
17 capacitive coupling
20, 20a, 20b, 20c, 20d, 20e, 20f, 20g, 20h, 20i, 20j, 20k, 20l, 20m, 20n, 20o relay antenna (relay antenna unit)
21 RFIC chip
22 conductive joining material
23 terminal electrode
24 sealing resin
25 multi-layered substrate
26a first input and output terminal (terminal electrode)
26b second input and output terminal (terminal electrode)
28a, 28b, 28c conductor
29a, 29b spacer
30, 30a, 30b diaper (diaper equipped with a moisture-detecting RFID tag)
30c relay system for a diaper equipped with a moisture-detecting RFID tag
32 waterproof material
34, 34a, 34b moisture-absorptive material
36 gathering
37 relay antenna unit
37a, 37b, 37c moisture-detecting RFID tag unit
38 supporter
39 guideline
40 reader/writer
41 relay antenna terminating portion
42 inner part (diaper)
43 border line
44 outer part (diaper)
44a cloth outer part (diaper)
45 absorption upper limit position
46 RFID reader and radio transfer unit
47 border line
48 diaper
49 position mark
60 human body
70 bed

The invention claimed is:

1. A sanitary article for communicating a moisture indication signal, the sanitary article having a front face, a crotch portion and a back face, the sanitary article comprising:
    a moisture-absorptive material;
    a moisture-detecting RFID tag disposed adjacent to the moisture-absorptive material disposed on the crotch portion or the back face and including an RFIC element; and an antenna element connected to the RFIC element; and
    a relay antenna connected to the moisture-detecting RFID tag on the crotch portion or the back face and extended from the crotch portion or the back face to the front face of the sanitary article, the relay antenna elongated in the sanitary article to extend a communication range by relaying an output of the moisture-detecting RFID tag,
    wherein the moisture-detecting RFID tag is configured to vary an output of a communication distance based on a variation of an amount of moisture in the moisture-absorptive material, and
    wherein the RFID tag and the relay antenna intersect each other, and the RFID tag is directly coupled to or capacitively coupled with the relay antenna.

2. The sanitary article according to claim 1, wherein the relay antenna is capacitively coupled with the antenna element of the moisture-detecting RFID tag.

3. The sanitary article according to claim 1, further comprising:
    an inner part that includes the moisture-absorptive material; and
    an outer part that covers the inner part.

4. The sanitary article according to claim 3, wherein the outer part is an underpants-type outer part having an underpants-like shape.

5. The sanitary article according to claim 3, wherein the moisture-detecting RFID tag is disposed on an inner side of the outer part, and the relay antenna is disposed on an outer side of the outer part that faces an antenna element of the moisture-detecting RFID tag sandwiching the outer part therebetween, such that the related antenna is capacitively coupled with the antenna element of the moisture-detecting RFID tag.

6. The sanitary article according to claim 1, further comprising a plurality of pairs of each of the moisture-detecting RFID tag and the relay antenna connected to the moisture-detecting RFID tag.

7. The sanitary article according to claim 1, wherein the sanitary article is a diaper.

8. The sanitary article according to claim 7, wherein the moisture-detecting RFID tag is disposed in the crotch portion of the diaper, and the relay antenna extends from the crotch portion to at least one of the front face and the back face of the diaper.

9. The sanitary article according to claim 7, wherein the moisture-detecting RFID tag is disposed in the back face of the diaper, and the relay antenna extends from the back face to the front face of the diaper.

10. The sanitary article according to claim 9, wherein the relay antenna extends from the back face to the front face through the crotch portion of the diaper.

11. The sanitary article according to claim 1,
    wherein the moisture-detecting RFID tag comprises at least one radiation electrode and at least one opposing electrode with at least a portion of the moisture-absorptive material disposed therebetween, and
    wherein the moisture-detecting RFID tag varies the output of the at least one of the communication distance and the signal intensity based on a variation of a dielectric constant caused by the portion of the moisture-absorptive material disposed between the at least one radiation electrode and the at least one opposing electrode.

12. A moisture-detecting RFID tag unit configured to be attached to a sanitary article having a front face, a crotch portion a back face, and a moisture-absorptive material, the moisture-detecting RFID tag unit comprising:
  a band-like supporter;
  a moisture-detecting RFID tag disposed on the supporter and adjacent to the moisture-absorptive material disposed on the crotch portion or the back face of the sanitary article when the moisture-detecting RFID tag is attached to the sanitary article; and
  a relay antenna capacitively coupled with an antenna element of the moisture-detecting RFID tag on the crotch portion or the back face and extended from the crotch portion or the back face to the front face of the sanitary article when the moisture-detecting RFID tag is attached to the sanitary article, the relay antenna comprising an elongated shape configured to extend a communication range by relaying an output of the moisture-detecting RFID tag,
  wherein the moisture-detecting RFID tag and the relay antenna intersect each other.

13. An apparatus for communicating a moisture indication signal, the apparatus comprising:
  a sanitary article including an inner part comprising a moisture-absorptive material, and an outer part covering the inner part, with the sanitary article having a front face, a crotch portion and a back face; and
  a moisture-detecting RFID tag unit disposed in the sanitary article, the moisture-detecting RFID tag unit configured to vary an output of a communication distance based on a variation of an amount of moisture in the moisture-absorptive material,
  wherein the moisture-detecting RFID tag unit comprises:
    a band-like supporter;
    a moisture-detecting RFID tag that is disposed on the supporter and that is adjacent to the moisture-absorptive material disposed on the crotch portion or the back face of the sanitary article; and
    an elongated relay antenna in the sanitary article and capacitively coupled with an antenna element of the moisture-detecting RFID tag, with the elongated relay antenna being disposed on the crotch portion or the back face and extended from the crotch portion or the back face to the front face of the sanitary article and being configured to extend a communication range by relaying an output of the moisture-detecting RFID tag,
  wherein the elongated relay antenna intersects the moisture-detecting RFID tag in a direction in which the elongated relay antenna extends.

14. The apparatus according to claim 13, wherein the outer part is an underpants-type outer part.

15. The apparatus according to claim 13, wherein the moisture-detecting RFID tag unit is disposed on an outer side of the inner part.

16. The apparatus according to claim 13, wherein the moisture-detecting RFID tag unit is disposed on an inner side of the outer part.

17. The apparatus according to claim 13, wherein the moisture-detecting RFID tag unit is disposed on an outer side of the outer part.

18. The apparatus according to claim 13, further comprising another relay antenna that is connected to the relay antenna of the moisture-detecting RFID tag unit.

19. The apparatus according to claim 13, further comprising a plurality of moisture-detecting RFID tag units including the moisture-detecting RFID tag unit.

20. The apparatus according to claim 13,
  wherein the moisture-detecting RFID tag comprises at least one radiation electrode and at least one opposing electrode with at least a portion of the moisture-absorptive material disposed therebetween, and
  wherein the moisture-detecting RFID tag varies the output of the at least one of the communication distance and the signal intensity based on a variation of a dielectric constant caused by the portion of the moisture-absorptive material disposed between the at least one radiation electrode and the at least one opposing electrode.

* * * * *